(12) United States Patent
Lemke et al.

(10) Patent No.: US 10,519,101 B2
(45) Date of Patent: Dec. 31, 2019

(54) TRANS-CYCLOOCTENE AMINO AND HYDROXY ACIDS AND THEIR USE IN MULTIPLE CYCLOADDITION REACTIONS FOR LABELING OF MOLECULES

(71) Applicant: EUROPEAN MOLECULAR BIOLOGY LABORATORY, Heidelberg (DE)

(72) Inventors: Edward Lemke, Mannheim (DE); Carsten Schultz, Heidelberg (DE); Tilman Plass, Heidelberg (DE); Ivana Nikic, Heidelberg (DE); Jan-Erik Hoffmann, Heidelberg (DE); Iker Valle Aramburu, Heidelberg (DE)

(73) Assignee: European Molecular Biology Laboratory, Heidelberg (DE)

( * ) Notice: Subject to any disclaimer, the term of this patent is extended or adjusted under 35 U.S.C. 154(b) by 77 days.

(21) Appl. No.: 15/111,138

(22) PCT Filed: Jan. 14, 2015

(86) PCT No.: PCT/EP2015/050555
§ 371 (c)(1),
(2) Date: Jul. 12, 2016

(87) PCT Pub. No.: WO2015/107064
PCT Pub. Date: Jul. 23, 2015

(65) Prior Publication Data
US 2016/0340297 A1    Nov. 24, 2016

(30) Foreign Application Priority Data

Jan. 14, 2014   (EP) .................................. 14151175

(51) Int. Cl.
| | | |
|---|---|---|
| C07C 57/26 | (2006.01) | |
| C07C 69/02 | (2006.01) | |
| C07C 271/22 | (2006.01) | |
| C07C 271/34 | (2006.01) | |
| G01N 33/533 | (2006.01) | |
| G01N 33/58 | (2006.01) | |

(52) U.S. Cl.
CPC .......... *C07C 271/22* (2013.01); *C07C 271/34* (2013.01); *G01N 33/533* (2013.01); *G01N 33/582* (2013.01)

(58) Field of Classification Search
CPC ............................... C07C 57/26; C07C 69/02
USPC ........................................... 560/128; 562/510
See application file for complete search history.

(56) References Cited

U.S. PATENT DOCUMENTS 9,085,514 B2    7/2015  Lemke et al.
2010/0297693 A1   11/2010  Young et al.

FOREIGN PATENT DOCUMENTS

| EP | 2192185 A1 | 6/2010 |
|---|---|---|
| WO | 2002085923 A2 | 10/2002 |
| WO | 2002086075 A2 | 10/2002 |
| WO | 2006050262 A2 | 5/2006 |
| WO | 2010051530 A2 | 5/2010 |
| WO | 2010119389 A2 | 10/2010 |
| WO | 2011095336 A2 | 8/2011 |
| WO | 2011112970 A2 | 9/2011 |
| WO | 2012104422 A1 | 8/2012 |
| WO | 2013029801 A2 | 3/2013 |
| WO | 2013108044 A2 | 7/2013 |
| WO | 2013152359 A1 | 10/2013 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Agard, et al., "A Strain-Promoted [3+2] Azide—Alkyne Cycloaddition for Covalent Modification of Biomolecules in Living Systems", J Am Chem soc 126, 15046-15047 (2004).
Blackman, et al., "Tetrazine Ligation: Fast Bioconjugation Based on Inverse-Electron-Demand Diels—Alder Reactivity", J Am Chem Soc 130, 13518-13519 (2008).
Borrmann, et al., "Genetic Encoding of a Bicyclo[6.1.0]nonyne-Charged Amino Acid Enables Fast Cellular Protein Imaging by Metal-Free Ligation", ChemBioChem 13, 2094-2099 (2012).
Carpino, et al., "The 9-Fluorenylmethoxycarbonyl Amino-Protecting Group", J Org Chem vol. 37 (22), 3404-3409 (1972).
Chang, et al., "Copper-free click chemistry in living animals", PNAS vol. 107 (5), 1821-1826 (2010).
Chatterjee, et al., "A Versatile Platform for Single- and Multiple-Unnatural Amino Acid Mutagenesis in *Escherichia coli*", Biochemistry 52, 1828-1837 (2013).

(Continued)

*Primary Examiner* — Douglas M Willis
(74) *Attorney, Agent, or Firm* — Viksnins Harris Padys Malen LLP

(57) ABSTRACT

The present invention relates to compounds of formula:

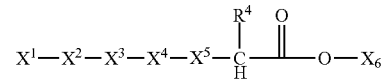

and methods for linking tetrazines with dienophiles to establish at least two linkages by sequentially performing at least two cycloaddition reactions. The methods in particular allow establishing multi-labeling strategies. In particular, the invention relates to methods for forming linkages by cycloaddition reactions, wherein the method comprises reacting a first alkyl-substituted tetrazine with a first dienophile comprising a trans-cyclooctenyl group followed by reacting a second tetrazine with a second dienophile comprising a cyclooctynyl group, wherein the reaction of the first tetrazine with the first dienophile proceeds in the presence of the second dienophile.

3 Claims, 20 Drawing Sheets

Specification includes a Sequence Listing.

(56) References Cited

OTHER PUBLICATIONS

Chin, et al., "Addition of p-Azido-L-phenylalanine to the Genetic Code of *Escherichia coli*", J Am Chem Soc 124, 9026-9027 (2002).
Chin, et al., "An Expanded Eukaryotic Genetic Code", Science vol. 301, 964-967 (2003).
Devaraj, et al., "Bioorthogonal Turn-On Probes for Imaging Small Molecules inside Living Cells", *Angew Chem Int Ed* 49, 2869-2872 (2010).
Devaraj, et al., "Fast and Sensitive Pretargeted Labeling of Cancer Cells via Tetrazine/Trans-Cyclooctene Cycloaddition", Angew Chem Int Ed Engl 48(38), 7013-7016 (2009).
Devaraj, et al., "Tetrazine-Based Cycloadditions: Application to Pretargeted Live Cell Imaging", Bioconjug Chem 19(12), 2297-2299 (2008).
Karver, et al., "Bioorthogonal Reaction Pairs Enable Simultaneous, Selective, Multi-Target Imaging", Angew Chem Int Ed 51, 920-922 (2012).
Kolb, et al., "Click Chemistry: Diverse Chemical Function from a Few Good Reactions", Angew Chem Int Ed 40, 2004-2021 (2001).
Lang, et al., "Genetic Encoding of Bicyclononynes and trans-Cyclooctenes for Site-Specific Protein Labeling in Vitro and in Live Mammalian Cells via Rapid Fluorogenic Diels-Alder Reactions", J Am Chem Soc 134, 10317-10320 (2012).
Liang et al., "Control and Design of Mutual Orthogonality in Bioorthogonal Cycloadditions", J Am Chem Soc 134, 17904-17907 (2012).
Lukinavicius, et al., "A near-infrared fluorophore for live-cell super-resolution microscopy of cellular proteins", Nature Chemistry vol. 5, 132-137 (2013).
Merrifield, et al., "Solid Phase Peptide Synthesis. I. the Synthesis of a Tetrapeptide", JACS 85, 2149-2154 (1963).
Neef, et al., "Selective Fluorescence Labeling of Lipids in Living Cells", Angew Chem Int Ed 48, 1498-1500 (2009).
Neumann, et al., "Genetically encoding Nε-acetyllysine in recombinant proteins", Nature Chemical Biology vol. 4(4), 232-234 (2008).
Nguyen, et al., "Genetic Encoding and Labeling of Aliphatic Azides and Alkynes in Recombinant Proteins via a Pyrrolysyl-tRNA Synthetase/tRNA CUA Pair and Click Chemistry", J Am Chem Soc 131, 870-8721 (2009).
Nikic, et al., "Minimal Tags for Rapid Dual-Color Live-Cell Labeling and Super-Resolution Microscopy", Angew Chem Int Ed 53, 2245-2249 (2014).
Patent Cooperation Treaty, International Searching Authority, Search Report for PCT/EP2015/050555, 5 pages, dated Apr. 30, 2015.
Plass, et al., "Amino Acids for Diels-Alder Reactions in Living Cells", Angew Chem Int Ed 51, 4166-4170 (2012).
Plass, et al., "Genetically Encoded Copper-Free Click Chemistry", Angew Chem Int Ed 50, 3878-3881 (2011).
Schneider, et al., "Structural Insights into Incorporation of Norbornene Amino Acids for Click Modification of Proteins", ChemBioChem 14, 2114-2118 (2013).
Seckute, et al., "Expanding room for tetrazine ligations in the in vivo chemistry toolbox", Current Opinion in Chemica Biology 17, 761-767 (2013).
Summerer, et al., "A genetically encoded fluorescent amino acid", PNAS vol. 103(26), 9785-9789 (2006).
Wu, et al., "Catalyst-Free and Site-Specific One-Pot Dual-Labeling of a Protein Directed by Two Genetically Incorporated Noncanonical Amino Acids", ChemBioChem 13, 1405-1408 (2012).
Xiao, et al., "Genetic Incorporation of Multiple Unnatural Amino Acids into Proteins in Mammalian Cells", Angew Chem Int Ed 52, 14080-14083 (2013).
Yanagisawa, et al., "Multistep Engineering of Pyrrolysyl-tRNA Synthetase to Genetically Encode Nε-(p-Azidobenzyloxycarbonyl) lysine for Site-Specific Protein Modification", Chemistry and Biology 15, 1187-1197 (2008).
Kurra, et al., "Two Rapid Catalyst-Free Click Reactions for In Vivo Protein Labeling of Genetically Encoded Strained Alkene/Alkyne Functionalities", Bioconjugate Chem 25, 1730-1738 (2014).
Nikic, et al., "Minimal Tags for Rapid Dual-Color Live-Cell Labeling and Super-Resolution Microscopy", Angewandte Chemie International Edition 53(8), 1 page, Abstract (First published Jan. 28, 2014).
Ohta, et al., "Polymerization of a-Hydroxy Acids by Ribosomes", ChemBioChem 9, 2773-2778 (2008).

\* cited by examiner

7 (H-Tet-Atto532)

8 (Me-Tet-Cy3)

5 H-Tet-Cy5

6 Me-Tet-Cy5

9 (azide-Cy3)

10 Me-Tet-NH$_2$ c d a b

SEQUENCE LISTING

```
<160> NUMBER OF SEQ ID NOS: 3

<210> SEQ ID NO 1
<211> LENGTH: 454
<212> TYPE: PRT
<213> ORGANISM: M. mazei

<400> SEQUENCE: 1

Met Asp Lys Lys Pro Leu Asn Thr Leu Ile Ser Ala Thr Gly Leu Trp
1               5                   10                  15
```

```
Met Ser Arg Thr Gly Thr Ile His Lys Ile His His Glu Val Ser
             20                  25                  30

Arg Ser Lys Ile Tyr Ile Glu Met Ala Cys Gly Asp His Leu Val Val
         35                  40                  45

Asn Asn Ser Arg Ser Ser Arg Thr Ala Arg Ala Leu Arg His His Lys
 50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
             85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
            115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430
```

Asp Phe Lys Asn Ile Lys Arg Ala Ala Arg Ser Glu Ser Tyr Tyr Asn
            435                 440                 445

Gly Ile Ser Thr Asn Leu
        450

<210> SEQ ID NO 2
<211> LENGTH: 454
<212> TYPE: PRT
<213> ORGANISM: Artificial Sequence
<220> FEATURE:
<223> OTHER INFORMATION: mutant M. mazei pyrrolysyl tRNA synthetase

<400> SEQUENCE: 2

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Ala Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

```
Glu His Leu Glu Glu Phe Thr Met Leu Asn Phe Cys Gln Met Gly Ser
            340                 345                 350
Gly Cys Thr Arg Glu Asn Leu Glu Ser Ile Ile Thr Asp Phe Leu Asn
        355                 360                 365
His Leu Gly Ile Asp Phe Lys Ile Val Gly Asp Ser Cys Met Val Phe
    370                 375                 380
Gly Asp Thr Leu Asp Val Met His Gly Asp Leu Glu Leu Ser Ser Ala
385                 390                 395                 400
Val Val Gly Pro Ile Pro Leu Asp Arg Glu Trp Gly Ile Asp Lys Pro
                405                 410                 415
Trp Ile Gly Ala Gly Phe Gly Leu Glu Arg Leu Leu Lys Val Lys His
                420                 425                 430
Asp Phe Lys Asn Ile Lys Arg Ala Ala Arg Ser Glu Ser Tyr Tyr Asn
            435                 440                 445
Gly Ile Ser Thr Asn Leu
    450

<210> SEQ ID NO 3
<211> LENGTH: 19
<212> TYPE: PRT
<213> ORGANISM: Artificial Sequence
<220> FEATURE:
<223> OTHER INFORMATION: Partial peptide sequence
<220> FEATURE:
<221> NAME/KEY: misc_feature
<222> LOCATION: (13)..(13)
<223> OTHER INFORMATION: Xaa is an unnatural amino acid

<400> SEQUENCE: 3

Phe Ser Val Ser Gly Glu Gly Glu Gly Asp Ala Thr Xaa Gly Lys Leu
1               5                   10                  15
Thr Leu Lys
```

TRANS-CYCLOOCTENE AMINO AND HYDROXY ACIDS AND THEIR USE IN MULTIPLE CYCLOADDITION REACTIONS FOR LABELING OF MOLECULES

RELATED APPLICATION(S)

This application claims priority to European Application Number 14151175.8 that was filed on Jan. 14, 2014.

FIELD OF THE INVENTION

The invention relates to methods for linking tetrazines with dienophiles to establish at least two linkages by sequentially performing at least two cycloaddition reactions. The methods in particular allow establishing multi-labeling strategies.

BACKGROUND OF THE INVENTION

The ability to visualize biomolecules within living specimen by engineered fluorescence tags has become a major tool in modern biotechnology, cell biology, and life science. Encoding fusion proteins with comparatively large autofluorescent proteins is currently the most widely applied technique. As synthetic dyes typically offer better photophysical properties than autofluorescent proteins, alternative strategies have been developed based on genetically encoding unique tags such as Halo- and SNAP-tags, which offer high specificity but are still fairly large in size. Small tags like multi-histidine or multi-cysteine motifs may be used to recognize smaller fluorophores, but within the cellular environment they frequently suffer from specificity issues as their basic recognition element is built from native amino acids side chains. Such drawbacks may be overcome by utilizing bioorthogonal chemistries that rely on attaching unnatural moieties under mild physiological conditions.

Powerful chemistries that proceed efficiently under physiological temperatures and in highly functionalized biological environments are the copper(I) catalyzed Huisgen type (3+2) cycloaddition between linear azides and alkynes, the copper-free 3+2 cycloaddition between linear azides and strained cycloalkynes, or the inverse electron-demand Diels-Alder (4+2) cycloaddition reaction between a strained dienophile such as trans-cyclooctene or norbornene and a 1,2,4,5-tetrazine, both forms of click chemistry (Blackman et al., J. Am. Chem. Soc. 2008, 130, 13518-13519; Kolb et al., Angew Chem Int Ed Engl 2001, 40:2004; Devaraj et al., Angew Chem Int Ed Engl 2009, 48:7013; Devaraj et al., Bioconjugate Chem 2008, 19:2297; Devaraj et al., Angew Chem Int Ed Engl 2010, 49:2869; WO 2010/119389 A2; WO 2010/051530 A2). The standard (3+2) cycloaddition between an alkyne and an azide requires a copper catalyst that is toxic to bacteria and mammalian cells, which strongly reduces biocompatibility of this type of click chemistry. This limitation has been overcome by Bertozzi and co-workers, who showed that the click reaction readily proceeds without the need for a cell-toxic catalyst when utilizing ring-strained alkynes as a substrate (Agard et al., J Am Chem Soc 2004, 126:15046; WO 2006/050262 A2). Since then copper-free click chemistry has found increasing applications in labeling biomolecules. Fluorescent dyes comprising cyclooctynyl groups were used to label carbohydrates and proteins comprising enzymatically attached azide moieties in vivo (Chang et al., Proc Natl Acad Sci USA 2010, 107:1821) and the labeling of cycloalkyne-modified phosphatidic acid with azido fluorophores is described in Neef and Schultz, Angew Chem Int Ed Engl 2009, 48:1498. No catalyst was required in these applications.

Among the expanding repertoire of chemistries, in vivo chemistry applications of inverse Diels-Alder cycloadditions between tetrazines and strained dienophiles are attracting significant interest, particularly from those interested in performing live cell and animal imaging. Tetrazine ligations benefit from rapid, tunable kinetics as well as the existence of fluorogenic probes. Biomedical applications of tetrazine cycloadditions have been widely described and the implementation of tetrazine ligations to nanomaterial diagnostics has been addressed. For all this, see, for instance, the review of Seckute and Devaraj, Current Opinion in Chemical Biology 2013, 17, 761-767, and the references cited therein. Moreover, novel tetrazines and methods of synthesizing them are being developed (see, for instance, WO 2013/152359 A1). More specifically, WO 2011/095336 A2 describes methods and kits for the post-synthetic modification of nucleic acids by inverse Diels-Alder reaction, and WO 2013/029801 A1 describes methods for multiple orthogonal labeling of oligonucleotides by simultaneously performing an inverse Diels-Alder reaction and a copper-catalyzed click reaction. WO 2011/112970 A2 provides compositions and methods using bioorthogonal inverse electron demand Diels-Alder cycloaddition reactions for rapid and specific coupling of organic compounds to quantum dots (QDs).

The translational modification of proteins by direct genetic encoding of fluorescent unnatural amino acids using an orthogonal tRNA/aminoacyl tRNA synthetase pair offers exquisite specificity, freedom of placement within the target protein and, if any, a minimal structural change. This approach was first successfully applied by Summerer et al. (Proc Natl Acad Sci USA 2006, 103:9785), who evolved a leucyl tRNA/synthetase pair from *Escherichia coli* to genetically encode the UAA dansylalanine into *Saccharomyces cerevisiae*. In response to the amber stop codon TAG, dansylalanine was readily incorporated by the host translational machinery. This approach has meanwhile been used to genetically encode several small dyes and other moieties of interest. For instance, engineered *Methanococcus jannaschii* tyrosyl tRNA$^{tyr}$/synthetase, *E. coli* leucyl tRNA$^{leu}$/synthetase as well as *Methanosarcina mazei* and *M. barkeri* pyrrolysine tRNA$^{pyl}$/synthetase pairs have been used to genetically encode azide moieties in polypeptides (Chin et al., J Am Chem Soc 2002, 124:9026; Chin et al., Science 2003, 301:964; Nguyen et al, J Am Chem Soc 2009, 131:8720, Yanagisawa et al., Chem Biol 2008, 15:1187; WO 2013/108044 A2; WO 2002/085923 A2; WO 2002/086075 A2; EP2192185 A1).

The power of super-resolution microscopy (SRM) techniques heavily depends on the characteristics of the fluorophores. Most organic dyes have better photophysical properties and are typically more than 20 fold smaller than widely used fluorescent proteins. With recent advances in amber suppression technology, it is now possible to direct small, popular and commercially available fluorophores into specific protein residues. By means of an orthogonal tRNA/aminoacyl tRNA synthetase pair (tRNA/RS) from *Methanosarcina mazei*, unnatural amino acids (UAAs) carrying strained alkyne and alkene side chains are genetically incorporated at positions encoded by an amber (TAG) STOP codon (A. Borrmann, S. Milles, T. Plass, J. Dommerholt, J. M. Verkade, M. Wiessler, C. Schultz, J. C. van Hest, F. L. van Delft, E. A. Lemke, *Chembiochem* 2012, 13, 2094-2099; T. Plass, S. Milles, C. Koehler, C. Schultz, E. A. Lemke,

*Angew Chem Int Ed Engl* 2011, 50, 3878-3881; T. Plass, S. Milles, C. Koehler, J. Szymanski, R. Mueller, M. Wiessler, C. Schultz, E. A. Lemke, *Angew Chem Int Ed Engl* 2012, 51, 4166-4170; K. Lang, L. Davis, S. Wallace, M. Mahesh, D. J. Cox, M. L. Blackman, J. M. Fox, J. W. Chin, *Journal of the American Chemical Society* 2012, 134, 10317-10320; S. Schneider, M. J. Gattner, M. Vrabel, V. Flugel, V. Lopez-Carrillo, S. Prill, T. Carell, *Chembiochem* 2013, 14, 2114-2118; WO 2012/104422). These modifications add only a few atoms to the amino acid side chain and can be placed freely within the protein, lowering the risk of functional impact. Subsequently, strained alkyne and alkene UAAs can undergo catalyst-free strain-promoted alkyne-azide cycloaddition (SPAAC) and [strain-promoted inverse electron-demand] 4+2 Diels-Alder cycloaddition (SPIEDAC) reactions with organic fluorophores carrying azide or tetrazine (Tet) functionalities, respectively. Both reactions are fully biocompatible. They are additionally orthogonal to each other, since azides only react with alkynes but not with alkenes (Y. Liang, J. L. Mackey, S. A. Lopez, F. Liu, K. N. Houk, *Journal of the American Chemical Society* 2012, 134, 17904-17907; M. R. Karver, R. Weissleder, S. A. Hilderbrand, *Angew Chem Int Ed Engl* 2011.).

While encoding a single UAA has become relatively straight-forward and incorporating more than one UAA has been described (US 2010/297693 A1; Han Xiao, et al., *Angew Chem Int Ed Engl* 2013, 52, 14080-14083) there is still a demand for robust and efficient multi-color labeling strategies in mammalian systems. At least two distinct strategies for UAA-based dual-color labeling and SRM are conceivable, which serve different experimental designs: i) Simultaneous incorporation of two different UAAs, harboring two orthogonal chemistries (e.g. SPAAC and SPIEDAC), recognizing each a different codon in a single protein (e.g. for Förster resonance energy transfer—FRET studies) or in two different proteins (e.g. for colocalization microscopy of two different molecules). ii) Sequential encoding of two different UAAs, harboring two orthogonal chemistries, in response to the same codon using a single tRNA/RS system. This can be done in a pulse-chase manner where the first UAA supplied to the growth medium is then chased by the second UAA. This can for example help to visualize protein sorting.

Despite large efforts, there is still a high demand for strategies to facilitate site-specific labeling of proteins in vitro and in vivo and robust multi-color labeling strategies in mammalian systems in particular. For practical reasons, it would be helpful if bioorthogonal coupling reactions proceeded with extremely rapid kinetics ($k > 10^2$ $M^{-1}$ $s^{-1}$) and high specificity. Improving kinetics would minimize both the time and amount of labeling agent required to maintain high coupling yields. Thus, it was an object of the present invention to design extremely rapid bioorthogonal coupling reactions between tetrazines and dienophiles which allow establishing multi-labeling strategies. More specifically, it was an object of the present invention to provide amino acids or analogues thereof that can be translationally incorporated in polypeptide chains and allow labeling of the resulting polypeptide in vitro and in vivo as well as establishing multi-labeling strategies.

SUMMARY OF THE INVENTION

The present invention relates to methods for forming linkages by cycloaddition reactions, wherein the method comprises reacting a first tetrazine with a first dienophile followed by reacting a second tetrazine with a second dienophile, wherein the reaction of the first tetrazine with the first dienophile proceeds in the presence of the second dienophile, wherein (i) the first tetrazine comprises a group of the formula:

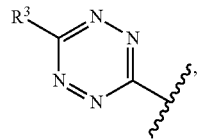

wherein
$R^3$ is $C_1$-$C_3$-alkyl;
(ii) the first dienophile comprises a trans-cyclooctenyl group of the formula:

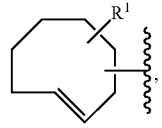

wherein
$R^1$ is hydrogen, halogen, $C_1$-$C_4$-alkyl, $(R^aO)_2P(O)O$—$C_1$-$C_4$-alkyl, $(R^bO)_2P(O)$—$C_1C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and
$R^a$, $R^b$ independently are hydrogen or $C_2$-$C_5$-alkanoyloxymethyl;
(iii) the second tetrazine comprises a group of the formula:

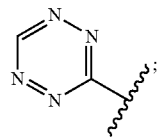 [SMILES: *c1nncnn1]

and
(iv) the second dienophile comprises a cyclooctynyl group of the formula:

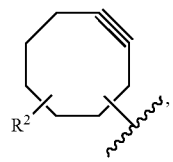

wherein
$R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and
$R^c$, $R^d$ independently are hydrogen or $C_2$-$C_5$-alkanoyloxymethyl.

Accordingly, in the method of the invention the first tetrazine reacts with the first dienophile comprising the trans-cyclooctenyl group, and the second tetrazine reacts with the second dienophile comprising the cyclooctynyl group. The rate constants of both reactions are high and yet the first reaction proceeds in the presence of the second dienophile without the first tetrazine substantially reacting with the second dienophile. Thus, the first tetrazine is reacted with first dienophile under conditions that do not allow the first tetrazine to substantially react with the second dienophile. To put it another way, the first tetrazine preferentially reacts with the first dienophile in the presence of the second dienophile. More specifically, the first tetrazine reacts specifically with the first dienophile in the presence of the second dienophile. Thus, the methods of the invention allow the formation of two different linkages at high rates and yet with high specificity by first providing a first and a second dienophile and then contacting the first and the second dienophile with a first tetrazine so as to react the first dienophile with the first tetrazine under conditions that do not allow the first tetrazine to substantially react with the second dienophile.

The kind of reactions performed according to the invention allow achieving rate constants k of 50 $M^{-1}$ $s^{-1}$ or higher, $1 \times 10^2$ $M^{-1}$ $s^{-1}$ or higher, or $2 \times 10^2$ $M^{-1}$ $s^{-1}$ or higher for both reactions.

According to one aspect of the invention, the first reaction (of the first tetrazine with the first dienophile) proceeds at rate constants k of $5 \times 10^2$ $M^{-1}$ $s^{-1}$ or higher, $1 \times 10^3$ $M^{-1}$ $s^{-1}$ or higher, or $2 \times 10^3$ $M^{-1}$ $s^{-1}$ or higher.

According to second aspect of the invention, the second reaction (of the second tetrazine with the second dienophile) proceeds at rate constants k of 50 $M^{-1}$ $s^{-1}$ or higher, $1 \times 10^2$ $M^{-1}$ $s^{-1}$ or higher, or $2 \times 10^2$ $M^{-1}$ $s^{-1}$ or higher.

According to one embodiment of the invention, the first and second reactions proceed at rate constants according to said first and second aspect.

For the first reaction (of the first tetrazine with the first dienophile) to expediently proceed in the presence of the second dienophile, the first reaction proceeds at higher rate constants than the reaction of the first tetrazine with the second dienophile. Accordingly, the rate constant k of the first reaction is usually at least 100-times higher than the rate constant k of the reaction of the first tetrazine with the second dienophile. Accordingly, the reaction of the first tetrazine with the second dienophile usually proceeds at rate constants k of 5 $M^{-1}$ $s^{-1}$ or lower, 2 $M^{-1}$ $s^{-1}$ or lower, or 1 $M^{-1}$ $s^{-1}$ or lower. It is preferred if the rate constant k of the first reaction is at least 200-times, 500-times, 1000-times, 5000-times, or 10000-times higher than the rate constant k of the reaction of the first tetrazine with the second dienophile. Accordingly, the reaction of the first tetrazine with the second dienophile preferably proceeds at rate constants k of 0.5 $M^{-1}$ $s^{-1}$ or lower, 0.1 $M^{-1}$ $s^{-1}$ or lower, 0.05 $M^{-1}$ $s^{-1}$ or lower, or 0.01 $M^{-1}$ $s^{-1}$ or lower.

Methods for determining reaction constants are well known in the art and the absolute reaction constants disclosed herein refer in particular to the determination described in example J herein.

Both reactions can be carried out at a wide range of temperatures. In biological systems, temperatures in the range of 4° C. to 45° C., e.g. in the range of 15° C. to 25° C. such as about 22° C., or in the range of 30° C. to 40° C. such as about 37° C., can be expediently used.

The first reaction is usually allowed to proceed for a time sufficient to allow substantially all trans-cyclooctenyl groups (the first dienophile) to react with the first tetrazine prior to performing the second reaction. Usually, reaction times of a few minutes, e.g. 60, 45 or 30 minutes or less, and in particular of 10 minutes or less are expedient for the first reaction to proceed expediently. Yet, the first reaction is allowed to proceed only in so far as there is substantially no reaction of the first tetrazine with the second dienophile (i.e. the cyclooctynyl groups). Usually, reaction times of less than 30 minutes, e.g. less than 25, 20 or 15 minutes, and in particular of less than 10 minutes, are expedient for the first reaction to proceed with substantially no second dienophile reacting with the first tetrazine.

The second reaction is usually allowed to proceed for a time sufficient to allow substantially all cyclooctynyl groups (the second dienophile) to react with the second tetrazine. Usually, reaction times of 2 hours or less, e.g. 1 hour or less, 45 minutes or less, or 30 minutes or less, and in particular of 20 minutes or less are expedient for the second reaction to proceed to completeness. Because the second reaction is usually performed only once substantially all trans-cyclooctenyl groups (the first dienophile) have reacted with the first tetrazine, the reaction times of the second reaction do not have to take a further potentially competing cycloaddition reaction into account. However, it is usually expedient if the second reaction is allowed to proceed for less than 1 hour, e.g. less than 50, 40 or 30 minutes, and in particular for less than 20 minutes.

The reaction times disclosed herein apply in particular to the reaction temperatures disclosed herein, in particular to reactions carried out at ambient temperature, such as about 37° C.

If the first or the second reaction does not run to completeness, it is possible to react any remaining first or second dienophile in an appropriate manner to convert these groups to a form which is no longer reactive with the first or second tetrazine. This is in particular expedient for the first reaction to be completed, thereby preventing remaining first dienophile to react with the second tetrazine. For instance, if the first reaction does not run to completeness, with some unreacted trans-cyclooctenyl groups (the first dienophile) remaining, these groups can be reacted with further first tetrazine (quencher), wherein the further first tetrazine comprises a group of the formula:

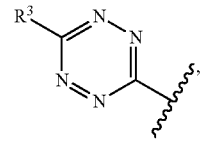

but is different from the first tetrazine initially used. For instance, if the first tetrazine initially used comprises a label, a corresponding tetrazine without label can be used as the further first tetrazine. For instance, the quencher may a compound of the formula:

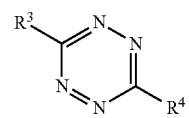

or an acid addition salt thereof, wherein
$R^3$ is $C_1$-$C_3$-alkyl; and
$R^4$ is an organic radical (such as a benzyl group) which is different from the moiety at the corresponding position in the first tetrazine initially used.

According to one embodiment, the quencher is (4-(6-methyl-1,2,4,5-tetrazine-3-yl)phenyl)methanamine or an acid addition salt thereof.

Proceeding in this way can be advantageous in situations where having the first reaction proceed to completeness is associated with disadvantages (because a relatively high amount of the first tetrazine would have to be used or expedient reaction times do not allow the reaction to proceed to completeness) and the use the further first tetrazine is associated with advantages (because it helps to keep the amount of the first tetrazine to be used relatively low while allowing the reaction to proceed to completeness within expedient reaction times). For instance, while it may be disadvantageous to use an excessively high amount of the first tetrazine (e.g., because it is expensive), the further first tetrazine may not have the same disadvantages and thus can be used in relatively high amounts to complete the reaction within expedient reaction times). Thus, allowing substantially all trans-cyclooctenyl groups (the first dienophile) to react with the first tetrazine is meant to denote that at least 95, e.g. at least 96, 97, 98 or 99% of the trans-cyclooctenyl groups initially present have reacted with the first tetrazine, while the remaining trans-cyclooctenyl groups can optionally be reacted with a further first tetrazine so as to have all trans-cyclooctenyl groups (i.e. at least 99.9% of the trans-cyclooctenyl groups initially present) reacted with the (further) first tetrazine.

It may be expedient to remove unreacted first tetrazine prior to performing the second reaction. This can be done in a manner know per se. Likewise, it may be expedient to remove unreacted further first tetrazine (quencher) prior to performing the second reaction. This, too, can be done in a manner know per se.

According to a particular aspect of the invention, the first tetrazine comprises a group of the formula:

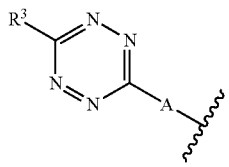

wherein $R^3$ is $C_1$-$C_3$-alkyl and A is 1,4-phenylene or $C_1$-$C_6$-alkylene.

According to a further particular aspect of the invention, the second tetrazine comprises a group of the formula:

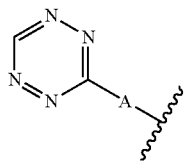

wherein A is 1,4-phenylene or $C_1$-$C_6$-alkylene.

A is a group or part of a group that links the tetrazine to a further moiety, e.g. a label. A can be the same group in the first and the second tetrazine, or A of the first tetrazine can be different from A of the second tetrazine. In particular, A is 1,4-phenylene.

Thus, according to a particular embodiment of the invention, the first tetrazine comprises a group of the formula:

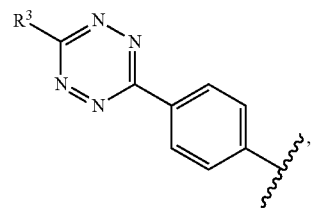

wherein $R^3$ is $C_1$-$C_3$-alkyl.

Likewise, according to a particular embodiment of the invention, the second tetrazine comprises a group of the formula:

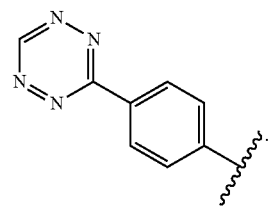 [SMILES: *c1ccc(-c2nncnn2)cc1]

Because the first tetrazine carries the substituent $R^3$, the reactivity of the first tetrazine with the first dienophile is sufficiently different from the reactivity of the first tetrazine with the second dienophile. Accordingly, $R^3$ is selected so as to provide for sufficiently different reactivities. According to the invention, $R^3$ is preferably methyl or ethyl. In particular, methyl is preferred.

The point of attachment of the trans-cyclooctenyl or cyclooctynyl group may be by a ring atom in α-, β- or γ-position relative to the double or triple bond.

According to a particular embodiment, the trans-cyclooctenyl or cyclooctynyl group is attached by the ring atom in a-position relative to the double or triple bond.

Thus, according to a particular aspect of the invention, the first dienophile comprises a trans-cyclooctenyl group of the formula:

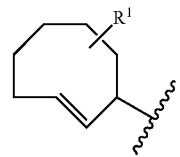

wherein $R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^a$, $R^b$ independently are hydrogen or $C_2$-$C_5$-alkanoyloxymethyl.

According to a further particular aspect of the invention, the second dienophile comprises a cyclooctynyl group of the formula:

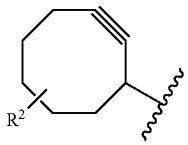

wherein
R² is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^c$, $R^d$ independently are hydrogen or $C_2$-$C_5$-alkanoyloxymethyl.

The trans-cyclooctenyl or cyclooctynyl group may be unsubstituted (i.e., R¹ and R² are hydrogen) or substituted with one or more than one radical R¹ or R², respectively. Thus, there may be one or more than one substituent R¹ and/or R². More particularly, there may be up to 5, e.g. 1, 2 or 3, substituents R¹. Likewise, there may be up to 5, e.g. 1, 2 or 3, substituents R². The trans-cyclooctenyl or cyclooctynyl groups of the invention may thus be depicted as follows:

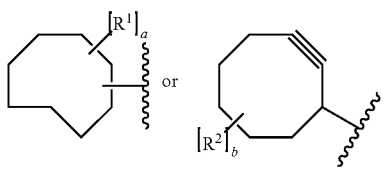

wherein a is zero, 1, 2, 3, 4 or 5, and b is zero, 1, 2, 3, 4 or 5.

If there is more than one radical R¹, these may be the same or different radicals and two radicals R¹ may be bound to the same or different atoms. Likewise, if there is more than one radical R², these may be the same or different radicals and two radicals R² may be bound to the same or different atoms. For example, R¹ and/or R² may be two fluorine atoms bound to one carbon ring atom.

R¹ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino, with $R^a$ and $R^b$ independently being hydrogen or $C_2$-$C_5$-alkanoyloxymethyl.

According to a particular embodiment, R¹ is hydrogen.

R² is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino with $R^c$ and $R^d$ independently being hydrogen or $C_2$-$C_5$-alkanoyloxymethyl.

According to a particular embodiment, R² is hydrogen.
According to a further particular embodiment, R¹ is hydrogen and R² is hydrogen.

According to a further particular embodiment of the invention, the trans-cyclooctenyl group has the formula:

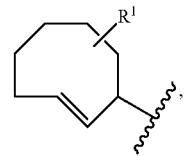

wherein
R¹ is hydrogen; and
the first tetrazine comprises a group of the formula:

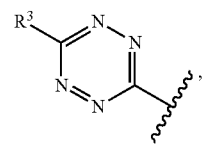

wherein
R³ is methyl.

According to a further particular embodiment of the invention, the cyclooctynyl group has the formula:

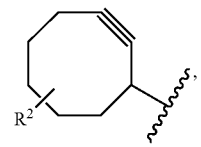

wherein
R¹ is hydrogen; and
the second tetrazine comprises a group of the formula:

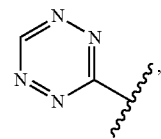

Thus, the present invention in particular relates to methods for forming linkages by cycloaddition reactions, wherein the method comprises reacting a first tetrazine with a first dienophile followed by reacting a second tetrazine with a second dienophile, wherein the reaction of the first tetrazine with the first dienophile proceeds in the presence of the second dienophile, wherein
(i) the first tetrazine comprises a group of the formula:

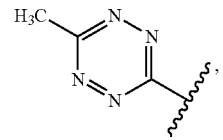 [SMILES: *c1nnc(C)nn1]

(ii) the first dienophile comprises a trans-cyclooctenyl group of the formula:

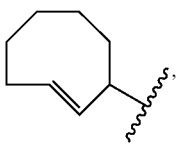 [SMILES: *C1/C=C/CCCCC1]

(iii) the second tetrazine comprises a group of the formula:

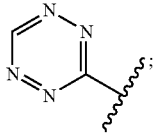

and (iv) the second dienophile comprises a cyclooctynyl group of the formula:

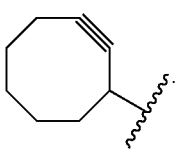

The present invention also relates to kits which can be used in carrying out the methods of the invention.

Particular kits of the invention include:

(i) a first tetrazine comprising a group of the formula:

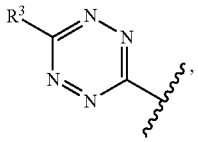

wherein $R^3$ is $C_1$-$C_3$-alkyl; and (ii) a second tetrazine, comprising a group of the formula:

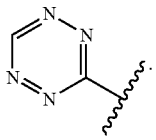 [SMILES: *c1nncnn1]

Said first and second tetrazines are in particular agents which can be used to label target molecules or target molecule compositions and are therefore referred to herein also as labeling agents. These include in particular the labeling agents as disclosed herein.

Further particular kits of the invention include:

(i) a first agent comprising a trans-cyclooctenyl group of the formula:

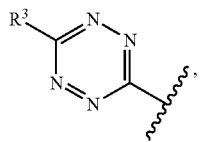

wherein $R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, $CN$, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^a$, $R^b$ independently are hydrogen or $C_2$-$C_5$-alkanoyloxymethyl; and (ii) a second agent comprising a cyclooctynyl group of the formula:

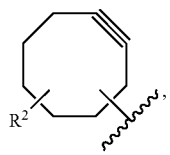

wherein $R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, $CN$, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino;

$R^c$, $R^d$ independently are hydrogen or $C_2$-$C_5$-alkanoyloxymethyl.

Said first and second agents are in particular agents which can be used to modify target molecules or target molecule compositions and are therefore referred to herein also as modifying agents. These include in particular the unnatural amino acids and their analogues as disclosed herein.

Further, kits of the invention may include the first and the second tetrazine as disclosed herein as well as the first agent comprising a trans-cyclooctenyl group and the second agent comprising a cyclooctynyl group.

The methods of the invention are especially suitable for linking a large variety of molecules with one another or ligated to one another. For example, among these molecules there are polypeptides, oligonucleotides, glycans, lipids, dyes, therapeutic agents, diagnostic agents, chelating/complexing agents, solid phase surfaces, nanoparticles, quantum dots.

The methods of the invention are especially suitable for multiple, i.e. at least dual, labeling of molecules by sequentially linking the first tetrazine to the first dienophile followed by linking the second tetrazine to the second dienophile. Accordingly, the first tetrazine is a first labeling agent and the second tetrazine is a second labeling agent.

Thus, the present invention relates to methods for labeling molecules, the method comprising contacting a target molecule or a target molecule composition with (i) a first labeling agent comprising a group of the formula:

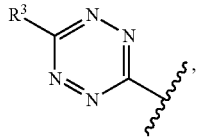

wherein
R³ is C₁-C₃-alkyl; followed by
(ii) a second labeling agent comprising a group of the formula:

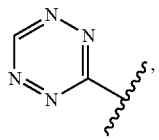 [SMILES: *c1nncnn1]

wherein the target molecule comprises
(i) a trans-cyclooctenyl group of the formula:

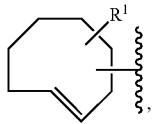

wherein
R¹ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and
$R^a$, $R^b$ independently are hydrogen or $C_2$-$C_5$-alkanoyloxymethyl; and
(ii) a cyclooctynyl group of the formula:

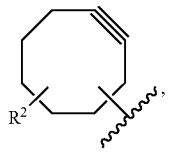

wherein
R² is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and
$R^c$, $R^d$ independently are hydrogen or $C_2$-$C_5$-alkanoyloxymethyl,
wherein the target molecule composition comprises
(i) a first target molecule comprising a trans-cyclooctenyl group of the formula:

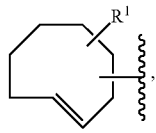

wherein
R¹ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and
$R^a$, $R^b$ independently are hydrogen or $C_2$-$C_5$-alkanoyloxymethyl; and
(ii) a second target molecule comprising a cyclooctynyl group of the formula:

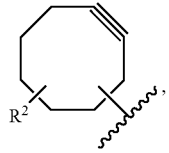

wherein
R² is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and
$R^c$, $R^d$ independently are hydrogen or $C_2$-$C_5$-alkanoyloxymethyl.

The labeling agents of the invention can comprise any label, provided that the label of the first labeling agent is different from the label of the second labeling agent. Labels of the invention include, but are not limited to, dyes (e.g. fluorescent, luminescent, or phosphorescent dyes, such as dansyl, coumarin, fluorescein, acridine, rhodamine, silicon-rhodamine, BODIPY, or cyanine dyes), chromophores (e.g., phytochrome, phycobilin, bilirubin, etc.), radiolabels (e.g. radioactive forms of hydrogen, fluorine, carbon, phosphorous, sulphur, or iodine, such as tritium, fluorine-18, carbon-11, carbon-14, phosphorous-32, phosphorous-33, sulphur-33, sulphur-35, iodine-123, or iodine-125), MRI-sensitive spin labels, affinity tags (e.g. biotin, His-tag, Flag-tag, strep-tag, sugars, lipids, sterols, PEG-linkers, benzylguanines, benzylcytosines, or co-factors), polyethylene glycol groups (e.g., a branched PEG, a linear PEG, PEGs of different molecular weights, etc.), photocrosslinkers (such as p-azidoiodoacetanilide), NMR probes, X-ray probes, pH probes, IR probes, resins, solid supports and bioactive compounds (e.g. synthetic drugs).

In some embodiments, dyes can include an NIR contrast agent that fluoresces in the near infrared region of the spectrum. Exemplary near-infrared fluorophores can include dyes and other fluorophores with emission wavelengths (e.g., peak emission wavelengths) between about 630 and 1000 nm, e.g., between about 630 and 800 nm, between about 800 and 900 nm, between about 900 and 1000 nm, between about 680 and 750 nm, between about 750 and 800 nm, between about 800 and 850 nm, between about 850 and 900 nm, between about 900 and 950 nm, or between about 950 and 1000 nm. Fluorophores with emission wavelengths (e.g., peak emission wavelengths) greater than 1000 nm can also be used in the methods described herein.

Fluorophores useful in the present methods include without limitation: 7-amino-4-methylcoumarin-3-acetic acid (AMCA), TEXAS RED™ (Molecular Probes, Inc., Eugene, Oreg.), 5-(and -6)-carboxy-X-rhodamine, lissamine rhodamine B, 5-(and -6)-carboxyfluorescein, fluorescein-5-isothiocyanate (FITC), 7-diethylaminocoumarin-3-carboxylic acid, tetramethylrhodamine-5-(and -6)-isothiocyanate, 5-(and -6)-carboxytetramethylrhodamine, 7-hydroxycoumarin-3-carboxylic acid, 6-[fluorescein 5-(and -6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and CASCADE™ blue acetylazide (Molecular Probes, Inc., Eugene, Oreg.) and ATTO dyes.

Bioactive compounds that can be attached to a polypeptide of the invention include, but are not limited to, cytotoxic compounds (e.g., cancer chemotherapeutic compounds); antiviral compounds; biological response modifiers (e.g., hormones, chemokines, cytokines, interleukins, etc.); microtubule affecting agents; hormone modulators; steroidal compounds; and the like.

A target molecule of the invention may be any molecule which is to be labeled. Target molecules of the invention include, but are not limited to, polypeptides, oligonucleotides, glycans, and lipids.

The methods of the invention can be used to label the same target molecule (e.g., a polypeptide) so that the target molecule comprises both first and second labels, or two different target molecules can be labeled so that a first target molecule comprises the first label and a second target molecule comprises the second label. If two different target molecules are labeled, the target molecules can be of the same kind (e.g. two polypeptides) or of different kinds (e.g. a polypeptide and an oligonucleotide). Labeling two different target molecules of the same kind (e.g. two polypeptides) includes labeling two populations of the same polypeptide which are essentially identical but for the dienophile. Such polypeptides can be obtained in a variety of ways, for instance by incorporating the first and the second dienophile into different populations of the polypeptide at different time points.

Thus, according to one embodiment of the invention, the trans-cyclooctenyl group is linked to an amino acid residue of a target polypeptide, and the cyclooctynyl group is linked to an amino acid residue of a target polypeptide. According to a particular embodiment of the invention, the trans-cyclooctenyl group and the cyclooctynyl group are linked to amino acid residues of a target polypeptide, wherein the amino acid residue to which the trans-cyclooctenyl group is linked is usually different from the amino acid residue to which the cyclooctynyl group is linked. According to a further particular embodiment of the invention, the trans-cyclooctenyl group is linked to an amino acid residue of a first target polypeptide and the cyclooctynyl group is linked to an amino acid residue of a second target polypeptide.

If a first and a second target molecule are to be labeled, both form part of the composition which is subjected to the labeling reactions. Compositions of the invention include biological systems, such as organisms or biological samples. According to one embodiment of the invention, the biological sample comprises a cell.

Thus, the present invention also relates to biological systems, e.g. organisms or biological samples, and in particular cells, comprising
(i) a trans-cyclooctenyl group of the formula:

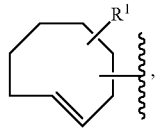

wherein
$R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl) amino, $C_2$-$C_5$-alkenylamino, $C_2$-$C_5$-alkenyl-$C_1$-$C_4$-alkyl-amino or Di-($C_2$-$C_5$-alkenyl)amino; and
$R^a$, $R^b$ independently are hydrogen or $C_2$-$C_5$-alkanoyloxymethyl;
and
(ii) a cyclooctynyl group of the formula:

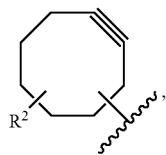

wherein
$R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl) amino, $C_2$-$C_5$-alkenylamino, $C_2$-$C_5$-alkenyl-$C_1$-$C_4$-alkyl-amino or Di-($C_2$-$C_5$-alkenyl)amino; and
$R^c$, $R^d$ independently are hydrogen or $C_2$-$C_5$-alkanoyloxymethyl.

Organisms of the invention include all types of organisms, such as prokaryotes and eukaryotes. Accordingly, cells of the invention include all types of cells, such as prokaryotic or eukaryotic cells. According to one embodiment of the invention is a eukaryotic cell, e.g. a mammalian cell.

According to one aspect of the invention, the trans-cyclooctenyl and cyclooctynyl groups can be attached to any component of the biological system, e.g., cell component, such as polypeptides, oligonucleotides, glycans, and lipids. Accordingly, particular embodiments of the invention include the trans-cyclooctenyl group being attached to a polypeptide and the cyclooctynyl group being attached to a polypeptide, wherein the trans-cyclooctenyl group and the cyclooctynyl group are attached to the same polypeptide, or the trans-cyclooctenyl group is attached to a first polypeptide and the cyclooctynyl group is attached to a second polypeptide, the first and the second polypeptide being different polypeptides.

According to a particular embodiment, a cell of the invention is prepared by a method which comprises
a) providing a cell comprising:
(i) a first aminoacyl tRNA synthetase, or a polynucleotide encoding it; and optionally a second aminoacyl tRNA synthetase, or a polynucleotide encoding it;

(ii) a first tRNA having an anticodon to a first selector codon, or a polynucleotide encoding said tRNA; and optionally a second tRNA having an anticodon to a second selector codon, or a polynucleotide encoding said tRNA; and (iii) a polynucleotide encoding a target polypeptide and comprising one or more than one first and second selector codon(s); or a first polynucleotide encoding a first target polypeptide and comprising one or more than one first selector codon(s) and a second polynucleotide encoding a second target polypeptide and comprising one or more than one second selector codon(s), wherein said first aminoacyl tRNA synthetase (i) is capable of acylating the first tRNA (ii) with a first unnatural amino acid or an analogue thereof comprising a trans-cyclooctenyl group of the formula:

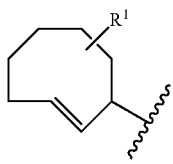

wherein $R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^a$, $R^b$ independently are hydrogen or $C_2$-$C_5$-alkanoyloxymethyl, and with a second unnatural amino acid or an analogue thereof comprising a cyclooctynyl group of the formula:

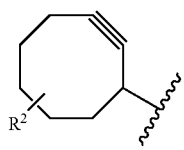

wherein $R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^c$, $R^d$ independently are hydrogen or $C_2$-$C_5$-alkanoyloxymethyl;

or wherein said first aminoacyl tRNA synthetase (i) is capable of acylating the first tRNA (ii) with a first unnatural amino acid or an analogue thereof comprising a trans-cyclooctenyl group of the formula:

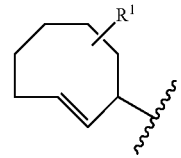

wherein $R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^a$, $R^b$ independently are hydrogen or $C_2$-$C_5$-alkanoyloxymethyl, and said second aminoacyl tRNA synthetase (i) is capable of acylating the second tRNA (ii) with a second unnatural amino acid or an analogue thereof comprising a cyclooctynyl group of the formula:

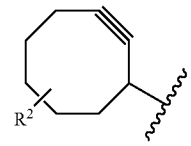

wherein $R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^c$, $R^d$ independently are hydrogen or $C_2$-$C_5$-alkanoyloxymethyl;

b) contacting the cell with the first and the second amino acid or an analogue thereof; and c) allowing translation of the polynucleotide(s) (iii) thereby incorporating the first and the second unnatural amino acids or the analogues thereof into the target polypeptide(s) at the position(s) encoded by the selector codon(s).

According to one embodiment of the invention, the cell is contacted with the first and the second unnatural amino acids or the analogues thereof sequentially. Accordingly, the method of the invention comprises:

a) contacting the cell with the first unnatural amino acid or the analogue thereof; and b) allowing translation of the polynucleotide (iii) thereby incorporating the first unnatural amino acid or the analogue thereof into the target polypeptide at the position(s) encoded by the selector codon(s);

c) contacting the cell with the second unnatural amino acid or the analogue thereof; and d) allowing translation of the polynucleotide (iii) thereby incorporating the second unnatural amino acid or the analogue thereof into the target polypeptide at the position(s) encoded by the selector codon(s).

In this embodiment, a single aminoacyl tRNA synthetase/tRNA pair can be used to incorporate the first and the second unnatural amino acid or the analogue thereof into different populations of a polypeptide at different time points.

According to one aspect of the invention, the first unnatural amino acid or the analogue thereof is a compound of the formula:

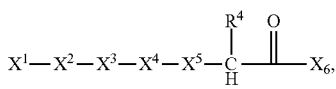

wherein:
$X^1$ has the formula:

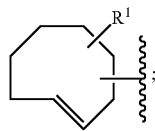

$R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino;

$R^a$, $R^b$ independently are hydrogen or $C_2$-$C_5$-alkanoyloxymethyl;

$X^2$ is —$CH_2$—, —O—, —S—, —NH—, —C(O)—, —OC(O)—, —C(O)O—, —NH—C(O)— or —C(O)—NH—;

$X^3$ is $C_1$-$C_6$-alkylene, —($CH_2$—$CH_2$—O)$_m$—, —($CH_2$-O)$_p$— or a single bond;

$X^4$ is —NH—, —C(O)—NH—, —NH—C(O)—, —NH—CH($NH_2$)—, —CH($NH_2$)—NH—, —NH—C(NH)—NH—, —C(O)—NH—CH($NH_2$)—, —C(O)—NH—C(NH)—NH—, NH—CH($NH_2$)—C(O)— or —NH—C(NH)—NH—C(O)—;

$X^5$ is —($CH_2$)$_n$— or phenylene-$CH_2$—;

$X^6$ is hydrogen, $C_1$-$C_6$-alkyl, $C_1$-$C_6$-alkoxy-$C_1$-$C_2$-alkyl, $C_2$-$C_7$-alkanoyloxy-$C_1$-$C_2$-alkyl or $C_2$-$C_7$-alkanoylsulfanyl-$C_1$-$C_2$-alkyl;

$R^4$ is —OH or —$NH_2$;

n is an integer from 1 to 4;

m is an integer from 1 to 6; and p is an integer from 1 to 6, or an acid or base addition salt thereof.

According to a further aspect of the invention, the second unnatural amino acid or the analogue thereof is a compound of the formula:

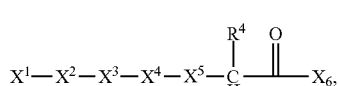

wherein:
$X^1$ has the formula:

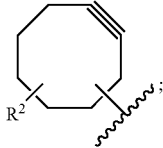

$R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkylamino or Di-($C_2$-$C_5$-alkenyl)amino;

$R^c$, $R^d$ independently are hydrogen or $C_2$-$C_5$-alkanoyloxymethyl;

$X^2$ is —$CH_2$—, —O—, —S—, —NH—, —C(O)—, —OC(O)—, —C(O)O—, —NH—C(O)— or —C(O)—NH—;

$X^3$ is $C_1$-$C_6$-alkylene, —($CH_2$-$CH_2$—O)$_m$—, —($CH_2$—O)$_p$— or a single bond;

$X^4$ is —NH—, —C(O)—NH—, —NH—C(O)—, —NH—CH($NH_2$)—, —CH($NH_2$)—NH—, —NH—C(NH)—NH—, —C(O)—NH—CH($NH_2$)—, —C(O)—NH—C(NH)—NH—, NH—CH($NH_2$)—C(O)— or —NH—C(NH)—NH—C(O)—;

$X^5$ is —($CH_2$)$_n$— or phenylene-($CH_2$)$_n$—;

$X^6$ is hydrogen, $C_1$-$C_6$-alkyl, $C_1$-$C_6$-alkoxy-$C_1$-$C_2$-alkyl, $C_2$-$C_7$-alkanoyloxy-$C_1$-$C_2$-alkyl or $C_2$-$C_7$-alkanoylsulfanyl-$C_1$-$C_2$-alkyl;

$R^4$ is —OH or —$NH_2$;

n is an integer from 1 to 4;

m is an integer from 1 to 6; and p is an integer from 1 to 6, or an acid or base addition salt thereof.

The present invention further relates to polypeptides comprising
(i) a trans-cyclooctenyl group of the formula:

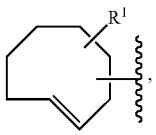

wherein
$R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^a$, $R^b$ independently are hydrogen or $C_2$-$C_5$-alkanoyloxymethyl;

and
(ii) a cyclooctynyl group of the formula:

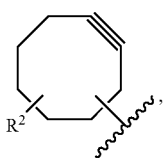

wherein
R² is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^c$, $R^d$ independently are hydrogen or $C_2$-$C_5$-alkanoyloxymethyl.

According to one aspect of the invention, the polypeptides comprise a residue of the formula:

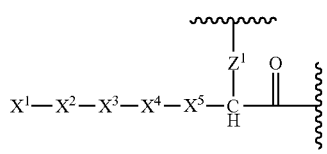

wherein:
X¹ has the formula

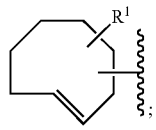

R¹ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino;

$R^a$, $R^b$ independently are hydrogen or $C_2$-$C_5$-alkanoyloxymethyl;

X² is —$CH_2$—, —O—, —S—, —NH—, —C(O)—, —OC(O)—, —C(O)O—, —NH—C(O)— or —C(O)—NH—;

X³ is $C_1$-$C_6$-alkylene, —($CH_2$-$CH_2$—O)$_m$—, —($CH_2$—O)$_p$— or a single bond;

X⁴ is —NH—, —C(O)—NH—, —NH—C(O)—, —NH—CH($NH_2$)—, —CH($NH_2$)—NH—, —NH—C(NH)—NH—, —C(O)—NH—CH($NH_2$)—, —C(O)—NH—C(NH)—NH—, NH—CH($NH_2$)—C(O)— or —NH—C(NH)—NH—C(O)—;

X⁵ is —($CH_2$)$_n$— or phenylene-$CH_2$—;

Z¹ is —O— or NH—;

n is an integer from 1 to 4;

m is an integer from 1 to 6; and p is an integer from 1 to 6, and a residue of the formula:

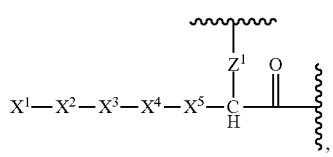

wherein:
X¹ has the formula:

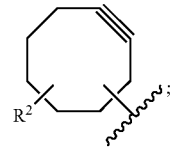

R² is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$alkyl-amino or Di-($C_2$-$C_5$-alkenyl)amino;

$R^c$, $R^d$ independently are hydrogen or $C_2$-$C_5$-alkanoyloxymethyl;

X² is —$CH_2$—, —O—, —S—, —NH—, —C(O)—, —OC(O)—, —C(O)O—, —NH—C(O)— or —C(O)—NH—;

X³ is $C_1$-$C_6$-alkylene, —($CH_2$—$CH_2$—O)$_m$—, —($CH_2$—O)$_p$— or a single bond;

X⁴ is —NH—, —C(O)—NH—, —NH—C(O)—, —NH—CH($NH_2$)—, —CH($NH_2$)—NH—, —NH—C(NH)—NH—, —C(O)—NH—CH($NH_2$)—, —C(O)—NH—C(NH)—NH—, NH—CH($NH_2$)—C(O)— or —NH—C(NH)—NH—C(O)—;

X⁵ is —($CH_2$)$_n$— or phenylene-$CH_2$—;

Z¹ is —O— or NH—;

n is an integer from 1 to 4;

m is an integer from 1 to 6; and p is an integer from 1 to 6.

Further, the present invention also relates to method for preparing the polypeptide of the invention, the method comprising:

a) providing a translation system comprising:
(i) a first aminoacyl tRNA synthetase, or a polynucleotide encoding it; and optionally a second aminoacyl tRNA synthetase, or a polynucleotide encoding it;
(ii) a first and a second unnatural amino acid or an analogue thereof;
(iii) a first tRNA having an anticodon to a first selector codon, or a polynucleotide encoding said tRNA; and optionally a second tRNA having an anticodon to a second selector codon, or a polynucleotide encoding said tRNA; and
(iv) a polynucleotide encoding a target polypeptide and comprising one or more than one first and second selector codon(s), wherein said first aminoacyl tRNA synthetase (i) is capable of acylating the first tRNA (iii) with the first unnatural amino acid or the analogue thereof (ii) comprising a trans-cyclooctenyl group of the formula:

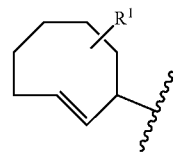

wherein
R¹ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^a$, $R^b$ independently are hydrogen or $C_2$-$C_5$-alkanoyloxymethyl, and said second aminoacyl tRNA synthetase (i) is capable of acylating the second tRNA (iii) with the second unnatural amino acid or the analogue thereof (ii) comprising a trans-cyclooctenyl group of the formula:

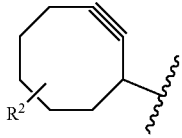

wherein $R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^c$, $R^d$ independently are hydrogen or $C_2$-$C_5$-alkanoyloxymethyl;

b) allowing translation of the polynucleotide (iv) thereby incorporating the first and the second unnatural amino acids or the analogues thereof into the polypeptide at the position(s) encoded by the selector codon(s).

The polypetides of the invention can be reacted with a first tetrazine followed by a second tetrazine in accordance with the methods disclosed herein, for instance in order to introduce two different labels at the sites corresponding to the unnatural amino acids comprising the trans-cyclooctenyl and cyclooctynyl groups, respectively.

Still further, the present invention relates to unnatural amino acids comprising a trans-cyclooctenyl group of the formula:

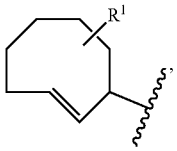

wherein $R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^a$, $R^b$ independently are hydrogen or $C_2$-$C_5$-alkanoyloxymethyl, or an analogue of said unnatural amino acid.

According to one aspect of the invention, said unnatural amino acids have the formula:

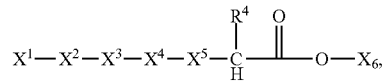

wherein $X^1$ is a trans-cyclooctenyl group of the formula:

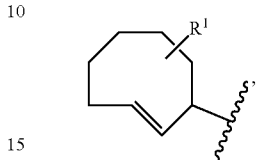

$R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^a$, $R^b$ independently are hydrogen or $C_2$-$C_5$-alkanoyloxymethyl.

$X^2$ is —$CH_2$—, —O—, —S—, —NH—, —C(O)—, —OC(O)—, —C(O)O—, —NH—C(O)— or —C(O)—NH—;

$X^3$ is $C_1$-$C_6$-alkylene, —($CH_2$—$CH_2$—O)$_m$—, —($CH_2$—O)$_p$—, or a single bond;

$X^4$ is —NH—, —C(O)—NH—, —NH—C(O)—, —NH—CH(NH$_2$)—, —CH(NH$_2$)—NH—, —NH—C(NH)—NH—, —C(O)—NH—CH(NH$_2$)—, —C(O)—NH—C(NH)—NH—, NH—CH(NH$_2$)—C(O)— or —NH—C(NH)—NH—C(O)—;

$X^5$ is —($CH_2$)$_n$— or phenylene-$CH_2$—;

$X^6$ is hydrogen, $C_1$-$C_6$-alkyl, $C_1$-$C_6$-alkoxy-$C_1$-$C_2$-alkyl, $C_2$-$C_7$-alkanoyloxy-$C_1$-$C_2$-alkyl or $C_2$-$C_7$-alkanoylsulfanyl-$C_1$-$C_2$-alkyl;

$R^4$ is —OH or —NH$_2$;

n is an integer from 0 to 4;

m is an integer from 1 to 6; and p is an integer from 1 to 6, or an acid or base addition salt thereof.

With respect to the unnatural amino acids' capability of of being translationally incorporated in a polypeptide chain, the variables $X^2$, $X^3$, $X^4$, $X^5$, $X^6$, n, m, p, and $R^4$ have in particular the following meanings which, when taken alone or in combination, represent particular embodiments of the unnatural amino acids disclosed herein or any other formula wherein these variables occur.

$X^2$ is —$CH_2$—, —O—, —S—, —NH—, —C(O)—, —OC(O)—, —C(O)O—, —NHC(O)— or —C(O)NH—.

Preferably, $X^2$ is —O—.

$X^3$ is $C_1$-$C_6$-alkylene, —($CH_2$-$CH_2$—O)$_m$— or a single bond; and m is 1, 2, 3, 4, 5 or 6.

In connection with $X^3$, $C_1$-$C_6$-alkylene preferably refers to straight-chain alkylene.

Preferably, $X^3$ is —$CH_2$-$CH_2$—O— or a single bond.

Alternatively, $X^3$ is —($CH_2$—O)$_p$—; and p is 1, 2, 3, 4, 5 or 6. According to a particular embodiment, $X^3$ is —$CH_2$—O— (i.e., p is 1).

According to one aspect of the invention, the structural element —$X^2$-$X^3$— comprises from 1 to 6 atoms in the main chain, such as 1, 2, 3 or 4 atoms in the main chain.

According to a particular embodiment, —$X^2$-$X^3$— is —O— or —O—($CH_2$)$_2$—O—.

$X^4$ is —NH—, —C(O)—NH—, —NH—C(O)—, —NH—CH(NH$_2$)—, —CH(NH$_2$)—NH—, —NH—C(NH)—NH—, —C(O)—NH—CH(NH$_2$)—, —C(O)—NH—C(NH)—NH—, —NH—CH(NH$_2$)—C(O)— or —NH—C(NH)—NH—C(O)—.

Preferably, $X^4$ is —NH—, —C(O)—NH—, —NH—CH(NH$_2$)—, —NH—C(NH)—NH—, —C(O)—NH—CH(NH$_2$)— or —C(O)—NH—C(NH)—NH—.

According to a preferred embodiment, $X^4$ is —C(O)—NH—.

$X^5$ is —(CH$_2$)$_n$— wherein n is as defined herein, or phenylene-CH$_2$—.

According to one embodiment, $X^5$ is —(CH$_2$)$_n$—.

n is an integer from 1 to 4.

According to one aspect of the invention, n is 3 or 4.

According to a preferred embodiment, n is 4.

According to a further aspect of the invention, n is 1.

According to a further aspect of the invention, $X^5$ is phenylene-CH$_2$—, wherein phenylene is in particular 1,3-phenylene or 1,4-phenylene. 1,4-Phenylene is preferred. The phenylene moiety is attached to $X^4$ and the methylene to the carbon atom carrying $R^4$ (or $Z^1$).

According to a particular embodiment, —$X^4$—(CH$_2$)$_n$— is —NH—(CH$_2$)$_n$—, —NH—C(O)—(CH$_2$)$_n$—, —NH—CH(NH$_2$)—(CH$_2$)$_n$—, —NH—C(NH)—NH—(CH$_2$)$_n$—, —C(O)—NH—CH(NH$_2$)—(CH$_2$)$_n$— or —C(O)—NH—C(NH)—NH—(CH$_2$)$_n$—, wherein n is preferably 3 or 4, or n is 1.

According to a preferred embodiment, —$X^4$—(CH$_2$)$_n$— is —C(O)—NH—(CH$_2$)$_n$—, wherein n is preferably 3 or 4, or n is 1.

According to a further particular embodiment, —$X^4$—(CH$_2$)$_n$— is —NH—(CH$_2$)$_4$—, —NH—C(O)—CH$_2$—, —NH—C(O)—(CH$_2$)$_2$—, —NH—CH(NH$_2$)—(CH$_2$)$_3$—, —NH—CH(NH$_2$)—(CH$_2$)$_4$—, —NH—C(NH)—NH—(CH$_2$)$_3$—, —C(O)—NH—CH(NH$_2$)—(CH$_2$)$_3$—, —C(O)—NH—CH(NH$_2$)—(CH$_2$)$_4$— or —C(O)—NH—C(NH)—NH—(CH$_2$)$_3$—.

According to a preferred embodiment, —$X^4$—(CH$_2$)$_n$— is —C(O)—NH—(CH$_2$)$_4$—.

According to a further embodiment, —$X^4$—(CH$_2$)$_n$— is —C(O)—NH—CH$_2$—.

According to a further particular embodiment, —$X^4$-phenylene-CH$_2$— is —NH-phenylene-CH$_2$—, —NH-phenylene-CH$_2$—, —NH—CH(NH$_2$)-phenylene-CH$_2$—, —NH—C(NH)—NH-phenylene-CH$_2$—, —C(O)—NH—CH(NH$_2$)-phenylene-CH$_2$— or —C(O)—NH—C(NH)—NH-phenylene-CH$_2$—, wherein phenylene is preferably 1,4-phenylene.

According to a particular aspect of the invention, —$X^2$-$X^3$-$X^4$— comprises a carbamate functionality —O—C(O)—NH— (e.g. $X^2$ is —O—, $X^3$ is a bond and $X^4$ is —C(O)—NH—, or $X^3$ is —(CH$_2$—CH$_2$—O)$_m$— or —(CH$_2$—O)$_p$— and $X^4$ is —C(O)—NH—).

According to a particular embodiment, the structural element —$X^2$-$X^3$-$X^4$—(CH$_2$)$_n$— comprises from 5 to 12 atoms in the main chain, such as 6, 7, 8, 9, 10 or 11 atoms in the main chain.

According to a particular embodiment, —$X^2$-$X^3$-$X^4$— is —O—C(O)—NH—, —O—CH$_2$—O—C(O)—NH— or —O—(CH$_2$)$_2$—O—C(O)—NH—.

According to a preferred embodiment, $X^1$-$X^2$-$X^3$-$X^4$—(CH$_2$)$_n$— is $X^1$—O—C(O)—NH—(CH$_2$)$_4$—, $X^1$—O—CH$_2$—O—C(O)—NH—(CH$_2$)$_4$— or $X^1$—O—(CH$_2$)$_2$—O—C(O)—NH—(CH$_2$)$_4$—.

According to a further preferred embodiment, $X^1$-$X^2$-$X^3$-$X^4$—(CH$_2$)$_n$— is $X^1$—O—C(O)—NH—CH$_2$—, $X^1$—O—CH$_2$—O—C(O)—NH—CH$_2$— or $X^1$—O—(CH$_2$)$_2$—O—C(O)—NH—CH$_2$—.

According to a further preferred embodiment, $X^1$-$X^2$-$X^3$-$X^4$-phenylene-CH$_2$— is $X^1$—O—C(O)—NH-phenylene-CH$_2$—, $X^1$—O—CH$_2$—O—C(O)—NH-phenylene-CH$_2$— or $X^1$—O—(CH$_2$)$_2$—O—C(O)—NH-phenylene-CH$_2$—, wherein phenylene is preferably 1,4-phenylene.

$X^6$ is hydrogen, $C_1$-$C_6$-alkyl, $C_1$-$C_6$-alkoxy-$C_1$-$C_2$-alkyl, $C_2$-$C_7$-alkanoyloxy-$C_1$-$C_2$-alkyl or $C_2$-$C_7$-alkanoylsulfanyl-$C_1$-$C_2$-alkyl.

According to a particular embodiment, $X^6$ is hydrogen, $C_1$-$C_6$-alkoxymethyl, $C_1$-$C_6$-alkoxyeth-1-yl (especially 1-($C_1$-$C_6$-alkoxy)eth-1-yl), $C_2$-$C_7$-alkanoyloxymethyl or $C_2$-$C_7$-alkanoylsulfanylethyl.

According to a preferred embodiment, $X^6$ is hydrogen.

$R^4$ is —OH or —NH$_2$. Preferably, $R^4$ is —NH$_2$.

With regard to the asymmetric carbon atom carrying $R^4$ (and $Z^1$) the unnatural amino acid or its analogue of the invention may have S— or R-configuration (according to Cahn-Ingold-Prelog priority rules), with S-configuration being preferred.

According to a preferred embodiment, —$X^5$—CHR$^4$—C(O)O—$X^6$ has formula

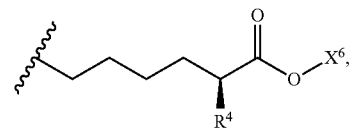

wherein $R^4$ and $X^6$ are as defined herein and $X^6$ is in particular hydrogen.

According to a further preferred embodiment, —$X^5$—CHR$^4$—C(O)O—$X^6$ has formula

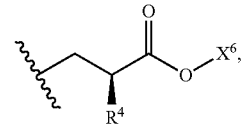

wherein $R^4$ and $X^6$ are as defined herein and $X^6$ is in particular hydrogen.

According to a further preferred embodiment, —$X^5$—CHR$^4$—C(O)O—$X^6$ has formula

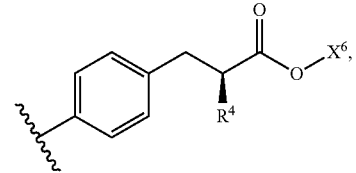

wherein $R^4$ and $X^6$ are as defined herein and $X^6$ is in particular hydrogen.

According to a further particular embodiment, the first unnatural amino acid is a compound of the formula:

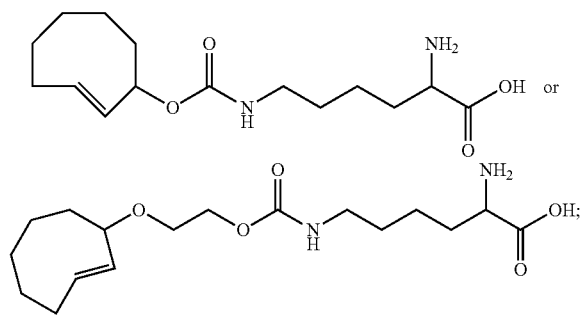

or an acid or base addition salt thereof.

According to a further particular embodiment, the second unnatural amino acid is a compound of the formula:

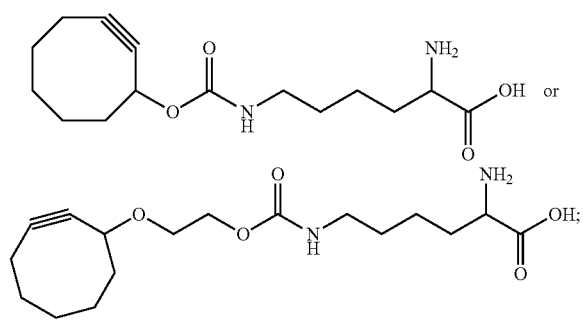

or an acid or base addition salt thereof.

$^1$H-NMR spectra of UAAs 2 (TCO), 3 (TCO*), and 4 (TCO$^\#$) with two equivalents of cysteamine recorded in dPBS/dioxane-d8 (v/v 1:1) after incubation at either room temperature (rt; green lines), 37° C. (red lines), or 60° C. (blue lines) for 24 h. Compounds 2 (TCO) and 4 (TCO$^\#$) were converted to more than 95% into their cis-form after 24 h at 60° C. compared to the $^1$H-NMR spectra recorded directly after mixing the UAAs with cysteamine (upper lines). In contrast, 3 (TCO*) remained to more than 80% in its trans-form. Black dots indicate the signals of the double bond and the —CHO— protons of the trans-form. Black arrows indicate the signals belonging to the corresponding cis-isomers that form upon thiol and heat treatment; c) $^1$H-NMR spectra of UAA 3 (TCO*) with two equivalents of cysteamine recorded in dPBS/dioxane-d8 (v/v 1:1) after incubation at 60° C. after mixing (day 0; upper line, left panel), one day (middle line, left panel), two days (lower line, left panel), three days (upper line, right panel), seven days (middle line, right panel), or ten days (lower line, right panel). Black dots indicate the signals of the double bond and the —CHO— protons of the trans-form. Black arrows indicate the signals belonging to the corresponding cis-isomers that form upon thiol and heat treatment.

Figure 9:
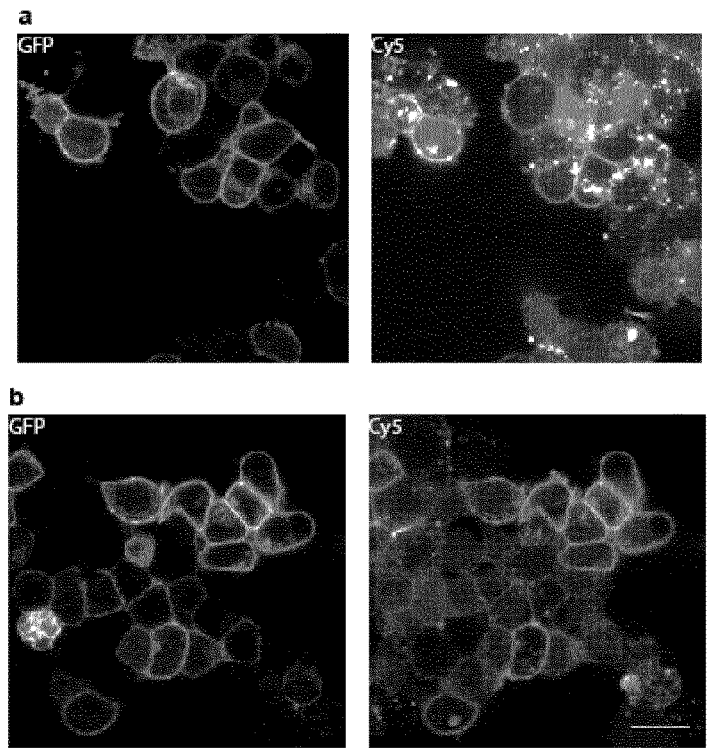

FIG. 9 shows SPAAC labeling of BCN. GFP channel (left) and Cy5 channel (right). a) labeling without endocytosis blocker; b) labeling with endocytosis blocker. Scale bar 20 μm.

Figure 10:
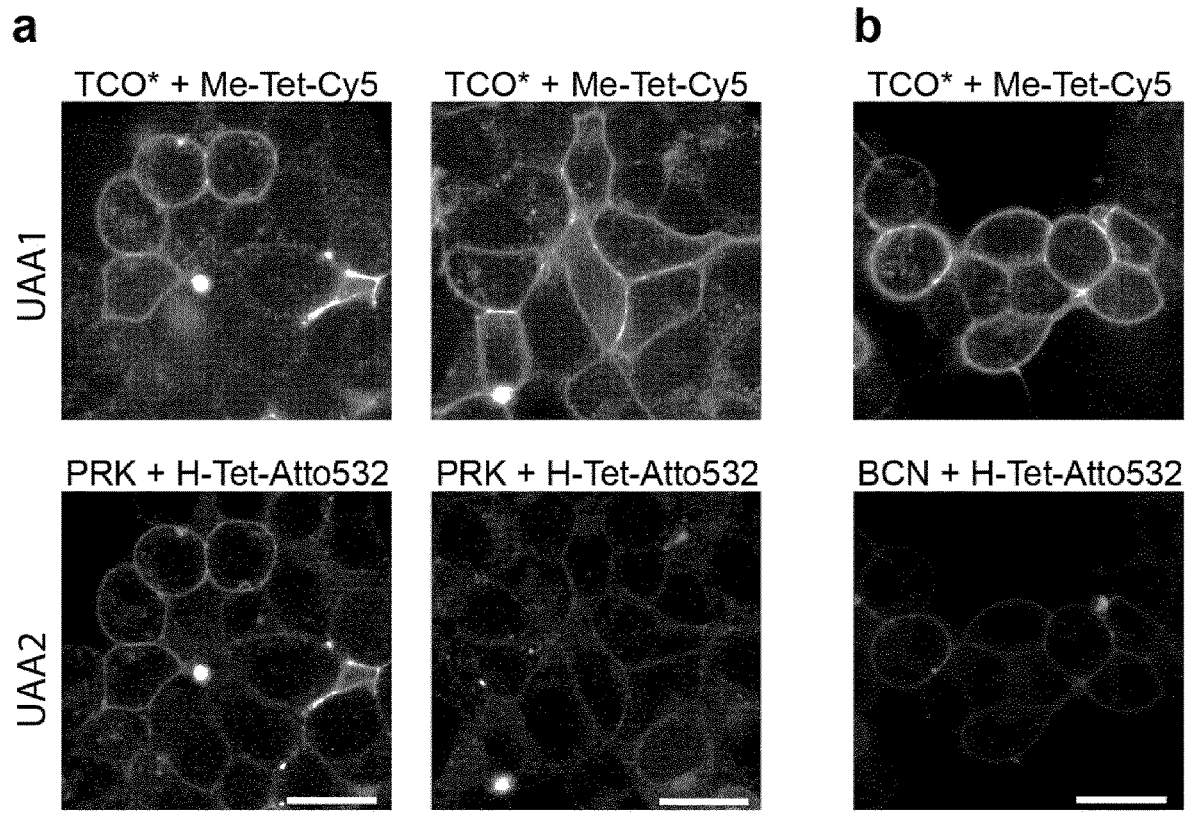
Figure 10:
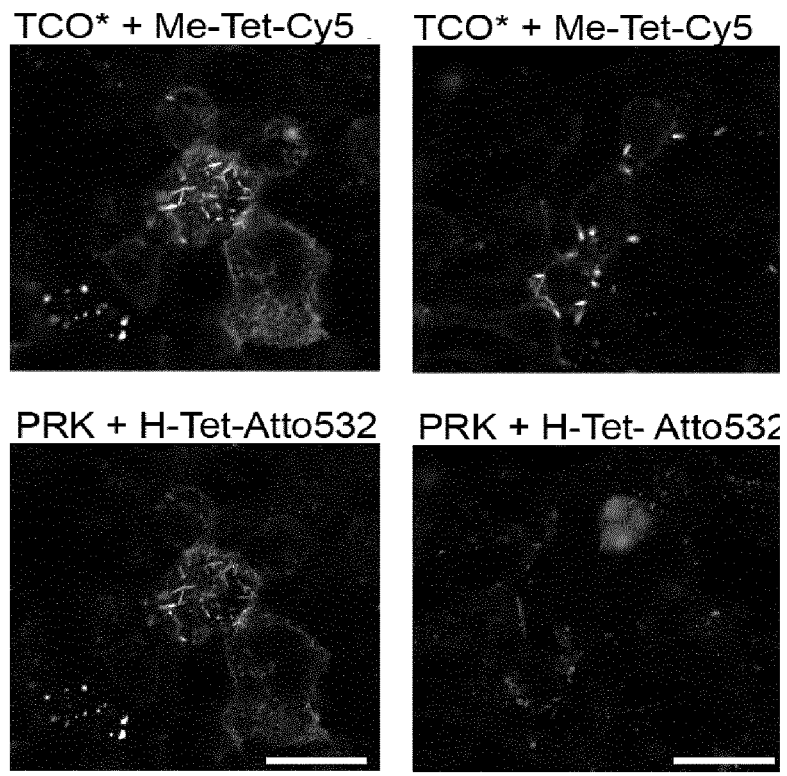
Figure 10:
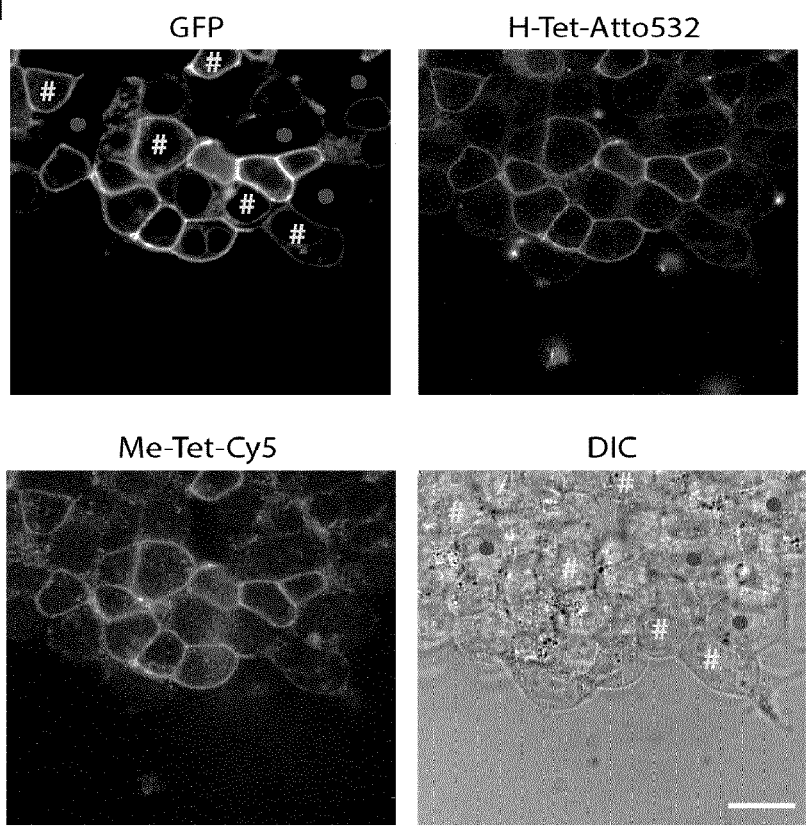

FIG. 10 shows a) TCO* dual-color labeling control of IR without (left) and with quencher (right); b) TCO* and BCN dual-color labeling with the quencher; c) TCO* dual-color labeling control for VLPs; d) Me-Tet-Cy3/H-Tet-Atto532 labeling of pEGFPN1_IR$^{K676TAG}$. Transfected cells are highlighted by the yellow dashes and non-transfected cells (which do not reveal any unspecific sticking or labeling) with red circles. Scale bar 20 μm.

Figure 11:
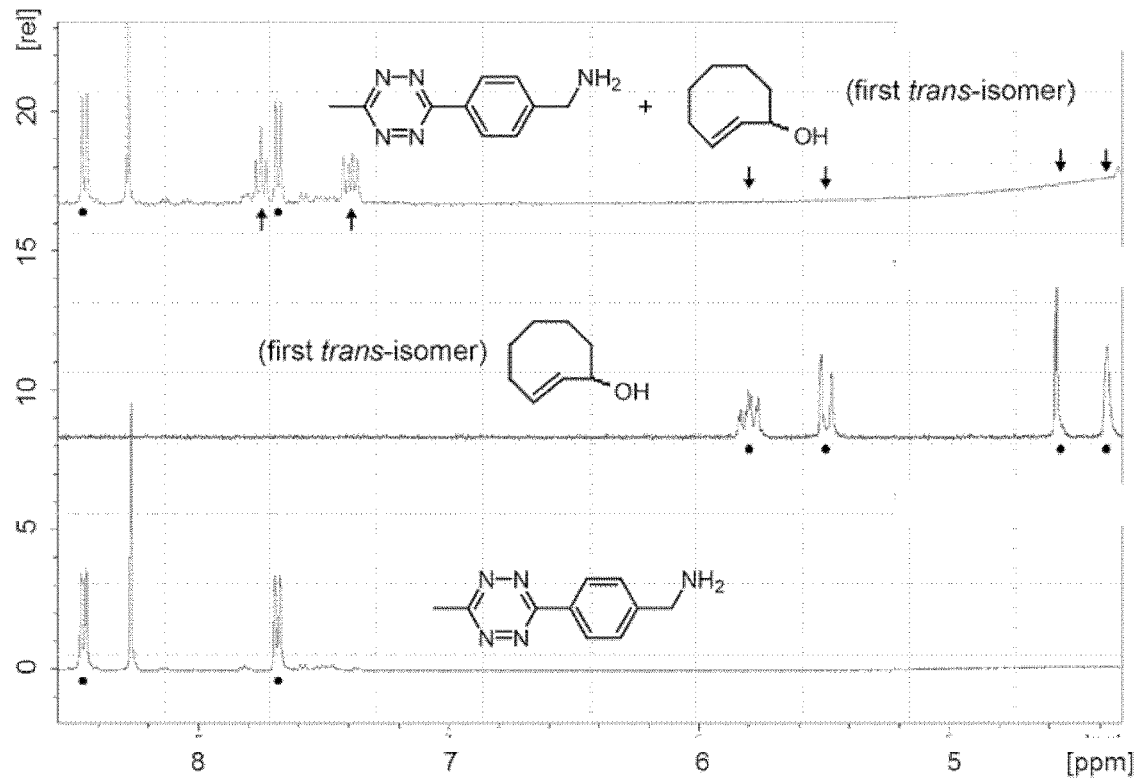
Figure 11:
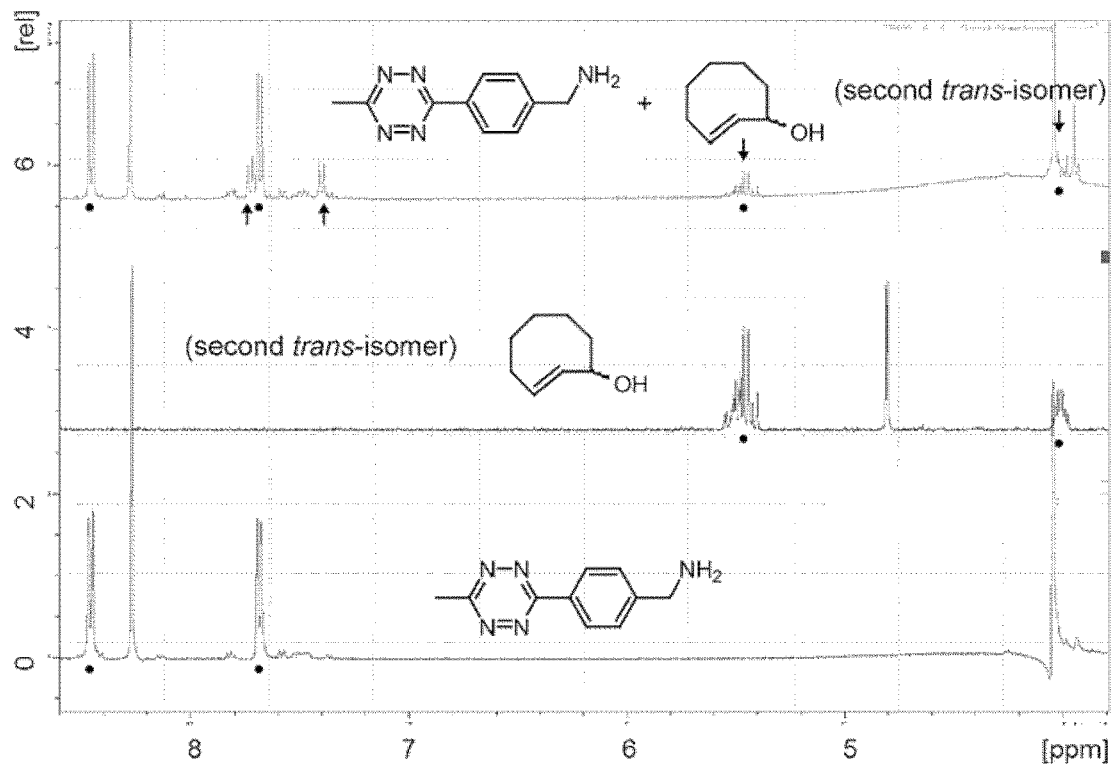
Figure 11:
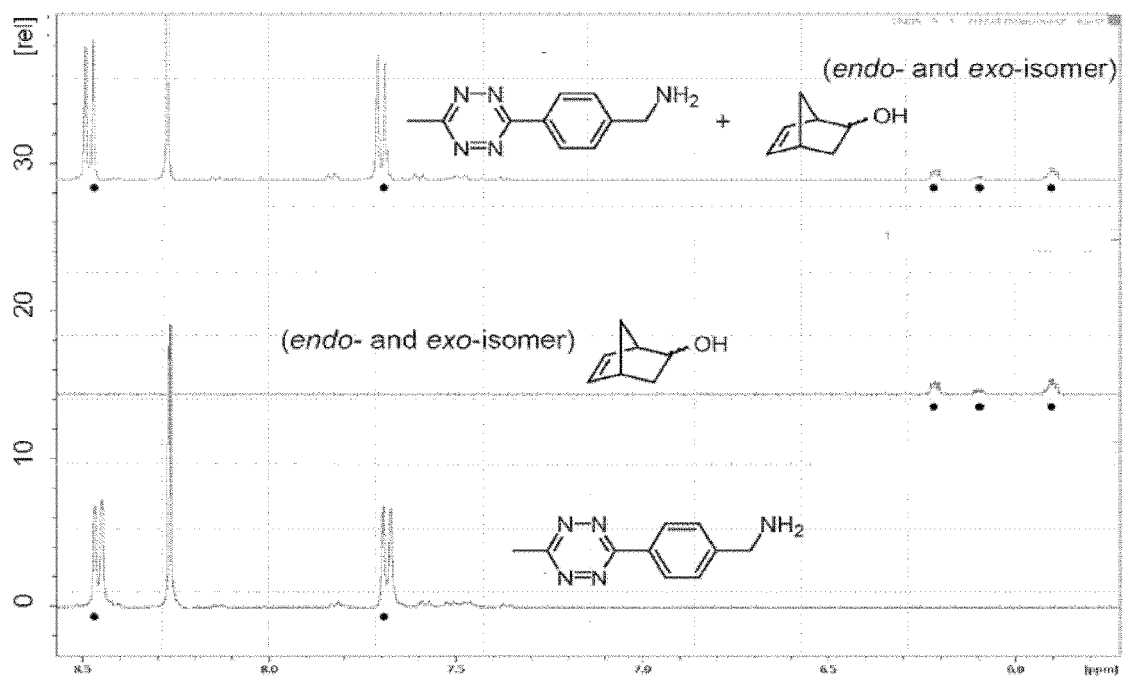
Figure 11:
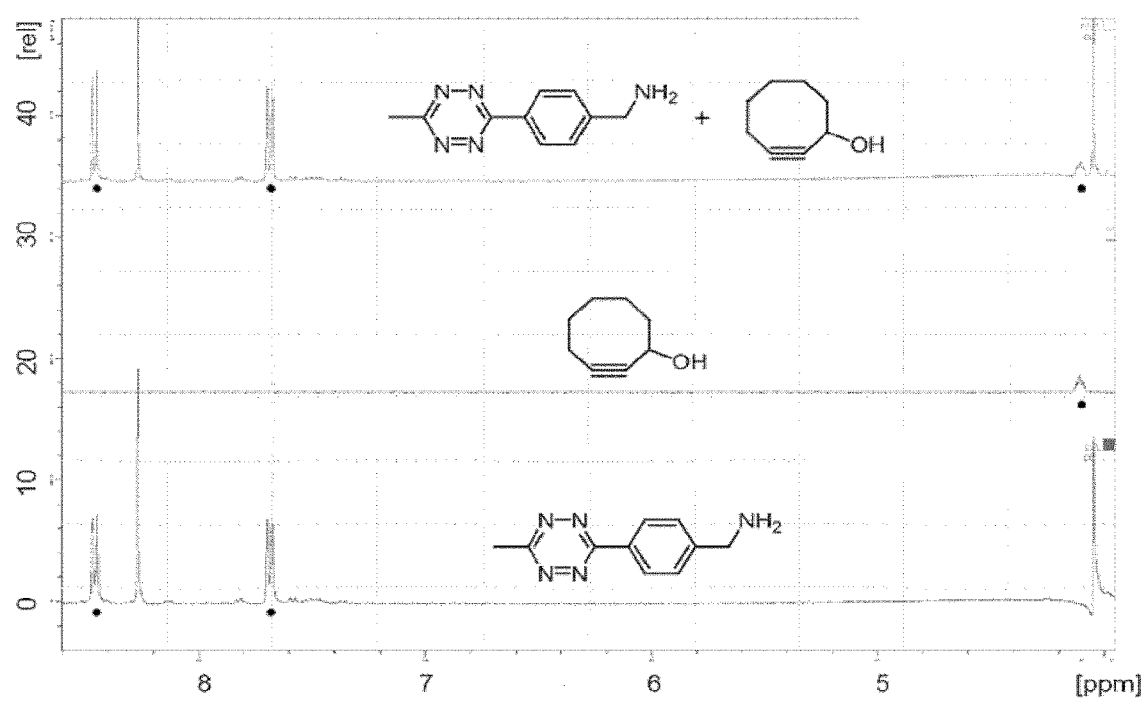
Figure 11:
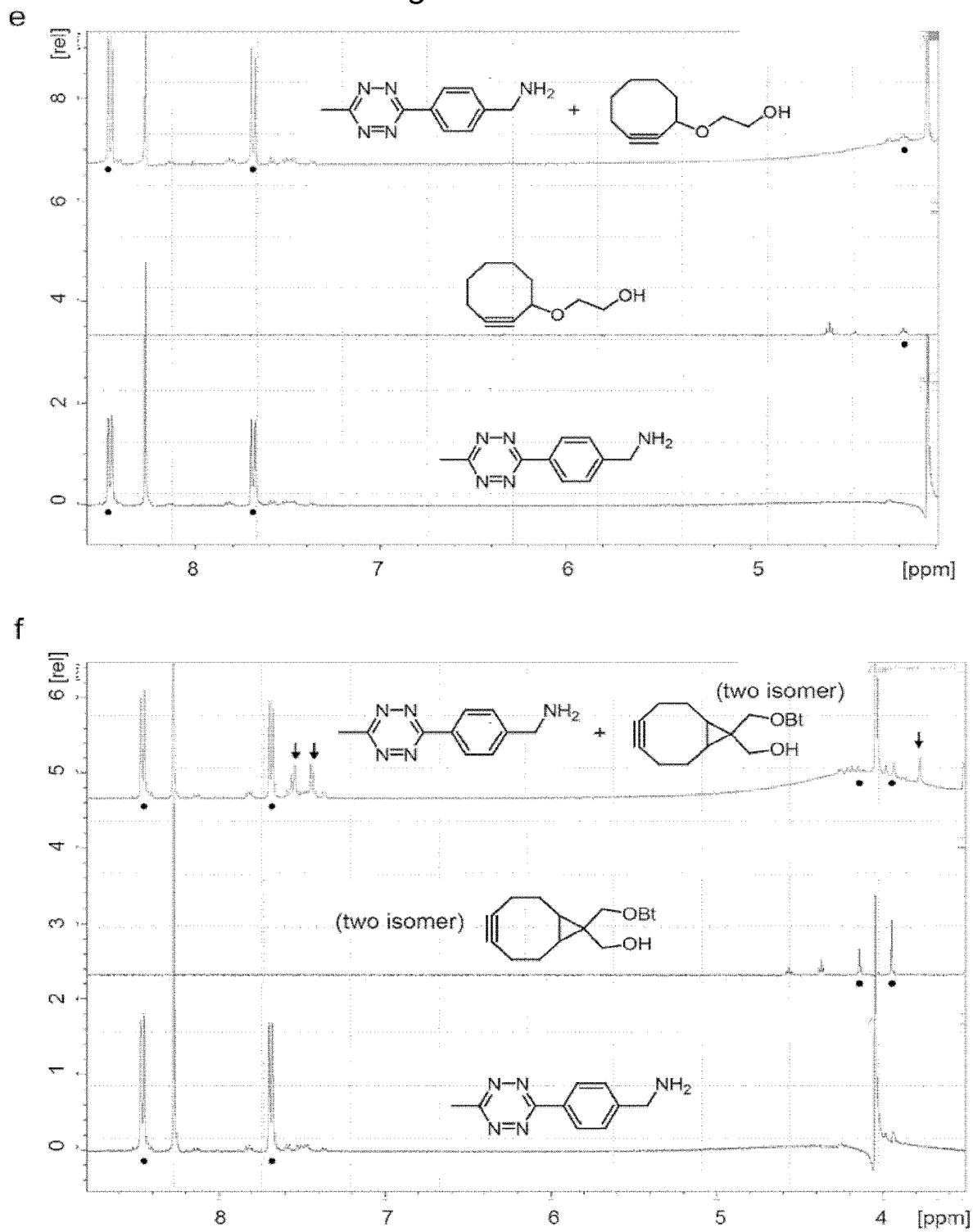

FIG. 11 compares the $^1$H-NMR spectrum of 4-(6-methyl-1,2,4,5-tetrazine-3-yl)phenyl)methanamine (lower line), the indicated dienophile (middle line) and the reaction product recorded 10 min after mixing 4-(6-methyl-1,2,4,5-tetrazine-3-yl)phenyl)methanamine with the indicated dienophile (upper line).

Figure 12:
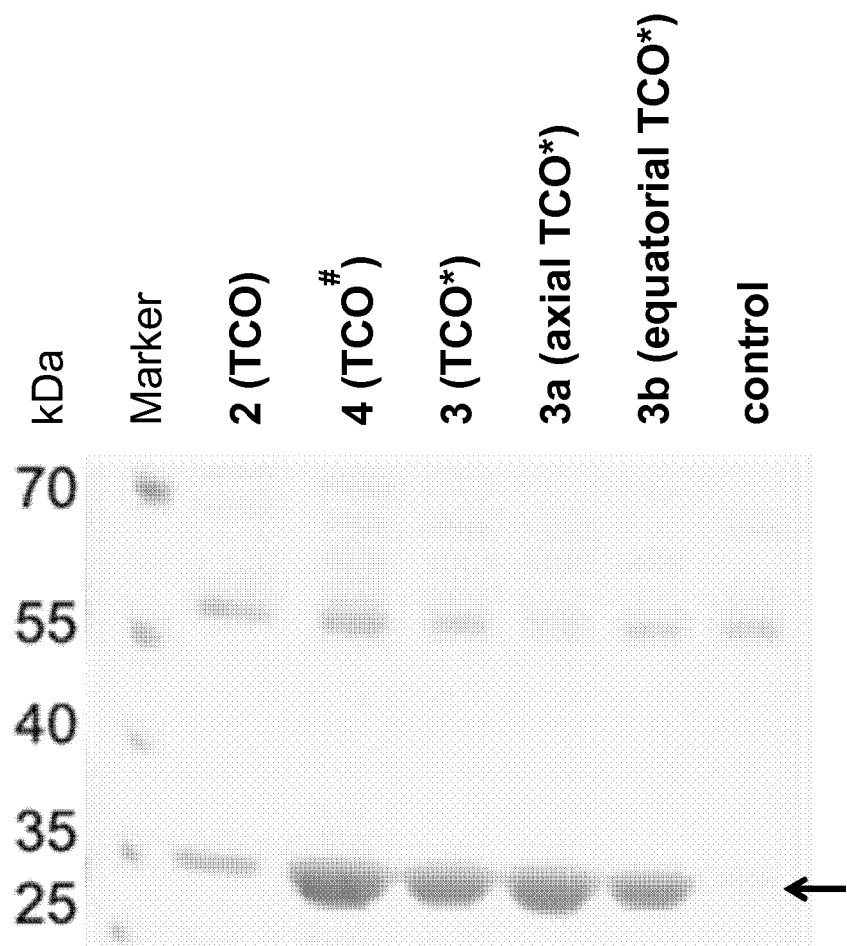

FIG. 12 shows a Coomassie-stained SDS-PAGE gel of purified GFP$^{TAG \to UAA}$ expressed in the absence (control) or presence of an UAA (2, 3, 3a, 3b or 4). Synthetase bands are slightly above the 55 kDa molecular weight marker and GFP bands are at about the height of the 35 kDa molecular weight marker (arrow). GPF bands are only present when the Y39TAG mutation is successfully suppressed. Compound 3 (TCO*), 3a (axial isomer of TCO*), 3b (equatorial isomer of TCO*) and 4 (TCO$^\#$) show higher expression yields than the TCO (4).

Figure 13:
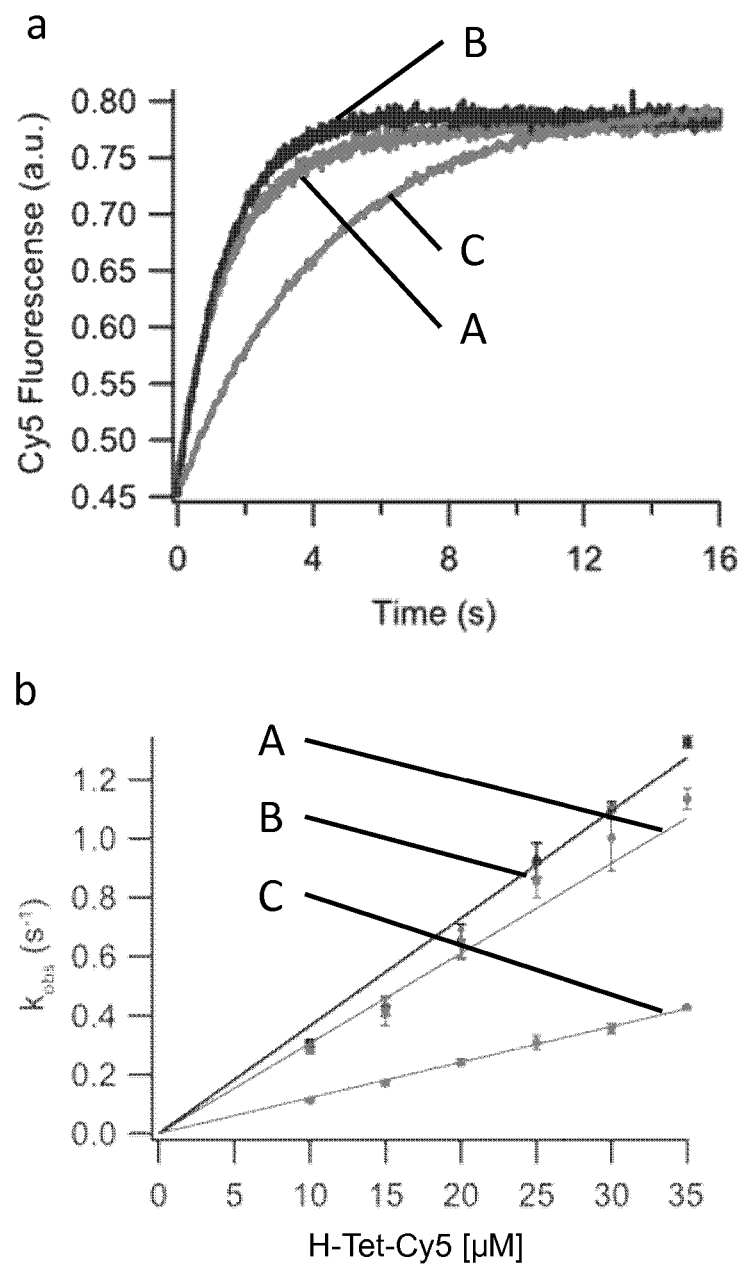

FIG. 13 shows: a) the increase of Cy5 (acceptor) fluorescence during the in vitro labeling reaction of GFP$^{TAG \to 3}$ (A), GFP$^{TAG \to 3a}$ (B) or GFP$^{TAG \to 3b}$ (C) with H-Tet-Cy5; and b) linear fits of the observed reaction rate constants $k_{obs}$ vs. concentration of H-Tet-Cy5.

Figure 14:
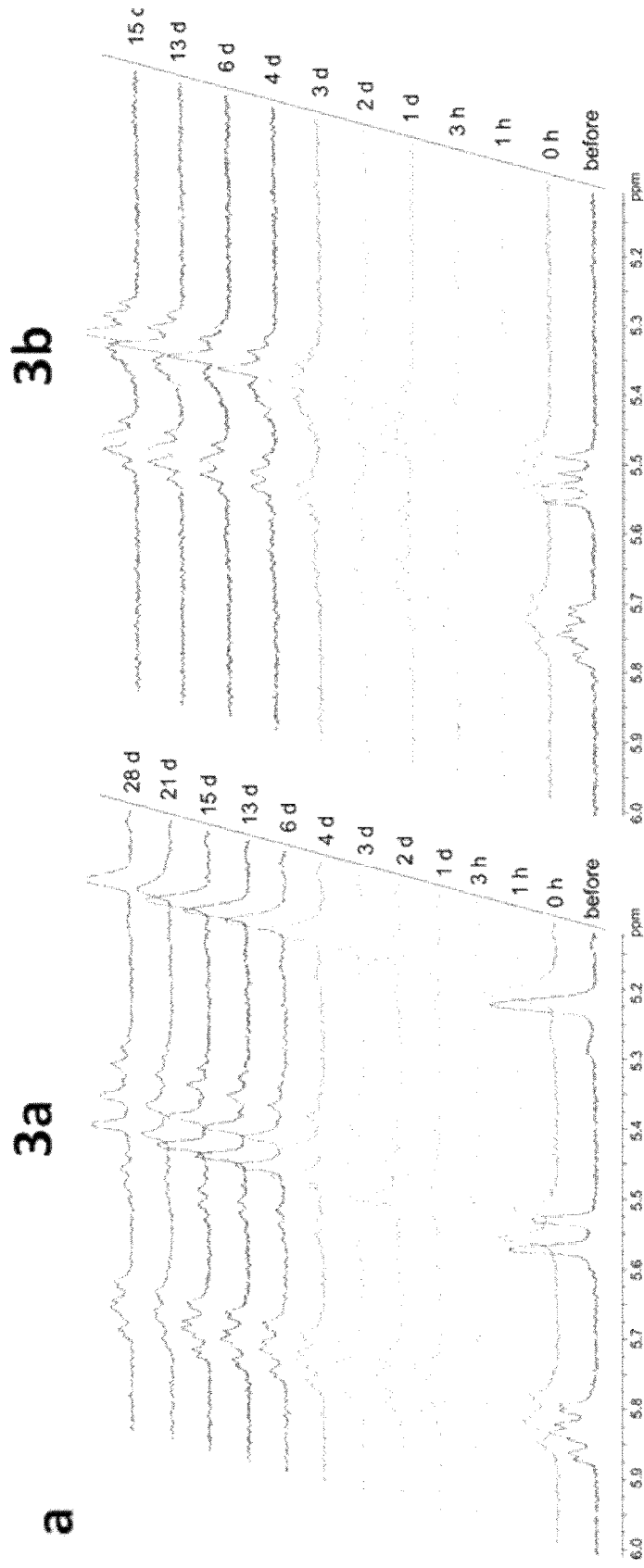
Figure 14:
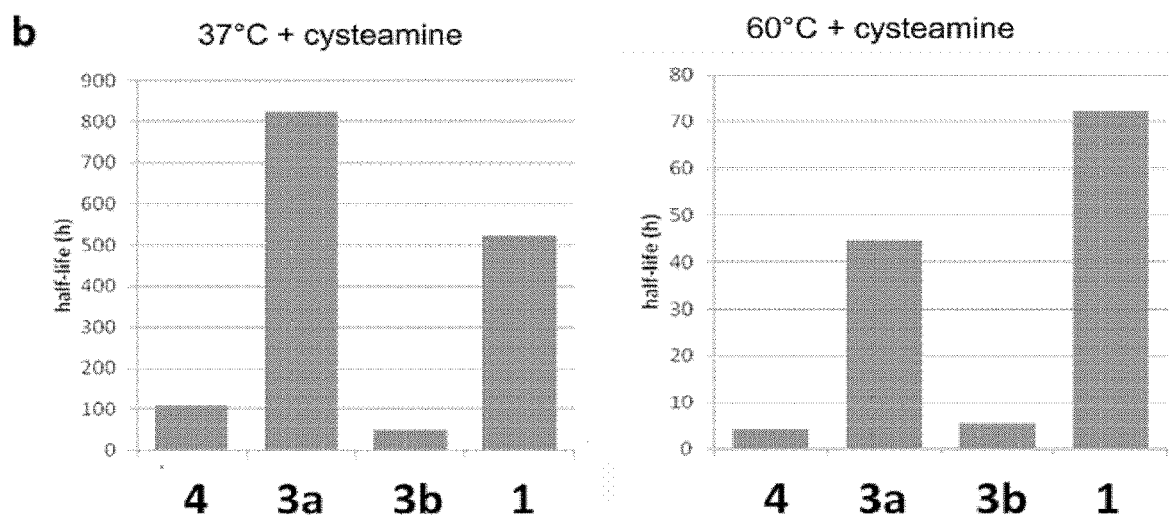

FIG. 14 shows: a) the changes of the $^1$H-NMR profiles of the axial isomer 3a and the equatorial isomer 3b when treated with cysteamine hydrochloride at 37° C. for 0 h, 1 h, 3 h, 1 d, 2d, 3d, 4d, 6d, 13d, 15d, 21d or 28d; and b) the half-life of compounds 4 (TCO), 3a (axial isomer of TCO*), 3b (equatorial isomer of TCO*) and 1 (BCN).

Figure 15:
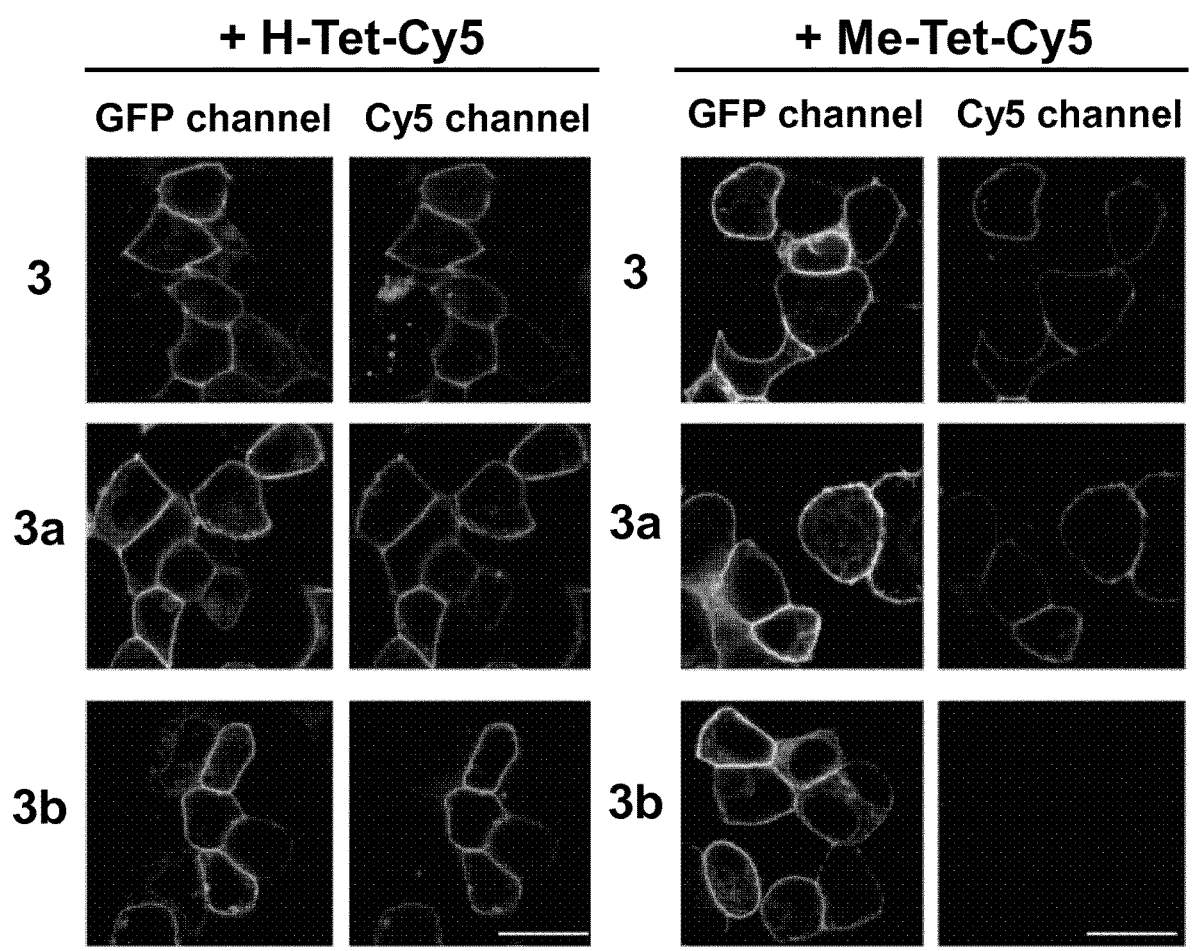

FIG. 15 shows confocal images of HEK293T cells expressing a recombinant fusion of insulin receptor (IR) and (C-terminal) GFP, wherein compound 3, 3a or 3b has been incorporated at the amber-encoded site (i.e. expressing GFP-IR$^{TAG \to 3}$, GFP-IR$^{TAG \to 3a}$ or GFP-IR$^{TAG \to 3b}$) which were labeled with H-Tet-Cy5 or Me-Tet-Cy5, respectively. GFP fluorescence (GFP channel) indicates successful expression of the recombinant GFP-IR$^{TAG \to UAA}$ protein. Cy5 fluorescence (Cy5 channel) indicates successful labeling of the recombinant GFP-IR$^{TAG \to UAA}$ protein. Scale bar is 20 μm.

DETAILED DESCRIPTION OF THE INVENTION

The invention is based inter alia on the finding that alkyl-substituted tetrazines preferentially react with strained dienophiles comprising a trans-cyclooctenyl group as compared to strained dienophiles comprising a cyclooctynyl group. Thus, in a competitive situation where trans-cyclooctenyl and cyclooctynyl groups are present, the alkyl-substituted tetrazines will preferentially react with the trans-cyclooctenyl groups. In this context, the term "preferentially reacts" refers to a ratio of rate constants k, which ratio is 100 or higher, 200 or higher, 500 or higher, or 1000 or higher, if the rate constant $k_1$ for the reaction of the alkyl-substituted tetrazines with the strained dienophiles comprising a trans-cyclooctenyl group is compared to the rate constant $k_2$ for the reaction of the alkyl-substituted tetrazines with the strained dienophiles comprising a cyclooctynyl group (i.e., the ratio is $k_1/k_2$). Accordingly, the reaction of the alkyl-substituted tetrazine with the strained dienophile comprising a trans-cyclooctenyl group can proceed to a point where substantially all trans-cyclooctenyl groups have reacted with the alkyl-substituted tetrazine while substantially no cyclooctynyl group has yet reacted with the alkyl-substituted tetrazine.

According to certain embodiments of the invention, alkyl-substituted tetrazines specifically react with the strained dienophiles comprising a trans-cyclooctenyl group. Thus, in a competitive situation where trans-cyclooctenyl and cyclooctynyl groups are present, the alkyl-substituted tetrazines will preferentially react with the trans-cyclooctenyl groups. In this context, the term "specifically reacts" refers to a ratio of rate constants k, which ratio is 2000 or higher, 5000 or higher, or 10000 or higher, if the rate constant $k_1$ for the reaction of the alkyl-substituted tetrazines with the strained dienophiles comprising a trans-cyclooctenyl group is compared to the rate constant $k_2$ for the reaction of the alkyl-substituted tetrazines with the strained dienophiles comprising a cyclooctynyl group (i.e., the ratio is $k_1/k_2$). Accordingly, the reaction of the alkyl-substituted tetrazines with the strained dienophile comprising a trans-cyclooctenyl group can proceed to a point where all trans-cyclooctenyl groups have reacted with the alkyl-substituted tetrazine while substantially no cyclooctynyl group has yet reacted with the alkyl-substituted tetrazine.

The reactions of the invention can be performed in vitro or in vivo, depending on the appropriate reaction conditions. Because only the first and second dienophile groups (e.g. the unnatural amino acids comprising said groups present on the target polypeptides) participate in the ligation reaction, the methods of the invention can be reliably used to produce homogenous populations of well-defined conjugates (e.g., target polypeptide-label conjugates comprising defined stoichiometries and defined ligation sites) with high efficiency and specificity. Because any of a variety of reactive first and second modifying agents (e.g. unnatural amino acids) comprising the first and second dienophile groups can be incorporated into a variety of molecules (e.g. target polypeptides), the production of conjugates (e.g. target polypeptide conjugates) is not limited to specific molecules (e.g. polypeptides). Furthermore, existing technologies beneficially permit the incorporation of unnatural amino acids into any amino acid position in a polypeptide. Thus, placement of the first and second chemically reactive unnatural amino acids in the target polypeptides, can optionally be chosen based on, e.g., whether placement in that location would change, e.g., the conformations, biological activities, pharmacological activities, stabilities, bioavailabilities, or other properties, of the target polypeptide, or of the resulting target polypeptide-label conjugates.

The term "unnatural amino acid" refers to an amino acid that is not one of the 20 canonical amino acids or selenocysteine or pyrrolysine. The term also refers to amino acid analogues, e.g. wherein the α-amino group is replaced by a hydroxyl group; or wherein the carboxylic acid function forms an ester. Actually, when unnatural amino acids of the invention or salts thereof, wherein $X^6$ is other than hydrogen, are used for preparation of polypeptides in a translation system, it is believed that $X^6$ is removed in situ, for example enzymatically within the chosen translation system, prior of being incorporated in the polypeptide. Accordingly, $X^6$ is expediently chosen so as to be compatible with a translation system's ability to convert unnatural amino acids of the invention or salts thereof into a form that is recognized and processed by the aminoacyl tRNA synthetase.

The compounds or salts of the invention possess centers of asymmetry and may exist in different spatial arrangements or as different tautomers. For preparation of polypeptides with trans-cyclooctenyl or cyclooctynyl groups, enantiomeric mixtures, in particular racemates, diastereomeric mixtures and tautomeric mixtures may be used. Alternatively, the respective essentially pure enantiomers, diastereomers and tautomers of the compounds or salts of the invention may be used for such purpose.

More specifically, the trans-cyclooctenyl group of the formula:

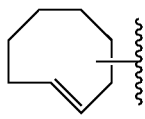

is meant to encompass two isomeric forms which differ from one another by the absolute configuration at the carbon atom where the trans-cyclooctene ring is attached to the remainder of the molecule. Accordingly, one can distinguish the two enantiomers having an S or R configuration, e.g. the enantiomers of the formulae

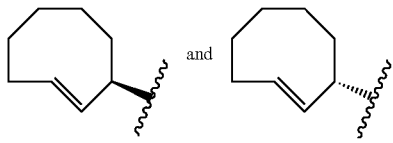

Due to atropisomerism, trans-cylooctenyl groups exist in four different stereoisomeric forms. With regard to the carbon atom where the trans-cylooctene ring is attached, one differentiates axial isomers and equatorial isomers (i.e. the remainder of the molecule is attached in axial or equatorial position relative to the trans-cyclooctene ring). For each of said axial and for each of said equatorial isomeric form there are two enantiomers. Accordingly, the stereoisomers of the trans-cyclooctenyl group can be depicted by the formulae

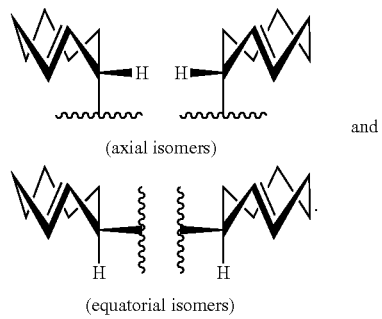

Unless indicated otherwise, the term "axial isomer" refers to a mixture of both enantiomers (in particular a racemate) of the axial isomeric form, and the term "equatorial isomer" refers to a mixture of both enantiomers (in particular a racemate) of the equatorial isomeric form.

The organic moieties mentioned in the above definitions of the variables are—like the term alkyl—collective terms for individual listings of the individual group members. The prefix $C_{n-m}$ indicates in each case the possible number of carbon atoms in the group.

The term halogen denotes in each case a fluorine, bromine, chlorine or iodine radical, in particular a fluorine radical.

Alkyl is a straight-chain or branched alkyl group having from 1 to 6, in particular 1 to 4 or 1 to 3 carbon atoms. Examples include methyl, $C_2$-$C_4$-alkyl such as ethyl, n-propyl, iso-propyl, n-butyl, 2-butyl, iso-butyl or tert-butyl, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Alkenyl is a singly unsaturated hydrocarbon radical having 2, 3, 4, 5 or 6 carbon atoms, e.g. vinyl, allyl (2-propen-1-yl), 1-propen-1-yl, 2-propen-2-yl, methallyl (2-methyl-prop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl, 2-ethylprop-2-en-1-yl, 2-hexen-1-yl and the like.

Alkylene is straight-chain or branched alkylene group having from 1 to 6, in particular 1 to 4 carbon atoms. Examples include methylene, ethylene, 1,2-ethylene, 1,3-propylene, isopropylene, 1-4-butylene, 1-5-pentylene and the like.

Alkoxy is a radical of the formula R—O—, wherein R is a straight-chain or branched alkyl group having from 1 to 6, in particular 1 to 4 or 1 to 3 carbon atoms as defined herein.

Alkenoxy is a radical of the formula R—O—, wherein R is a straight-chain or branched alkenyl group having from 1 to 6, in particular 1 to 4 or 1 to 3 carbon atoms as defined herein.

Alkanoyloxy is a radical of the formula R—(CO)—O—, wherein R is a straight-chain or branched alkyl group having from 1 to 6, in particular 1 to 4 or 1 to 3 carbon atoms as defined herein.

Alkylaminocarbonyloxy is a radical of the formula R—NH—(CO)—O—, wherein R is a straight-chain or branched alkyl group having from 1 to 6, in particular 1 to 4 or 1 to 3 carbon atoms as defined herein.

Alkylthio is a radical of the formula R—S—, wherein R is an alkyl radical having from 1 to 4, preferably from 1 to 3 carbon atoms as defined herein.

Alkanoylsulfanyl is a radical of the formula R—(CO)—S—, wherein R is a straight-chain or branched alkyl group having from 1 to 6, in particular 1 to 4 or 1 to 3 carbon atoms as defined herein.

Alkylamino is a radical of the formula R—NH— wherein R is an alkyl radical having from 1 to 6, in particular from 1 to 4 carbon atoms as defined herein. Examples include methylamino, ethylamino, n-propylamino, iso-propylamino, n-butylamino, 2-butylamino, iso-butylamino, tert-butylamino and the like.

Dialkylamino is a radical of the formula RR'N— wherein R and R' are independently of each other an alkyl radical having from 1 to 6, in particular from 1 to 4 carbon atoms as defined herein. Examples include dimethylamino, diethylamino, N-methyl-N-ethylamino and the like.

Alkenylamino is a radical of the formula R—NH— wherein R is an alkenyl radical having from 2 to 6, in particular from 2 to 4 carbon atoms as defined herein. Examples include vinylamino, allylamino (2-propen-1-yl-amino), 1-propen-1-yl-amino, 2-propen-2-yl-amino, methallylamino (2-methylprop-2-en-1-yl-amino) and the like.

N-Alkyl-N-alkenylamino is a radical of the formula RR'N— wherein R is an alkyl radical having from 1 to 6, in particular from 1 to 4 carbon atoms as defined herein and R' an alkenyl radical having from 2 to 6, in particular from 2 to 4 carbon atoms as defined herein. Examples include N-methyl-N-vinylamino, N-methyl-N-allylamino (N-methyl-N-2-propen-1-yl-amino), N-methyl-N-1-propen-1-yl-amino, N-methyl-N-2-propen-2-yl-amino, N-methyl-N-methallylamino (N-methyl-N-2-methylprop-2-en-1-yl-amino) and the like.

Dialkenylamino is a radical of the formula RR'N— wherein R and R' are independently of each other an alkyl radical having from 2 to 6, in particular from 2 to 4 carbon atoms as defined herein. Examples include divinylamino, diallylamino (di-(2-propen-1-yl)-amino), N-vinyl-N-allylamino and the like.

Unless indicated otherwise, the term "substituted" means that a radical is substituted with 1, 2 or 3, especially 1 or 2, substituent(s) which are in particular selected from the group consisting of halogen, $C_1$-$C_4$-alkyl, CN, $CF_3$, hydroxyl, —O—$CF_3$, $C_1$-$C_4$-alkoxy, $C_2$-$C_4$-alkanoyloxy, $C_1$-$C_4$-alkylaminocarbonyloxy and $C_1$-$C_4$-alkylthio.

The acid or base addition salts of the compounds of the invention are especially addition salts with physiologically tolerated acids or bases. Physiologically tolerated acid addition salts can be formed by treatment of the base form of a compound of the invention with appropriate organic or inorganic acids. Compounds of the invention containing an acidic proton may be converted into their non-toxic metal or amine addition salt forms by treatment with appropriate organic and inorganic bases. The compounds and salts of the invention also comprise the hydrates and solvent addition forms thereof, e.g. hydrates, alcoholates and the like.

Physiologically tolerated acids or bases are in particular those which are tolerated by the system used for the incorporation of the first and second dienophiles (e.g. a biological system such as a translation system used for preparation of polypeptides with trans-cyclooctenyl or cyclooctynyl groups), e.g. which are substantially non-toxic to living cells.

The compounds and salts of the invention (e.g. the dienophiles ad tetrazines of the invention) can be prepared by analogy to methods which are well known in the art. Suitable methods for the preparation of compounds of formula (I) are found in the various publications cited herein, all of which are incorporated herein by reference in their entireties. Some methods are outlined herein.

The compounds and salts of the invention can be used for preparation of polypeptides comprising one or more than one cyclooctynyl or trans-cyclooctenyl analog group. The invention provides processes for preparing such polypeptides, in vivo or in vitro. In particular, the compounds or salts of the invention can be translationally incorporated in a polypeptide that is encoded by a polynucleotide comprising one or more than one selector codon(s). A polypeptide is any oligomer of amino acid residues (natural or unnatural, or a combination thereof), of any length, typically but not exclusively joined by covalent peptide bonds. A polypeptide can be from any source, e.g., a naturally occurring polypeptide, a polypeptide produced by recombinant molecular genetic techniques, a polypeptide from a cell or translation system, or a polypeptide produced by cell-free synthetic means. A polypeptide is characterized by its amino acid sequence, e.g., the primary structure of its component amino acid residues. As used herein, the amino acid sequence of a polypeptide is not limited to full-length sequences, but can be partial or complete sequences. Furthermore, it is not intended that a polypeptide be limited by possessing or not possessing any particular biological activity. As used herein, the term "protein" is synonymous with polypeptide. The term "peptide" refers to a small polypeptide, for example but not limited to, from 2-25 amino acids in length. As used herein, "to incorporate an unnatural amino acid", e.g., into a target polypeptide, refers to the direct addition of an unnatural amino acid to a growing polypeptide chain during primary construction of the target polypeptide, e.g., via translation or chemical synthesis.

First and second unnatural amino acids can be directly incorporated into target polypeptides using any of a number of methods known in the art. While many embodiments utilize orthogonal translation systems as the route of direct incorporation of the unnatural amino acids, other direct incorporation methods (e.g., in vitro translation systems, solid-phase synthesis, etc.) can be used alternatively. It will be appreciated that in typical embodiments herein, an unnatural amino acid is preferably incorporated into target polypeptide, i.e., during construction of the polypeptide, and is not added via post-translational chemical derivatization.

In certain embodiments described herein, the unnatural amino acids can be site-specifically incorporated into a target polypeptide with high efficiency and high fidelity using orthogonal tRNA/aminoacyl-tRNA synthetase pairs. Methylotrophic yeast are attractive candidates for use as recombinant expression systems for heterologous, therapeutically useful proteins. The eukaryotic subcellular organization of methylotrophic yeast enables them to carry out many of the posttranslational folding, processing and modification events required to synthesize biologically active carrier polypeptides and/or target polypeptides derived from mammals. Unlike proteins expressed in *S. cerevisiae,* proteins produced by methylotrophic yeast such as *P. pastoris, P. methanolica, P. angusta* (also known as *Hansenula polymorpha*), *Candida boidinii,* and *Torulopsis* spp., are less likely to contain high-mannose glycan structures that can hamper downstream processing of heterologously expressed glycoproteins. In addition, target polypeptides synthesized in methylotrophic yeast are advantageously free of pyrogenic and antigenic compounds often characteristic of proteins expressed in E. coli. Most significantly, methylotrophic yeast expression systems are particularly useful for large-scale synthesis. For example, orthogonal translation systems in methylotrophic yeast can permit the expression of target polypeptides comprising unnatural amino acids at levels 10- to 100-fold higher than in S. cerevisiae, bacterial, insect, or mammalian systems. In addition, methylotrophic yeast can be easily cultured in a simple, defined salt medium, eliminating the need for the expensive media supplements and equipment that are required for baculovirus expression systems.

The term "translation system" refers to the components necessary to incorporate an amino acid in a growing polypeptide chain (protein). Components of a translation system can include, e.g., ribosomes, tRNAs, synthetases, mRNA and the like.

The translation system may be an in vivo or an in vitro translation system.

An in vitro translation system may be a cell-free translation system. A cell-free translation system is a system for synthesizing a desired protein by obtaining protein factors required for mRNA translation, e.g., in form of a cell extract, followed by reconstituting this reaction in vitro. Such cell-free systems and their use for protein synthesis are known in the art. Examples include extracts of E. coli, wheat germ extract, or rabbit reticulocyte lysate (Spirin and Swartz, Cell-free Protein Synthesis, Wiley VCH Verlag, Weinheim, Germany, 2008).

Preferably, the translation system used in the process of the invention is an in vivo translation system. An in vivo translation system can be a cell, e.g. a prokaryotic or eukaryotic cell. The cell can be a bacterial cell, e.g. E. coli; a fungal cell such as a yeast cell, e.g. S. cerevisiae or a methylotrophic yeast; a plant cell, or an animal cell such as an insect cell or a mammalian cell, e.g. a HEK cell or a HeLa cell. Eukaryotic cells used for polypeptide expression may be single cells or parts of a multicellular organism.

According to a particular embodiment, the translation system is an E. coli cell.

According to a further particular embodiment, the translation system is a mammalian cell, e.g. a HEK or HeLa cell.

A translation system useful for preparation of polypeptides of the invention comprises, in particular, an aminoacyl tRNA synthetase, or a polynucleotide encoding it; a tRNA having an anticodon to a selector codon, or a polynucleotide encoding said tRNA; and a polynucleotide encoding the target polypeptide and comprising one or more than one selector codon(s).

For example, polynucleotides encoding the aminoacyl tRNA synthetase, the tRNA and the polypeptide of the invention may be introduced into a cell by transfection/transformation known in the art.

An aminoacyl tRNA synthetase (RS) is an enzyme capable of acylating a tRNA with an amino acid or amino acid analog. Expediently, the RS used in the methods of the invention is capable of acylating a tRNA with an unnatural amino acid of the invention.

The methods of the invention expediently utilize a tRNA aminoacyl tRNA synthetase (tRNA/RS) pair. Preferably, the tRNA/RS pair used in the processes of the invention is orthogonal to the translation system.

The term "orthogonal" as used herein refers to a molecule (e.g., an orthogonal tRNA (O-tRNA) and/or an orthogonal aminoacyl tRNA synthetase (O—RS)) that is used with reduced efficiency by a translation system of interest (e.g., a cell). Orthogonal refers to the inability or reduced efficiency, e.g., less than 20% efficient, less than 10% efficient, less than 5% efficient, or e.g., less than 1% efficient, of an orthogonal tRNA or an orthogonal aminoacyl tRNA synthetase to function with the endogenous aminoacyl tRNA synthetases or endogenous tRNAs of the translation system of interest.

For example, an orthogonal tRNA in a translation system of interest is acylated by any endogenous aminoacyl tRNA synthetase of a translation system of interest with reduced or even zero efficiency, when compared to acylation of an endogenous tRNA by the endogenous aminoacyl tRNA synthetase. In another example, an orthogonal aminoacyl tRNA synthetase acylates any endogenous tRNA in the translation system of interest with reduced or even zero efficiency, as compared to acylation of the endogenous tRNA by an endogenous aminoacyl tRNA synthetase.

Orthogonal tRNA/RS pairs used in processes of the invention preferably have following properties: the O-tRNA is preferentially acylated with the unnatural amino acid of the invention by the O—RS. In addition, the orthogonal pair functions in the translation system of interest, e.g., the translation system uses the unnatural amino acid acylated O-tRNA to incorporate the unnatural amino acid of the invention in a polypeptide chain. Incorporation occurs in a site specific manner, e.g., the O-tRNA recognizes a selector codon, e.g., an amber stop codon, in the mRNA coding for the polypeptide.

In some aspects, the translation system comprises a second orthogonal pair, e.g., a second O—RS and a second O-tRNA that utilize the second unnatural amino acid, so that the system is now able to incorporate at least two different unnatural amino acids at different selected sites in a polypeptide. In this embodiment, the second O—RS preferentially aminoacylates the second O-tRNA with the second unnatural amino acid that is different from the first unnatural amino acid, and the second O-tRNA recognizes a selector codon that is different from the selector codon recognized by the first O-tRNA. Suitable translation systems comprising two orthogonal tRNA/RS pairs are known in the art. See, for instance, Han Xiao, et al., Angew Chem Int Ed Engl 2013, 52, 14080-14083.

In some embodiments, the translation system comprises a cell, e.g., a mammalian, an insect, a yeast, a bacterial, or an E. coli cell. The type of cell used is not particularly limited, as long as the O—RS and O-tRNA retain their orthogonality in the cell's environment.

The term "preferentially acylates" refers to an efficiency of, e.g., about 50% efficient, about 70% efficient, about 75% efficient, about 85% efficient, about 90% efficient, about 95% efficient, or about 99% or more efficient, at which an O—RS acylates an O-tRNA with an unnatural amino acid compared to an endogenous tRNA or amino acid of a translation system of interest. The unnatural amino acid is then incorporated in a growing polypeptide chain with high fidelity, e.g., at greater than about 75% efficiency for a given selector codon, at greater than about 80% efficiency for a given selector codon, at greater than about 90% efficiency for a given selector codon, at greater than about 95% efficiency for a given selector codon, or at greater than about 99% or more efficiency for a given selector codon.

The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as stop codons, e.g., amber, ochre, and opal codons; four or more base codons; codons derived from natural or unnatural base pairs and the like. For a given system, a selector codon can also include one of the natural three base codons (i.e. natural triplets), wherein the endogenous system does not use said natural triplet, e.g., a system that is lacking a tRNA that recognizes the natural triplet or a system wherein the natural triplet is a rare codon.

An anticodon has the reverse complement sequence of the corresponding codon.

An O-tRNA/O—RS pair is composed of an O-tRNA, e.g., a suppressor tRNA, or the like, and an O—RS.

A suppressor tRNA is a tRNA that alters the reading of a messenger RNA (mRNA) in a given translation system. A suppressor tRNA can read through, e.g., a stop codon, a four base codon, or a rare codon.

The O-tRNA is not acylated by endogenous synthetases and is capable of decoding a selector codon, as described herein. The O—RS recognizes the O-tRNA, e.g., with an extended anticodon loop, and preferentially acylates the O-tRNA with an unnatural amino acid.

The tRNA and the RS used in the processes of the invention can be naturally occurring or can be derived by mutation of a naturally occurring tRNA and/or RS from a variety of organisms. In various embodiments, the tRNA and RS are derived from at least one organism. In another embodiment, the tRNA is derived from a naturally occurring or mutated naturally occurring tRNA from a first organism and the RS is derived from naturally occurring or mutated naturally occurring RS from a second organism.

A suitable tRNA/RS pair may be selected from libraries of mutant tRNA and RS, e.g. based on the results of a library screening. Alternatively, a suitable tRNA/RS pair may be a heterologous tRNA/synthetase pair that is imported from a source species into the translation system. Preferably, the cell used as translation system is different from said source species.

For example a suitable orthogonal O-tRNA can be derived from an archaebacterium, such as *Methanococcus jannaschii, Methanobacterium thermoautotrophicum, Halobacterium* such as *Haloferax volcanii* and *Halobacterium* species NRC-I, *Archaeoglobus fulgidus, Pyrococcus furiosus, Pyrococcus horikoshii, Aeuropyrum pernix, Methanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like, or a eubacterium, such as *Escherichia coli, Thermus thermophilus, Bacillus subtilis, Bacillus stearothermphilus*, or the like, while the orthogonal O—RS can be derived from an organism or combination of organisms, e.g., an archaebacterium, such as *Methanococcus jannaschii, Methanobacterium thermoautotrophicum, Halobacterium* such as *Haloferax volcanii* and *Halobacterium* species NRC-J, *Archaeoglobus fulgidus, Pyrococcus furiosus, Pyrococcus horikoshii, Aeuropyrum pernix, Methanococcus maripaludis, Methanopyrus kandleri, Methanosarcina mazei, Methanosarcina bakeri; Methanosarcina hafniense; Pyrobaculum aerophilum, Pyrococcus abyssi, Sulfolobus solfataricus, Sulfolobus tokodaii, Thermoplasma acidophilum, Thermoplasma volcanium*, or the like, or a eubacterium, such as *Escherichia coli, Thermus thermophilus, Bacillus subtilis, Bacillus stearothermphilus*, or the like. In one embodiment, eukaryotic sources, e.g., plants, algae, protists, fungi, yeasts, animals, e.g., mammals, insects, arthropods, or the like can also be used as sources of O-tRNAs and O—RSs Methods for evolving tRNA/RS pairs are described, e.g., in WO 02/085923 and WO 02/06075.

Preferably, the RS is a pyrrolysyl tRNA synthetase (pylRS) capable of acylating a tRNA with the unnatural amino acid of the invention.

The pyrrolysyl tRNA synthetase used in methods of the invention may be a wildtype or a genetically engineered pylRS. Examples for wildtype pylRS include, but are not limited to pylRS from archaebacteria and eubacteria such as *Methanosarcina mazei, Methanosarcina barkeri, Methanococcoides burtonii, Methanosarcina acetivorans, Methanosarcina thermophila*, and *Desulfitobacterium hafniense*.

Genetically engineered pylRS have been described, for example, by Neumann et al. (Nat Chem Biol 4:232, 2008), by Yanagisawa et al. (Chem Biol 2008, 15:1187), and in EP2192185A1).

According to a particular embodiment, the pyrrolysyl tRNA synthetase used for preparation of polypeptides of the invention is wildtype pyrrolysyl tRNA synthetase from *M. mazei*.

According to a particular embodiment, the pyrrolysyl tRNA synthetase comprises the amino acid sequence of wildtype *M. mazei* pyrrolysyl tRNA synthetase set forth in SEQ ID NO:1, or a functional fragment thereof.

```
SEQ ID NO: 1:
MDKKPLNTLISATGLWMSRTGTIHKIKHHEVSRSKIYIEMACGDHLVVNNSRSSRTARAL      60

RHHKYRKTCKRCRVSDEDLNKFLTKANEDQTSVKVKVVSAPTRTKKAMPKSVARAPKPLE     120

NTEAAQAQPSGSKFSPAIPVSTQESVSVPASVSTSISSISTGATASALVKGNTNPITSMS     180

APVQASAPALTKSQTDRLEVLLNPKDEISLNSGKPFRELESELLSRRKKDLQQIYAEERE     240

NYLGKLEREITRFFVDRGFLEIKSPILIPLEYIERMGIDNDTELSKQIFRVDKNFCLRPM     300

LAPNLYNYLRKLDRALPDPIKIFEIGPCYRKESDGKEHLEEFTMLNFCQMGSGCTRENLE     360

SIITDFLNHLGIDFKIVGDSCMVYGDTLDVMHGDLELSSAVVGPIPLDREWGIDKPWIGA     420

GFGLERLLKVKHDFKNIKRAARSESYYNGISTNL                               454
```

According to another particular embodiment, the pyrrolysyl tRNA synthetase is pyrrolysyl tRNA synthetase from *M. mazei* comprising one or more than one amino acid alteration, preferably selected from amino acid substitutions Y306A and Y384F.

According to a particular embodiment, the pyrrolysyl tRNA synthetase comprises the amino acid sequence of mutant *M. mazei* pyrrolysyl tRNA synthetase set forth in SEQ ID NO:2, or a functional fragment thereof.

SEQ ID NO: 2:
```
MDKKPLNTLISATGLWMSRTGTIHKIKHHEVSRSKIYIEMACGDHLVVNNSRSSRTARAL    60
RHHKYRKTCKRCRVSDEDLNKFLTKANEDQTSVKVKVVSAPTRTKKAMPKSVARAPKPLE   120
NTEAAQAQPSGSKFSPAIPVSTQESVSVPASVSTSISSISTGATASALVKGNTNPITSMS   180
APVQASAPALTKSQTDRLEVLLNPKDEISLNSGKPFRELESELLSRRKKDLQQIYAEERE   240
NYLGKLEREITRFFVDRGFLEIKSPILIPLEYIERMGIDNDTELSKQIFRVDKNFCLRPM   300
LAPNLANYLRKLDRALPDPIKIFEIGPCYRKESDGKEHLEEFTMLNFCQMGSGCTRENLE   360
SIITDFLNHLGIDFKIVGDSCMVFGDTLDVMHGDLELSSAVVGPIPLDREWGIDKPWIGA   420
GFGLERLLKVKHDFKNIKRAARSESYYNGISTNL                            454
```

Any aminoacyl tRNA synthetase described herein may be used for acylation of a tRNA with the unnatural amino acids of the invention.

According to one aspect of the invention, wildtype *M. mazei* pyrrolysyl tRNA synthetase is used for acylation of a tRNA with a compound of formula

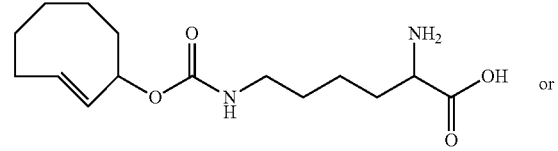 or

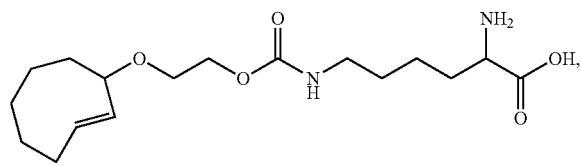

or a salt thereof.

According to a further aspect of the invention, wildtype *M. mazei* pyrrolysyl tRNA synthetase is used for acylation of a tRNA with a compound of formula

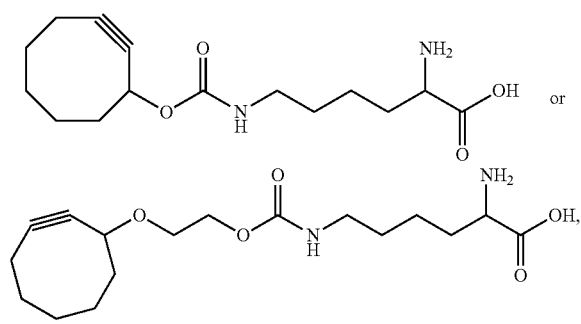

or a salt thereof.

According to another aspect of the invention, a mutant *M. mazei* pyrrolysyl tRNA synthetase comprising amino acid substitutions Y306A and Y384F is used for acylation of a tRNA with a compound of formula

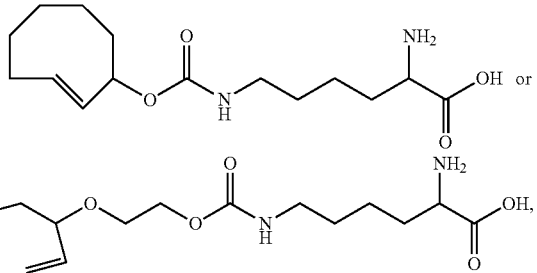

or a salt thereof.

According to another aspect of the invention, a mutant *M. mazei* pyrrolysyl tRNA synthetase comprising amino acid substitutions Y306A and Y384F is used for acylation of a tRNA with a compound of formula

or a salt thereof.

The tRNA which is used in combination with the pylRS (tRNA$^{pyl}$) may be a wildtype or a genetically engineered tRNA. Examples for wildtype tRNA$^{pyl}$ include, but are not limited to, tRNAs from archaebacteria and eubacteria, such as mentioned above, which facilitate translational incorporation of pyrrolysyl residues.

In a similar manner, suitable tRNA$^{Tyr}$/TyrRS and tRNA$^{Leu}$/leucyl-tRNA synthetase pairs can be provided and used.

Selector codons utilized in methods of the present invention expand the genetic codon framework of the protein biosynthetic machinery of the translation system used. For example, a selector codon includes, e.g., a unique three base codon, a nonsense codon, such as a stop codon, e.g., an amber codon, or an opal codon, an unnatural codon, at least a four base codon or the like. A number of selector codons can be introduced into a polynucleotide encoding a desired polypeptide (target polypeptide), e.g., one or more, two or more, more than three, etc.

The 64 genetic codons code for 20 amino acids and three stop codons. Because only one stop codon is needed for translational termination, the other two can in principle be used to encode nonproteinogenic amino acids. The amber stop codon, UAG, has been successfully used in in vitro biosynthetic system and in *Xenopus* oocytes to direct the incorporation of unnatural amino acids. Among the three stop codons, UAG is the least used stop codon in *E. coli*. Some *E. coli* strains contain natural suppressor tRNAs, which recognize UAG and insert a natural amino acid. In addition, these amber suppressor tRNAs have been used in conventional protein mutagenesis. In mammalian cells (HEK cells), the ochre (TAA) codon and the amber (TAG) codon have been used to incorporate two different unnatural amino acids into distinct sites of the same polypeptide. See, for instance, Han Xiao, et al., Angew Chem Int Ed Engl 2013, 52, 14080-14083.

In one embodiment, the methods of the invention involve the use of a selector codon that is a stop codon for the incorporation of a compound of the invention. For example, an O-tRNA is generated that recognizes the stop codon, preferably the amber stop codon, and is acylated by an O—RS with a compound of the invention. This O-tRNA is not recognized by the naturally occurring aminoacyl-tRNA synthetases. Conventional site-directed mutagenesis can be used to introduce the stop codon, e.g., the amber stop codon, at the site of interest into the polynucleotide sequence encoding the target polypeptide. When the O—RS, O-tRNA and the mutant gene are combined in a translation system, the unnatural amino acid is incorporated in response to the amber stop codon to give a polypeptide containing the unnatural amino acid analog, i.e. the compound of the invention, at the specified position(s).

The incorporation of the compounds of the invention in vivo can be done without significant perturbation of the host, e.g., an E. coli or HEK or HeLa cell. For example, because the suppression efficiency for the amber stop codon depends upon the competition between the O-tRNA, e.g., the amber suppressor tRNA, and the release factor 1 (RF1) (which binds to the amber stop codon and initiates release of the growing peptide from the ribosome), the suppression efficiency can be modulated by, e.g., either increasing the expression level of O-tRNA, e.g., the suppressor tRNA, or by using an RF1 deficient strain.

According to particular embodiment, the tRNA$^{pyl}$ used in processes of the invention comprises the CUA anticodon to the amber stop codon.

Other selector codons useful for encoding compounds of the invention are rare codons. For example, when the arginine concentration in an in vitro protein synthesis reaction is reduced, the rare arginine codon, AGG, has proven to be efficient for insertion of Ala by a synthetic tRNA acylated with alanine. In this case, the synthetic tRNA competes with the naturally occurring tRNA$^{Arg}$, which exists as a minor species in *E. coli*. Some organisms do not use all triplet codons. For example, an unassigned codon AGA in *Micrococcus luteus* has been utilized for insertion of amino acids in an in vitro transcription/translation extract. Accordingly, any triplet codon not used by the translation system applied in the processes of the invention can serve as selector codon.

A further alternative for incorporating UAAs according to the present invention into polypeptides is using a quadruplet (four-base) codon as a selector codon and a corresponding O-tRNA/RS pair.

The translation system is kept for a suitable time at conditions which allow formation of the polypeptide of the invention by a ribosome. mRNA that encodes the target polypeptide and comprises one or more than one selector codon is bound by the ribosome. Then, the polypeptide is formed by stepwise attachment of amino acids at positions encoded by codons which are bound the respective aminoacyl tRNAs. Thus, the compound of the invention is incorporated in the target polypeptide at the position(s) encoded by the selector codon(s).

Translation of the target polypeptide by a translation system may be effected by procedures well known in the art. To facilitate efficient translation, the components of the translation system may be mixed. Cells used as translation system are expediently cultured and kept in a suitable expression medium under conditions and for a time suitable to produce the target polypeptide. It may be required to induce expression by addition of a compound, such as arabinose, isopropyl β-D-thiogalactoside (IPTG) or tetracycline that allows transcription of the target polypeptide gene.

Optionally, after translation the polypeptide of the invention may be recovered from the translation system. For this purpose, the polypeptides of the invention can be recovered and purified, either partially or substantially to homogeneity, according to procedures known to and used by those of skill in the art. Standard procedures well known in the art include, e.g., ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. Antibodies made against the unnatural amino acid or the polypeptides of the invention can be used as purification reagents, i.e. for affinity-based purification of the polypeptides.

A variety of purification/protein folding methods are well known in the art, including, e.g., those set forth in Scopes, Protein Purification, Springer, Berlin (1993); and Deutscher, Methods in Enzymology Vol. 182: Guide to Protein Purification, Academic Press (1990); and the references cited therein.

As noted, those of skill in the art will recognize that, after synthesis, expression and/or purification, polypeptides can possess a conformation different from the desired conformations of the relevant polypeptides. For example, polypeptides produced by prokaryotic systems often are optimized by exposure to chaotropic agents to achieve proper folding. During purification from, e.g., lysates derived from *E. coli*, the expressed polypeptide is optionally denatured and then renatured. This is accomplished, e.g., by solubilizing the proteins in a chaotropic agent such as guanidine HCl. In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art. Polypeptides can be refolded in a redox buffer containing, e.g., oxidized glutathione and L-arginine.

It will be appreciated that while particular methods of constructing target polypeptide of the invention that comprise chemically reactive unnatural amino acids are detailed herein, e.g., using orthogonal translation systems, they should not necessarily be taken as limiting. Furthermore, other, e.g., non-orthogonal, methods of constructing target polypeptides having unnatural amino acids are also included herein in the many embodiments. Such methods are described in further detail herein.

In different embodiments of the invention, target polypeptides of the invention can be constructed via direct incorporation methods such as an orthogonal translation system. This represents a preferred embodiment, due to the ability of orthogonal systems to produce high yields of correctly folded and post-translationally modified polypeptides with site-specifically incorporated unnatural amino acids. Alternatively or additionally, however, other strategies for the direct incorporation of unnatural amino acids into a polypeptide chain can be employed to introduce first and second unnatural amino acids into the target polypeptides. For example, one general in vitro biosynthetic method for incorporating unnatural amino acids into, e.g., target polypeptides, during primary construction uses nonsense or frameshift suppressor tRNAs that have been chemically acylated with the desired unnatural amino acid and then added to an extract capable of supporting protein biosynthesis and which includes a gene containing a desired amber nonsense mutation. This strategy has been used to site-specifically incorporate over 100 unnatural amino acids into a variety of proteins of virtually any size and can be used herein to create target polypeptides that comprise unnatural amino acids. In other embodiments, unnatural amino acids can be directly incorporated into smaller target polypeptides (ranging from 60-100 amino acids) via chemical synthesis. Solid phase peptide synthesis is a method that is widely used to chemically synthesize peptides and small proteins that comprise unnatural amino acids (see, e.g., Merrifield (1963) "Solid Phase Peptide synthesis. I. The synthesis of a tetrapeptide." JACS 85: 2149-2154) and can be adapted to produce target polypeptides of the invention. This technique typically comprises two stages: The first stage solid phase peptide synthesis (SPPS) includes the assembly of a peptide chain using protected amino acid derivatives on a polymeric support via repeated cycles of coupling-deprotection. The free N-terminal amine of a solid-phase attached peptide can then be coupled to a single N-protected amino acid unit, e.g., an unnatural amino acid. This unit is then deprotected, revealing a new N-terminal amine to which a further amino acid may be attached. While the peptide is being synthesized usually by step-wise methods, all soluble reagents can be removed from the peptide-solid support matrix by filtration and washed away at the end of each coupling step. In the second stage of SPPS, the peptide is cleaved from the support and side-chain protecting groups are removed to produce the peptide, e.g., a target polypeptide comprising one or more unnatural amino acids. There are two major used forms of solid phase peptide synthesis: Fmoc (Carpino et al. (1972) "9-Fluorenylmethoxycarbonyl amino-protecting group." J Org Chem 37: 3404-3409), in which a base labile alpha-amino protecting group is used, and t-Boc, in which an acid labile protecting group is used. Each method involves different resins and amino acid side-chain protection and consequent cleavage/deprotection steps.

By means of the methods of the invention it is furthermore possible to introduce multiple labels into oligonucleotides obtained by synthesis. The amidites comprising the dienophiles of the invention required for this can be easily prepared. The oligonucleotide may have any length between 3 and 10000 nucleotides, preferably between 4 and 5000 nucleotides, more preferably between 5 and 1000 nucleotides or between 10 and 500 nucleotides, most preferably between 10 and 200 nucleotides. In a particular embodiment of the invention the oligonucleotide to be modified by the method of the present invention may have more than 50, preferably more than 100 nucleotides. The oligonucleotide according to the invention may by single-stranded or double-stranded DNA or RNA as well as nucleic acid analogs (e.g. PNA, LNA) or chimera of these with DNA and/or RNA.

Unnatural sugars comprising the dienophiles of the invention can be metabolically incorporated into glycans. For instance, neuraminic acid or N-acetyl mannosamine can be modified to comprise a dienophil of the invention and thus the methods of the invention allow multiple labeling of glycans into which the unnatural sugars comprising the dienophiles of the invention have been incorporated.

In a further application, the dienophiles of the invention can be functionalized to carry groups (e.g. trimethoxysilyl groups) which can be used for the synthesis of reactive solid phases. As a result, solid phases become accessible which carry both the first and the second dienophile. The applications following therefrom range from the chip technology for oligonucleotides, polypeptides or glycans to catalytic surfaces and solid phase reagents.

Quantum dots are understood to mean nanoparticles which are composed of compounds such as CdS or CdSe and have special optical properties. Excited by lasers they fluoresce very strongly as a function of their size and therefore are more and more widely used in the diagnostic field especially since they enable the detection of individual molecules. However, a precondition for this is their doping with functional groups, which proceeds via SH groups and permits a subsequent interaction with the molecules to be detected.

Moreover, gold nanoparticles are considered for electron microscopic investigations of biomolecules on account of their special properties. The anchorage of molecules on the surface is accomplished via SH groups, too.

The methods of the invention can be used to link molecules to their surface. To this end, SH group-containing dienophile can be produced. Usually, the corresponding disulfides are produced and then the mercapto compound can be prepared therefrom by reduction with dithiothreitol. The disulfides as such can be anchored to gold surfaces. Thus, the dienophiles can be attached to the surface of quantum dots or other metals. For example, antibodies, saccharides or therapeutic agents can be anchored on the surface of the quantum dots for diagnostic or therapeutic purposes.

Kits of the invention may in particular be used for preparing polypeptides of the invention. To this end, the kits may comprise one or more means for preparing a polypeptide. Such means include, but are not limited to i) an aminoacyl tRNA synthetase, or a polynucleotide encoding it;

ii) a tRNA as described herein, or a polynucleotide encoding it.

Both the aminoacyl tRNA synthetase and the tRNA may, for example, be provided in the form of one or more than one expression vector for said aminoacyl tRNA synthetase and corresponding tRNA.

Such kit may also comprise a polynucleotide encoding a reporter protein, for example an expression vector for, e.g., GFP, wherein the polynucleotide sequence coding for said reporter protein comprises an amber stop codon. Such reporter protein encoding polynucleotide may serve as a positive control to confirm expression of a polypeptide with cyclooctynyl or trans-cyclooctenyl analog group(s).

Further, such kit may comprise further means for translation of a polynucleotide encoding said polypeptide, for example a translation system, such as *E. coli* cells, HeLa cells, *E. coli* extract, wheat germ extract, or rabbit reticulocyte lysate, and instructions for use.

It will be appreciated by those skilled in the art that the reactions of the invention need to be carried out in reverse order if the reaction of the first tetrazine with the first dienophile is to proceed in the presence of the second tetrazine. Thus, the present invention further relates to methods for forming linkages by cycloaddition reactions, wherein the method comprises reacting a first tetrazine with a first dienophile followed by reacting a second tetrazine with a second dienophile, wherein the reaction of the first tetrazine with the first dienophile proceeds in the presence of the second tetrazine, wherein (i) the first tetrazine comprises a group of the formula:

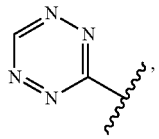 [SMILES: *c1nncnn1]

(ii) the first dienophile comprises a cyclooctynyl group of the formula:

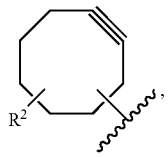

wherein $R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^c$, $R^d$ independently are hydrogen or $C_2$-$C_5$-alkanoyloxymethyl (iii) the second tetrazine comprises a group of the formula:

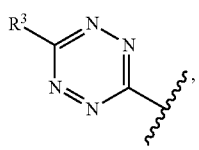

wherein $R^3$ is $C_1$-$C_3$-alkyl; and (iv) the second dienophile comprises a trans-cyclooctenyl group of the formula:

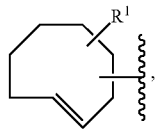

wherein $R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^a$, $R^b$ independently are hydrogen or $C_2$-$C_5$-alkanoyloxymethyl.

Specific aspects and embodiments for this method can be directly derived from the disclosure herein which can be applied in an analogous manner to this reverse order method. It is noted that the methods of the invention which comprise the reactions in reverse order may be particularly suitable for applications where it is preferred to have the first and the second tetrazine in place prior to reacting them with the dienophiles. This may be the case for certain applications in non-biological systems, e.g. the labeling of surfaces, where there is more freedom to appropriately choose conditions so as to take the properties of the tetrazines into account.

In summary, the present invention relates in particular to the following embodiments E1 to E110:

E1. A method for forming linkages by cycloaddition reactions, wherein the method comprises reacting a first tetrazine with a first dienophile followed by reacting a second tetrazine with a second dienophile, wherein the reaction of the first tetrazine with the first dienophile proceeds in the presence of the second dienophile, wherein (i) the first tetrazine comprises a group of the formula:

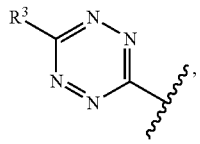

wherein $R^3$ is $C_1$-$C_3$-alkyl;

(ii) the first dienophile comprises a trans-cyclooctenyl group of the formula:

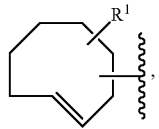

wherein $R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di- ($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^a$, $R^b$ independently are hydrogen or $C_2$-$C_5$-alkanoyloxymethyl, (iii) the second tetrazine comprises a group of the formula:

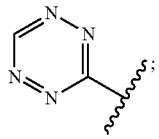

and (iv) the second dienophile comprises a cyclooctynyl group of the formula:

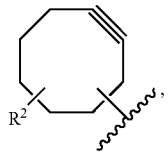

wherein $R^2$ is hydrogen, halogen, $C_1$-$C_4$-alkyl, ($R^cO$)$_2$P(O)O—$C_1$-$C_4$-alkyl, ($R^dO$)$_2$P(O)—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^c$, $R^d$ independently are hydrogen or $C_2$-$C_5$-alkanoyloxymethyl.

E2. The method of embodiment E1, wherein the first tetrazine preferentially reacts with the first dienophile in the presence of the second dienophile.

E3. The method of embodiment E1 or E2, wherein the rate constant k of the first tetrazine with the first dienophile is usually at least $10^2$-times higher than the rate constant k of the reaction of the first tetrazine with the second dienophile.

E4. The method of any one of embodiments E1-E3, wherein the rate constant k of the first tetrazine with the first dienophile is allowed to proceed for 30 minutes or less at a temperature of about 37° C.

E5. The method of any one of embodiments E1-E4, wherein the method comprises contacting a target molecule or a target molecule composition with (i) a first labeling agent comprising a group of the formula:

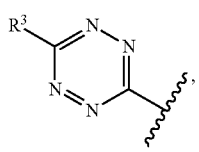

wherein $R^3$ is $C_1$-$C_3$-alkyl; followed by (ii) a second labeling agent comprising a group of the formula:

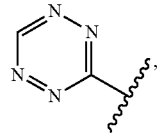

wherein the target molecule comprises (i) a trans-cyclooctenyl group of the formula:

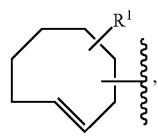

wherein $R^1$ is hydrogen, halogen, $C_1$-$C_4$-alkyl, ($R^aO$)$_2$P(O)O—$C_1$-$C_4$-alkyl, ($R^bO$)$_2$P(O)—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino;

$R^a$, $R^b$ independently are hydrogen or $C_2$-$C_5$-alkanoyloxymethyl; and (ii) a cyclooctynyl group of the formula:

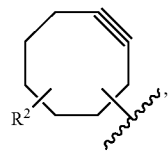

wherein $R^2$ is hydrogen, halogen, $C_1$-$C_4$-alkyl, ($R^cO$)$_2$P(O)O—$C_1$-$C_4$-alkyl, ($R^dO$)$_2$P(O)—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino;

$R^c$, $R^d$ independently are hydrogen or $C_2$-$C_5$-alkanoyloxymethyl, wherein the target molecule composition comprises (i) a first target molecule comprising a trans-cyclooctenyl group of the formula:

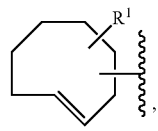

wherein $R^1$ is hydrogen, halogen, $C_1$-$C_4$-alkyl, ($R^aO$)$_2$P(O)O—$C_1$-$C_4$-alkyl, ($R^bO$)$_2$P(O)—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino;

$R^a$, $R^b$ independently are hydrogen or $C_2$-$C_5$-alkanoyloxymethyl; and (ii) a second target molecule comprising a cyclooctynyl group of the formula:

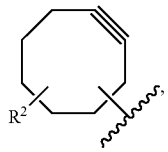

wherein $R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino;

$R^c$, $R^d$ independently are hydrogen or $C_2$-$C_5$-alkanoyloxymethyl.

E6. The method of any one of embodiments E1-E5, wherein the first tetrazine or labeling agent comprises a group of the formula:

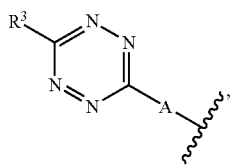

wherein $R^3$ is $C_1$-$C_3$-alkyl and A is 1,4-phenylene or $C_1$-$C_6$-alkylene.

E7. The method of any one of embodiments E1-E6, wherein the first tetrazine or labeling agent comprises a group of the formula:

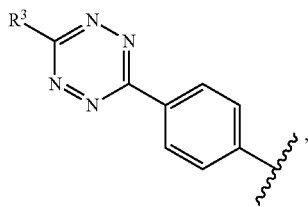

wherein $R^3$ is $C_1$-$C_3$-alkyl.

E8. The method of any one of embodiments E1-E7, wherein $R^3$ is methyl.

E9. The method of any one of embodiments E1-E8, wherein the second tetrazine or labeling agent comprises a group of the formula:

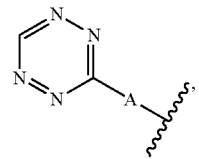

wherein A is 1,4-phenylene or $C_1$-$C_6$-alkylene.

E10. The method of any one of embodiments E1-E9, wherein the second tetrazine or labeling agent comprises a group of the formula:

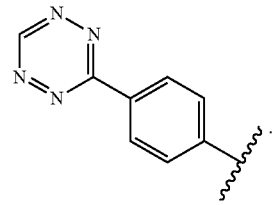 [SMILES: *c1ccc(-c2nncnn2)cc1]

E11. The method of any one of embodiments E1-E10, wherein the labeling agent comprises a label selected from the group consisting of dyes, radiolabels, MRI-sensitive spin labels, affinity tags, pegylation groups and bioactive compounds.

E12. The method of embodiment E11, wherein the dyes are selected from the group consisting of fluorescent, luminescent, and phosphorescent dyes.

E13. The method of embodiment E11, wherein the dyes are selected from the group consisting of dansyl, coumarin, fluorescein, acridine, rhodamine, silicon-rhodamine, BODIPY, and cyanine dyes.

E14. The method of embodiment E11, wherein the affinity tags are selected from the group consisting of biotin, His-tag, Flag-tag, strep-tag, sugars, lipids, sterols, PEG-linkers, benzylguanines, benzylcytosines, and co-factors.

E15. The method of embodiment E11, wherein the radiolabels are selected from the group consisting of radioactive forms of hydrogen, fluorine, carbon, phosphorous, sulphur, and iodine, including tritium, fluorine-18, carbon-11, carbon-14, phosphorous-32, phosphorous-33, sulphur-33, sulphur-35, iodine-123, and iodine-125.

E16. The method of embodiment E11, wherein the bioactive compounds are selected from cytotoxic compounds; antiviral compounds; biological response modifiers; microtubule affecting agents; hormone modulators; steroidal compounds.

E17. The method of any one of embodiments E1-E16, wherein the trans-cyclooctenyl group is a group of the formula:

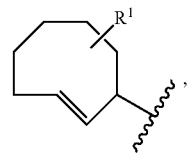

wherein $R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino;

$R^a$, $R^b$ independently are hydrogen or $C_2$-$C_5$-alkanoyloxymethyl.

E18. The method of any one of embodiments E17, wherein $R^1$ is hydrogen.

E19. The method of any one of embodiments E1-E18, wherein the trans-cyclooctenyl group is linked to an amino acid residue.

E20. The method of any one of embodiments E1-E19, wherein the cyclooctynyl group is a group of the formula:

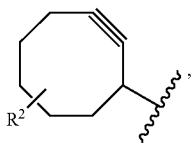

wherein
$R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino;

$R^c$, $R^d$ independently are hydrogen or $C_2$-$C_5$-alkanoyloxymethyl.

E21. The method of any one of embodiments E1-E20, wherein $R^2$ is hydrogen.

E22. The method of any one of embodiments E1-E21, wherein the cyclooctynyl group is linked to an amino acid residue.

E23. The method of any one of embodiments E1-E22, wherein the trans-cyclooctenyl group has the formula:

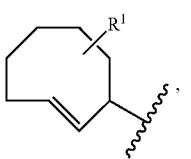

wherein
$R^1$ is hydrogen; and
the first tetrazine or labeling agent comprises a group of the formula:

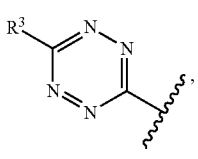

wherein
$R^3$ is methyl.

E24. The method of any one of embodiments E1-E23, wherein the cyclooctynyl group has the formula:

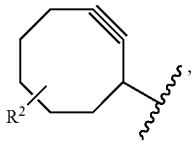

wherein
$R^2$ is hydrogen; and
the second tetrazine or labeling agent comprises a group of the formula:

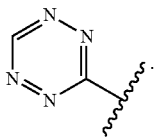

E25. The method of any one of embodiments E1-E24, wherein the first tetrazine or labeling agent reacts with the trans-cyclooctenyl groups.

E26. The method of any one of embodiments E1-E25, wherein the first tetrazine or labeling agent is reacted with the first dienophile or the target molecule or target molecule composition under conditions that do not allow the first labeling agent to substantially react with the cyclooctynyl groups.

E27. The method of any one of embodiments E1-E26, wherein the first dienophile or the target molecule or target molecule composition is reacted with the first tetrazine or labeling agent under conditions that allow for substantially all trans-cyclooctenyl groups to react prior to reacting the second dienophile or the target molecule or target molecule composition with the second tetrazine or labeling agent.

E28. The method of any one of embodiments E1-E27, wherein the first dienophile or the target molecule or target molecule composition is reacted with a molar excess of the first tetrazine or labeling agent based on the trans-cyclooctenyl groups.

E29. The method of any one of embodiments E1-E28, wherein unreacted first tetrazine or labeling agent is removed prior to reacting the second dienophile or the target molecule or target molecule composition with the second tetrazine or labeling agent.

E30. The method of any one of embodiments E1-E29, wherein unreacted trans-cyclooctenyl groups are reacted with a quencher prior to reacting the second dienophile or the target molecule or target molecule composition with the second tetrazine or labeling agent.

E31. The method of embodiment E30, wherein the quencher is a compound of the formula:

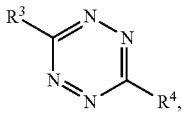

or an acid addition salt thereof, wherein
$R^3$ is $C_1$-$C_3$-alkyl; and
$R^4$ is an organic radical.

E32. The method of embodiment E31, wherein the quencher is (4-(6-methyl-1,2,4,5-tetrazine-3-yl)phenyl)methanamine or an acid addition salt thereof.

E33. The method of any one of embodiments E30-E32, wherein unreacted quencher is removed from the composition prior to reacting the second dienophile or the target molecule or target molecule composition with the second tetrazine or labeling agent.

E34. The method of any one of embodiments E1-E33, wherein the composition is a biological system.

E35. The method of embodiment E34, wherein the biological system is an organism or a biological sample.

E36. The method of embodiment E34 or E35, wherein the biological sample comprises a cell.

E37. The method of any one of embodiments E1-E36, wherein the target molecule is selected from the group consisting of polypeptides, oligonucleotides, glycans, and lipids.

E38. The method of any one of embodiments E1-E37, wherein the trans-cyclooctenyl group is an axial isomer of the group of the formula:

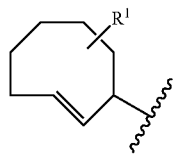

wherein $R^1$ is as defined in any one of embodiments E1-E37.

E39. A kit comprising
(i) a first tetrazine comprising a group of the formula:

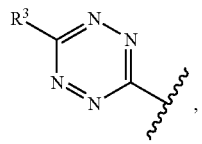

wherein
$R^3$ is $C_1$-$C_3$-alkyl; and
(ii) a second tetrazine comprising a group of the formula:

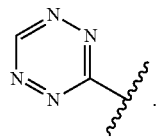 [SMILES: *c1nncnn1]

E40. A kit comprising
(i) a first modifying agent comprising a trans-cyclooctenyl group of the formula:

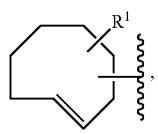

wherein
$R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^a$, $R^b$ independently are hydrogen or $C_2$-$C_5$-alkanoyloxymethyl; and (ii) a second modifying agent comprising a cyclooctynyl group of the formula:

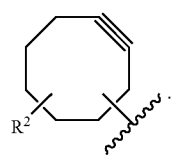

wherein
$R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^c$, $R^d$ independently are hydrogen or $C_2$-$C_5$-alkanoyloxymethyl.

E41. The kit of embodiment E40, wherein the first modifying agent is an unnatural amino acid or an analogue thereof.

E42. The kit of embodiment E40 or E41, wherein the second modifying agent is an unnatural amino acid or an analogue thereof.

E43. The kit of embodiment E40, wherein the first modifying agent is an unnatural nucleotide or an analogue thereof.

E44. The kit of embodiment E40 or E43, wherein the second modifying agent is an unnatural nucleotide or an analogue thereof.

E45. The kit of embodiment E40, wherein the first modifying agent is an unnatural glycan or an analogue thereof.

E46. The kit of embodiment E40 or E45, wherein the second modifying agent is an unnatural glycan or an analogue thereof.

E47. The kit of any one of embodiments E40-E46, wherein the trans-cyclooctenyl group is an axial isomer of the group of the formula:

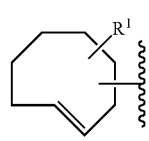

wherein R1 is as defined in any one of embodiments E40-E46.

E48. A cell comprising (i) a trans-cyclooctenyl group of the formula:

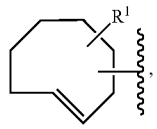

wherein

R$^1$ is hydrogen, halogen, C$_1$-C$_4$-alkyl, (R$^a$O)$_2$P(O)O—C$_1$-C$_4$-alkyl, (R$^b$O)$_2$P(O)—C$_1$-C$_4$-alkyl, CF$_3$, CN, hydroxyl, C$_1$-C$_4$-alkoxy, —O—CF$_3$, C$_2$-C$_5$-alkenoxy, C$_2$-C$_5$-alkanoyloxy, C$_1$-C$_4$-alkylaminocarbonyloxy or C$_1$-C$_4$-alkylthio, C$_1$-C$_4$-alkylamino, Di-(C$_1$-C$_4$-alkyl)amino, C$_2$-C$_5$-alkenylamino, C$_2$-C$_5$-alkenyl-C$_1$-C$_4$-alkyl-amino or Di-(C$_2$-C$_5$-alkenyl)amino; and R$^a$, R$^b$ independently are hydrogen or C$_2$-C$_5$-alkanoyloxymethyl;

and (ii) a cyclooctynyl group of the formula:

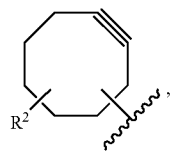

wherein

R$^2$ is hydrogen, halogen, C$_1$-C$_4$-alkyl, (R$^c$O)$_2$P(O)O—C$_1$-C$_4$-alkyl, (R$^d$O)$_2$P(O)—C$_1$-C$_4$-alkyl, CF$_3$, CN, hydroxyl, C$_1$-C$_4$-alkoxy, —O—CF$_3$, C$_2$-C$_5$-alkenoxy, C$_2$-C$_5$-alkanoyloxy, C$_1$-C$_4$-alkylaminocarbonyloxy or C$_1$-C$_4$-alkylthio, C$_1$-C$_4$-alkylamino, Di-(C$_1$-C$_4$-alkyl)amino, C$_2$-C$_5$-alkenylamino, C$_2$-C$_5$-alkenyl-C$_1$-C$_4$-alkyl-amino or Di-(C$_2$-C$_5$-alkenyl)amino; and R$^c$, R$^d$ independently are hydrogen or C$_2$-C$_5$-alkanoyloxymethyl.

E49. The cell of embodiment E48, which is a mammalian cell.

E50. The cell of embodiment E48 or E49, wherein the trans-cyclooctenyl group is attached to a polypeptide.

E51. The cell of any one of embodiments E48-E50, wherein the cyclooctynyl group is attached to a polypeptide.

E52. The cell of any one of embodiments E48-E51, wherein the cyclooctynyl group and the trans-cyclooctenyl group are attached to the same polypeptide.

E53. The cell of any one of embodiments E48-E51, wherein the cyclooctynyl group is attached to a first polypeptide and the trans-cyclooctenyl group is attached to a second polypeptide, the first and the second polypeptide being different polypeptides.

E54. The cell of any one of embodiments E48-E53, wherein the trans-cyclooctenyl group is an axial isomer of the group of the formula:

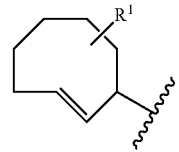

wherein R$^1$ is as defined in any one of embodiments E48-E53.

E55. A method for preparing the cell of any one of embodiments E48-E53, which comprises a) providing a cell comprising:
   (i) a first aminoacyl tRNA synthetase, or a polynucleotide encoding it; and optionally a second aminoacyl tRNA synthetase, or a polynucleotide encoding it;
   (ii) a first tRNA having an anticodon to a first selector codon, or a polynucleotide encoding said tRNA; and optionally a second tRNA having an anticodon to a second selector codon, or a polynucleotide encoding said tRNA; and
   (iii) a polynucleotide encoding a target polypeptide and comprising one or more than one first and second selector codon(s); or a first polynucleotide encoding a first target polypeptide and comprising one or more than one first selector codon(s) and a second polynucleotide encoding a second target polypeptide and comprising one or more than one second selector codon(s), wherein said first aminoacyl tRNA synthetase (i) is capable of acylating the first tRNA (ii) with a first unnatural amino acid or an analogue thereof comprising a trans-cyclooctenyl group of the formula:

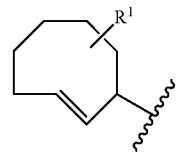

wherein

R$^1$ is hydrogen, halogen, C$_1$-C$_4$-alkyl, (R$^a$O)$_2$P(O)O—C$_1$-C$_4$-alkyl, (R$^b$O)$_2$P(O)—C$_1$-C$_4$-alkyl, CF$_3$, CN, hydroxyl, C$_1$-C$_4$-alkoxy, —O—CF$_3$, C$_2$-C$_5$-alkenoxy, C$_2$-C$_5$-alkanoyloxy, C$_1$-C$_4$-alkylaminocarbonyloxy or C$_1$-C$_4$-alkylthio, C$_1$-C$_4$-alkylamino, Di-(C$_1$-C$_4$-alkyl)amino, C$_2$-C$_5$-alkenylamino, C$_2$-C$_5$-alkenyl-C$_1$-C$_4$-alkyl-amino or Di-(C$_2$-C$_5$-alkenyl)amino; and R$^a$, R$^b$ independently are hydrogen or C$_2$-C$_5$-alkanoyloxymethyl, and with a second unnatural amino acid or an analogue thereof comprising a cyclooctynyl group of the formula:

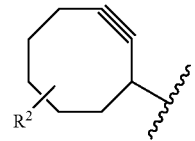

wherein

R² is hydrogen, halogen, C₁-C₄-alkyl, (RᶜO)₂P(O)O—C₁-C₄-alkyl, (RᵈO)₂P(O)—C₁-C₄-alkyl, CF₃, CN, hydroxyl, C₁-C₄-alkoxy, —O—CF₃, C₂-C₅-alkenoxy, C₂-C₅-alkanoyloxy, C₁-C₄-alkylaminocarbonyloxy or C₁-C₄-alkylthio, C₁-C₄-alkylamino, Di-(C₁-C₄-alkyl)amino, C₂-C₅-alkenylamino, C₂-C₅-alkenyl-C₁-C₄-alkyl-amino or Di-(C₂-C₅-alkenyl)amino; and Rᶜ, Rᵈ independently are hydrogen or C₂-C₅-alkanoyloxymethyl;

or wherein said first aminoacyl tRNA synthetase (i) is capable of acylating the first tRNA (ii) with a first unnatural amino acid or an analogue thereof comprising a trans-cyclooctenyl group of the formula:

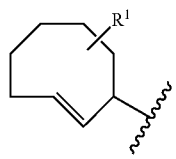

wherein

R¹ is hydrogen, halogen, C₁-C₄-alkyl, (RᵃO)₂P(O)O—C₁-C₄-alkyl, (RᵇO)₂P(O)—C₁-C₄-alkyl, CF₃, CN, hydroxyl, C₁-C₄-alkoxy, —O—CF₃, C₂-C₅-alkenoxy, C₂-C₅-alkanoyloxy, C₁-C₄-alkylaminocarbonyloxy or C₁-C₄-alkylthio, C₁-C₄-alkylamino, Di-(C₁-C₄-alkyl)amino, C₂-C₅-alkenylamino, C₂-C₅-alkenyl-C₁-C₄-alkyl-amino or Di-(C₂-C₅-alkenyl)amino; and Rᵃ, Rᵇ independently are hydrogen or C₂-C₅-alkanoyloxymethyl, and said second aminoacyl tRNA synthetase (i) is capable of acylating the second tRNA (ii) with a second unnatural amino acid or an analogue thereof comprising a cyclooctynyl group of the formula:

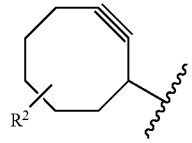

wherein

R² is hydrogen, halogen, C₁-C₄-alkyl, (RᶜO)₂P(O)O—C₁-C₄-alkyl, (RᵈO)₂P(O)—C₁-C₄-alkyl, CF₃, CN, hydroxyl, C₁-C₄-alkoxy, —O—CF₃, C₂-C₅-alkenoxy, C₂-C₅-alkanoyloxy, C₁-C₄-alkylaminocarbonyloxy or C₁-C₄-alkylthio, C₁-C₄-alkylamino, Di-(C₁-C₄-alkyl)amino, C₂-C₅-alkenylamino, C₂-C₅-alkenyl-C₁-C₄-alkyl-amino or Di-(C₂-C₅-alkenyl)amino; and Rᶜ, Rᵈ independently are hydrogen or C₂-C₅-alkanoyloxymethyl;

b) contacting the cell with the first and the second unnatural amino acid or an analogue thereof; and c) allowing translation of the polynucleotide(s) (iii) thereby incorporating the first and the second unnatural amino acids or the analogues thereof into the target polypeptide(s) at the position(s) encoded by the selector codon(s).

E56. The method of embodiment E55, wherein the cell is contacted with the first and the second unnatural amino acids or the analogues thereof sequentially.

E57. The method of embodiment E53, which comprises
a) contacting the cell with the first unnatural amino acid or the analogue thereof; and
b) allowing translation of the polynucleotide (iii) thereby incorporating the first unnatural amino acid or the analogue thereof into the target polypeptide at the position(s) encoded by the selector codon(s);
c) contacting the cell with the second unnatural amino acid or the analogue thereof; and
d) allowing translation of the polynucleotide (iii) thereby incorporating the second unnatural amino acid or the analogue thereof into the target polypeptide at the position(s) encoded by the selector codon(s).

E58. The method of any one of embodiments E55-E57, wherein the first unnatural amino acid or the analogue thereof is a compound of the formula:

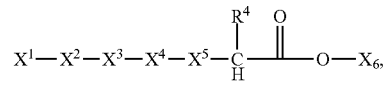

wherein:

X¹ has the formula:

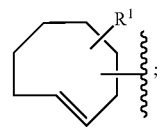

R¹ is hydrogen, halogen, C₁-C₄-alkyl, (RᵃO)₂P(O)O—C₁-C₄-alkyl, (RᵇO)₂P(O)—C₁-C₄-alkyl, CF₃, CN, hydroxyl, C₁-C₄-alkoxy, —O—CF₃, C₂-C₅-alkenoxy, C₂-C₅-alkanoyloxy, C₁-C₄-alkylaminocarbonyloxy or C₁-C₄-alkylthio, C₁-C₄-alkylamino, Di-(C₁-C₄-alkyl) amino, C₂-C₅-alkenylamino, C₂-C₅-alkenyl-C₁-C₄-alkyl-amino or Di-(C₂-C₅-alkenyl)amino;

Rᵃ, Rᵇ independently are hydrogen or C₂-C₅-alkanoyloxymethyl;

X² is —CH₂—, —O—, —S—, —NH—, —C(O)—, —OC(O)—, —C(O)O—, —NH—C(O)— or —C(O)—NH—;

X³ is C₁-C₆-alkylene, —(CH₂—CH₂—O)ₘ—, —(CH₂—O)ₚ— or a single bond;

X⁴ is —NH—, —C(O)—NH—, —NH—C(O)—, —NH—CH(NH₂)—, —CH(NH₂)—NH—, —NH—C(NH)—NH—, —C(O)—NH—CH(NH₂)—, —C(O)—NH—C(NH)—NH—, NH—CH(NH₂)—C(O)— or —NH—C(NH)—NH—C(O)—;

X⁵ is —(CH₂)ₙ— or phenylene-CH₂—;

X⁶ is hydrogen, C₁-C₆-alkyl, C₁-C₆-alkoxy-C₁-C₂-alkyl, C₂-C₇-alkanoyloxy-C₁-C₂-alkyl or C₂-C₇-alkanoylsulfanyl-C₁-C₂-alkyl;

R⁴ is —OH or —NH₂;

n is an integer from 1 to 4;

m is an integer from 1 to 6; and p is an integer from 1 to 6, or an acid or base addition salt thereof.

E59. The method of any one of embodiments E55-E58, wherein the second unnatural amino acid or the analogue thereof is a compound of the formula:

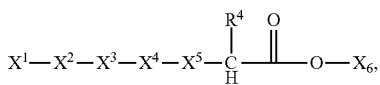

wherein:
$X^1$ has the formula:

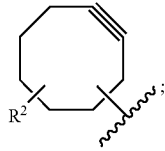

$R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, $CN$, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino;

$R^c$, $R^d$ independently are hydrogen or $C_2$-$C_5$-alkanoyloxymethyl;

$X^2$ is —$CH_2$—, —O—, —S—, —NH—, —C(O)—, —OC(O)—, —C(O)O—, —NH—C(O)— or —C(O)—NH—;

$X^3$ is $C_1$-$C_6$-alkylene, —($CH_2$—$CH_2$—O)$_m$—, —($CH_2$—O)$_p$— or a single bond;

$X^4$ is —NH—, —C(O)—NH—, —NH—C(O)—, —NH—CH($NH_2$)—, —CH($NH_2$)—NH—, —NH—C(NH)—NH—, —C(O)—NH—CH($NH_2$)—, —C(O)—NH—C(NH)—NH—, NH—CH($NH_2$)—C(O)— or —NH—C(NH)—NH—C(O)—;

$X^5$ is —($CH_2$)$_n$— or phenylene-$CH_2$—;

$X^6$ is hydrogen, $C_1$-$C_6$-alkyl, $C_1$-$C_6$-alkoxy-$C_1$-$C_2$-alkyl, $C_2$-$C_7$-alkanoyloxy-$C_1$-$C_2$-alkyl or $C_2$-$C_7$-alkanoylsulfanyl-$C_1$-$C_2$-alkyl;

$R^4$ is —OH or —$NH_2$;

n is an integer from 1 to 4;

m is an integer from 1 to 6; and p is an integer from 1 to 6, or an acid or base addition salt thereof.

E60. The method of embodiment E58 or E59, wherein $X^2$ is —O—.

E61. The method of any one of embodiments E58-E60, wherein $X^3$ is —$CH_2$—$CH_2$—O— or a single bond.

E62. The method of any one of embodiments E58-E61, wherein the structural element —$X^2$-$X^3$— comprises from 1 to 6 atoms in the main chain.

E63. The method of any one of embodiments E58-E62, wherein $X^4$ is —NH—, —C(O)—NH—, —NH—CH($NH_2$)—, —NH—C(NH)—NH—, —C(O)—NH—CH($NH_2$)— or —C(O)—NH—C(NH)—NH—.

E64. The method of any one of embodiments E58-E63, wherein $X^4$ is —C(O)—NH—.

E65. The method of any one of embodiments E55-E64, wherein n is 3 or 4.

E66. The method of any one of embodiments E58-E65, wherein the structural element —$X^2$-$X^3$-$X^4$—($CH_2$)$_n$— comprises from 5 to 12 atoms in the main chain, such as 6, 7, 8, 9, 10 or 11 atoms in the main chain.

E67. The method of any one of embodiments E58-E66, wherein $X^6$ is hydrogen, $C_1$-$C_6$-alkoxymethyl, $C_1$-$C_6$-alkoxyeth-1-yl, $C_2$-$C_7$-alkanoyloxymethyl or $C_2$-$C_7$-alkanoylsulfanylethyl.

E68. The method of any one of embodiments E58-E66, wherein $X^6$ is hydrogen.

E69. The method of any one of embodiments E58-E68, wherein the compound has S-configuration with regard to the asymmetric carbon atom carrying $R^4$.

E70. The method of any one of embodiments E58-E69, wherein —$X^5$—$CHR^4$—C(O)O—$X^6$ has formula:

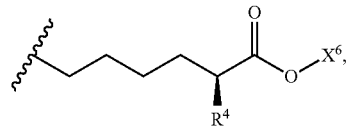

wherein $R^4$ and $X^6$ are as defined in any one of embodiments E58-E69.

E71. The method of any one of embodiments E58-E69, wherein —$X^5$—$CHR^4$—C(O)O—$X^6$ has formula:

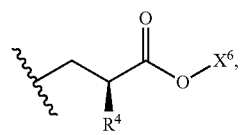

wherein $R^4$ and $X^6$ are as defined in any one of embodiments E58-E69.

E72. The method of any one of embodiments E58-E69, wherein —$X^5$—$CHR^4$—C(O)O—$X^6$ has formula:

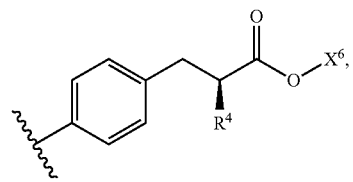

wherein $R^4$ and $X^6$ are as defined in any one of embodiments E58-E69.

E73. The method of any one of embodiments E55-E57, wherein the first unnatural amino acid is compound of the formula:

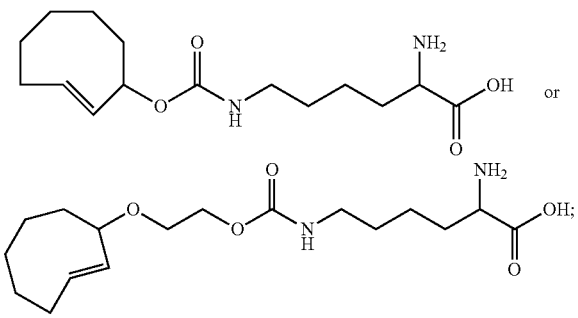

or an acid or base addition salt thereof.

E74. The method of embodiment E73, wherein the first unnatural amino acid is an axial isomer with respect to its trans-cyclooctenyl group.

E75. The method of any one of embodiments E55-E57, E73 and E74, wherein the second unnatural amino acid is compound of the formula:

[structure]

or

[structure]

or an acid or base addition salt thereof.

E76. The method of any one of embodiments E55-E75, wherein said translation system is a cell expressing said aminoacyl tRNA synthetase(s).

E77. The method of embodiment E76, wherein said aminoacyl tRNA synthetase is a pyrrolysyl tRNA synthetase.

E78. The method of embodiment E77, wherein said pyrrolysyl tRNA synthetase comprises the amino acid sequence set forth in SEQ ID NO:1 or 2.

E79. The method of any one of embodiments E55-E72 and E75-E78, wherein the trans-cyclooctenyl group is an axial isomer of the group of the formula:

[structure]

wherein $R^1$ is as defined in any one of embodiments E55-E72 and E75-E78.

E80. A polypeptide comprising
(i) a trans-cyclooctenyl group of the formula:

[structure]

wherein
$R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino;
$R^a$, $R^b$ independently are hydrogen or $C_2$-$C_5$-alkanoyloxymethyl;

and
(ii) a cyclooctynyl group of the formula:

[structure]

wherein
$R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl) amino;
$R^c$, $R^d$ independently are hydrogen or $C_2$-$C_5$-alkanoyloxymethyl.

E81. The polypeptide of embodiment E80, comprising a residue of the formula:

[structure: $X^1$—$X^2$—$X^3$—$X^4$—$X^5$—CH(Z^1)—C(O)—]

wherein:
$X^1$ has the formula

[structure]

$R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl) amino, $C_2$-$C_5$-alkenylamino, $C_2$-$C_5$-alkenyl-$C_1$-$C_4$-alkyl-amino or Di-($C_2$-$C_5$-alkenyl)amino;
$R^a$, $R^b$ independently are hydrogen or $C_2$-$C_5$-alkanoyloxymethyl;
$X^2$ is —$CH_2$—, —O—, —S—, —NH—, —C(O)—, —OC(O)—, —C(O)O—, —NH—C(O)— or —C(O)—NH—;
$X^3$ is $C_1$-$C_6$-alkylene, —($CH_2$—$CH_2$—O)$_m$—, —($CH_2$—O)$_p$— or a single bond;
$X^4$ is —NH—, —C(O)—NH—, —NH—C(O)—, —NH—CH($NH_2$)—, —CH($NH_2$)—NH—, —NH—C(NH)—NH—, —C(O)—NH—CH($NH_2$)—, —C(O)—NH—C(NH)—NH—, NH—CH($NH_2$)—C(O)— or —NH—C(NH)—NH—C(O)—;
$X^5$ is —($CH_2$)$_n$— or phenylene-$CH_2$—;
$Z^1$ is —O— or NH—;
n is an integer from 1 to 4;
m is an integer from 1 to 6; and
p is an integer from 1 to 6, and a residue of the formula:

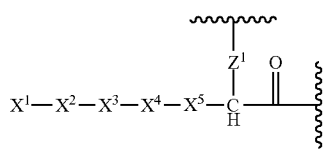

wherein:

$X^1$ has the formula:

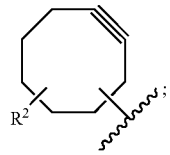

$R^2$ is hydrogen, halogen, $C_1$-$C_4$-alkyl, $(R^cO)_2P(O)O$—$C_1$-$C_4$-alkyl, $(R^dO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino;

$R^c$, $R^d$ independently are hydrogen or $C_2$-$C_5$-alkanoyloxymethyl;

$X^2$ is —$CH_2$—, —O—, —S—, —NH—, —C(O)—, —OC(O)—, —C(O)O—, —NH—C(O)— or —C(O)—NH—;

$X^3$ is $C_1$-$C_6$-alkylene, —($CH_2$—$CH_2$—O)$_m$—, —($CH_2$—O)$_p$— or a single bond;

$X^4$ is —NH—, —C(O)—NH—, —NH—C(O)—, —NH—CH(NH$_2$)—, —CH(NH$_2$)—NH—, —NH—C(NH)—NH—, —C(O)—NH—CH(NH$_2$)—, —C(O)—NH—C(NH)—NH—, NH—CH(NH$_2$)—C(O)— or —NH—C(NH)—NH—C(O)—;

$X^5$ is —($CH_2$)$_n$— or phenylene-$CH_2$—;

$Z^1$ is —O— or NH—;

n is an integer from 1 to 4;

m is an integer from 1 to 6; and p is an integer from 1 to 6.

E82. The polypeptide of embodiment E81, wherein $X^2$ is —O—.

E83. The polypeptide of embodiment E81 or E82, wherein $X^3$ is —$CH_2$—$CH_2$—O— or a single bond.

E84. The polypeptide of any one of embodiments E81-E83, wherein the structural element —$X^2$-$X^3$— comprises from 1 to 6 atoms in the main chain.

E85. The polypeptide of any one of embodiments E81-E84, wherein $X^4$ is —NH—, —C(O)—NH—, —NH—CH(NH$_2$)—, —NH—C(NH)—NH—, —C(O)—NH—CH(NH$_2$)— or —C(O)—NH—C(NH)—NH—.

E86. The polypeptide of any one of embodiments E81-E84, wherein $X^4$ is —C(O)—NH—.

E87. The polypeptide of any one of embodiments E81-E86, wherein n is 3 or 4.

E88. The polypeptide of any one of embodiments E81-E87, wherein the structural element —$X^2$-$X^3$-$X^4$—($CH_2$)$_n$— comprises from 5 to 12 atoms in the main chain, such as 6, 7, 8, 9, 10 or 11 atoms in the main chain.

E89. The polypeptide of any one of embodiments E81-E88, wherein the compound has S-configuration with regard to the asymmetric carbon atom carrying $Z^1$.

E90. The polypeptide of any one of embodiments E80-E89, wherein the trans-cyclooctenyl group is an axial isomer of the group of the formula:

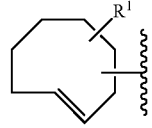

wherein $R^1$ is as defined in any one of embodiments E80-E89.

E91. A method for preparing the polypeptide of any one of embodiments E80-E89, the method comprising:
a) providing a translation system comprising:
 (i) a first aminoacyl tRNA synthetase, or a polynucleotide encoding it; and optionally a second aminoacyl tRNA synthetase, or a polynucleotide encoding it;
 (ii) a first and a second unnatural amino acid or an analogue thereof;
 (iii) a first tRNA having an anticodon to a first selector codon, or a polynucleotide encoding said tRNA; and optionally a second tRNA having an anticodon to a second selector codon, or a polynucleotide encoding said tRNA; and
 (iv) a polynucleotide encoding a target polypeptide and comprising one or more than one first and second selector codon(s),
wherein said first aminoacyl tRNA synthetase (i) is capable of acylating the first tRNA (iii) with the first unnatural amino acid or the analogue thereof (ii) comprising a trans-cyclooctenyl group of the formula:

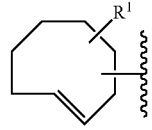

wherein $R^1$ is hydrogen, halogen, $C_1$-$C_4$-alkyl, $(R^aO)_2P(O)O$—$C_1$-$C_4$-alkyl, $(R^bO)_2P(O)$—$C_1$-$C_4$-alkyl, $CF_3$, CN, hydroxyl, $C_1$-$C_4$-alkoxy, —O—$CF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, Di-($C_1$-$C_4$-alkyl)amino, $C_2$-$C_5$-alkenylamino, $C_2$-$C_5$-alkenyl-$C_1$-$C_4$-alkyl-amino or Di-($C_2$-$C_5$-alkenyl)amino; and $R^a$, $R^b$ independently are hydrogen or $C_2$-$C_5$-alkanoyloxymethyl, and said second aminoacyl tRNA synthetase (i) is capable of acylating the second tRNA (iii) with the second unnatural amino acid or the analogue thereof (ii) comprising a cyclooctynyl group of the formula:

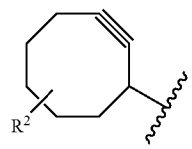

wherein
R² is hydrogen, halogen, C₁-C₄-alkyl, (R^cO)₂P(O)O—C₁-C₄-alkyl, (R^dO)₂P(O)—C₁-C₄-alkyl, CF₃, CN, hydroxyl, C₁-C₄-alkoxy, —O—CF₃, C₂-C₅-alkenoxy, C₂-C₅-alkanoyloxy, C₁-C₄-alkylaminocarbonyloxy or C₁-C₄-alkylthio, C₁-C₄-alkylamino, Di-(C₁-C₄-alkyl)amino, C₂-C₅-alkenylamino, C₂-C₅-alkenyl-C₁-C₄-alkyl-amino or Di-(C₂-C₅-alkenyl)amino; and R^c, R^d independently are hydrogen or C₂-C₅-alkanoyloxymethyl;

b) allowing translation of the polynucleotide (iv) thereby incorporating the first and the second unnatural amino acids or the analogues thereof into the polypeptide at the position(s) encoded by the selector codon(s).

E92. The method of embodiment E91, wherein said translation system is a cell expressing said aminoacyl tRNA synthetase(s).

E93. The method of embodiment E92, wherein said aminoacyl tRNA synthetase is a pyrrolysyl tRNA synthetase.

E94. The method of embodiment E93, wherein said pyrrolysyl tRNA synthetase comprises the amino acid sequence set forth in SEQ ID NO:1 or 2.

E95. The method of any one of embodiments E91-E94, wherein the trans-cyclooctenyl group is an axial isomer of the group of the formula:

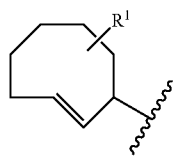

wherein R¹ is as defined in any one of embodiments E91-E94.

E96. An unnatural amino acid comprising a trans-cyclooctenyl group of the formula:

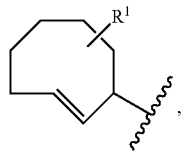

wherein
R¹ is hydrogen, halogen, C₁-C₄-alkyl, (R^aO)₂P(O)O—C₁-C₄-alkyl, (R^bO)₂P(O)—C₁-C₄-alkyl, CF₃, CN, hydroxyl, C₁-C₄-alkoxy, —O—CF₃, C₂-C₅-alkenoxy, C₂-C₅-alkanoyloxy, C₁-C₄-alkylaminocarbonyloxy or C₁-C₄-alkylthio, C₁-C₄-alkylamino, Di-(C₁-C₄-alkyl)amino, C₂-C₅-alkenylamino, C₂-C₅-alkenyl-C₁-C₄-alkyl-amino or Di-(C₂-C₅-alkenyl)amino; and R^a, R^b independently are hydrogen or C₂-C₅-alkanoyloxymethyl, or an analogue of the unnatural amino acid.

E97. The unnatural amino acid of embodiment E96, having the formula:

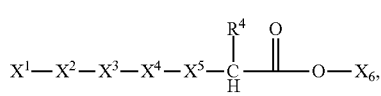

wherein
X¹ is a trans-cyclooctenyl group of the formula:

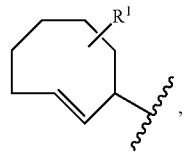

R¹ is hydrogen, halogen, C₁-C₄-alkyl, (R^aO)₂P(O)O—C₁-C₄-alkyl, (R^bO)₂P(O)—C₁-C₄-alkyl, CF₃, CN, hydroxyl, C₁-C₄-alkoxy, —O—CF₃, C₂-C₅-alkenoxy, C₂-C₅-alkanoyloxy, C₁-C₄-alkylaminocarbonyloxy or C₁-C₄-alkylthio, C₁-C₄-alkylamino, Di-(C₁-C₄-alkyl)amino, C₂-C₅-alkenylamino, C₂-C₅-alkenyl-C₁-C₄-alkyl-amino or Di-(C₂-C₅-alkenyl)amino; and R^a, R^b independently are hydrogen or C₂-C₅-alkanoyloxymethyl.

X² is —CH₂—, —O—, —S—, —NH—, —C(O)—, —OC(O)—, —C(O)O—, —NH—C(O)— or —C(O)—NH—;

X³ is C₁-C₆-alkylene, —(CH₂—CH₂—O)_m—, —(CH₂—O)_p—, or a single bond;

X⁴ is —NH—, —C(O)—NH—, —NH—C(O)—, —NH—CH(NH₂)—, —CH(NH₂)—NH—, —NH—C(NH)—NH—, —C(O)—NH—CH(NH₂)—, —C(O)—NH—C(NH)—NH—, NH—CH(NH₂)—C(O)— or —NH—C(NH)—NH—C(O)—;

X⁵ is —(CH₂)_n— or phenylene-CH₂—;

X⁶ is hydrogen, C₁-C₆-alkyl, C₁-C₆-alkoxy-C₁-C₂-alkyl, C₂-C₇-alkanoyloxy-C₁-C₂-alkyl or C₂-C₇-alkanoylsulfanyl-C₁-C₂-alkyl;

R⁴ is —OH or —NH₂;

n is an integer from 0 to 4;

m is an integer from 1 to 6; and p is an integer from 1 to 6, or an acid or base addition salt thereof.

E98. The unnatural amino acid or salt of embodiment E96 or E97, wherein R² is hydrogen.

E99. The unnatural amino acid or salt of any one of embodiments E96-E98, wherein X² is —O—.

E100. The unnatural amino acid or salt of any one of embodiments E96-E99, wherein X³ is —CH₂—CH₂—O— or a single bond.

E101. The unnatural amino acid or salt of any one of embodiments E96-E100, wherein the structural element —X²-X³— comprises from 1 to 6 atoms in the main chain.

E102. The unnatural amino acid or salt of any one of embodiments E96-E101, wherein X⁴ is —NH—, —C(O)—NH—, —NH—CH(NH₂)—, —NH—C(NH)—NH—, —C(O)—NH—CH(NH₂)— or —C(O)—NH—C(NH)—NH—.

E103. The unnatural amino acid or salt of any one of embodiments E96-E102, wherein X⁴ is —C(O)—NH—.

E104. The unnatural amino acid or salt of any one of embodiments E96-E103, wherein X⁵ is —(CH₂)_n— wherein n is defined as in any one of embodiments E96-E103.

E105. The compound or salt of any one of embodiments E96-E104, wherein n is 3 or 4.

E106. The unnatural amino acid or salt of any one of embodiments E96-E105, wherein the structural element —X²-X³-X⁴—(CH₂)ₙ— comprises from 5 to 12 atoms in the main chain, such as 6, 7, 8, 9, 10 or 11 atoms in the main chain.

E107. The unnatural amino acid or salt of any one of embodiments E96-E106, wherein X⁶ is hydrogen, $C_1$-$C_6$-alkoxymethyl, $C_1$-$C_6$-alkoxyeth-1-yl, $C_2$-$C_7$-alkanoyloxymethyl or $C_2$-$C_7$-alkanoylsulfanylethyl.

E108. The unnatural amino acid or salt any one of embodiments E96-E106, wherein X⁶ is hydrogen.

E109. The unnatural amino acid or salt of any one of embodiments E96-E108 having S-configuration with regard to the asymmetric carbon atom carrying R⁴.

E110. The unnatural amino acid or salt of any one of embodiments E96-E109, wherein —X⁵—CHR⁴—C(O)O—X⁶ has the formula:

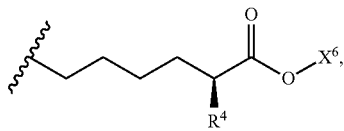

wherein R⁴ and X⁶ are as defined in any one of embodiments E96-E109.

E111. The unnatural amino acid or salt of any one of embodiments E96-E109, wherein —X⁵—CHR⁴—C(O)O—X⁶ has the formula:

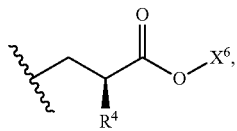

wherein R⁴ and X⁶ are as defined in any one of embodiments E96-E109.

E112. The unnatural amino acid or salt of any one of embodiments E96-E109, wherein —X⁵—CHR⁴—C(O)O—X⁶ has the formula:

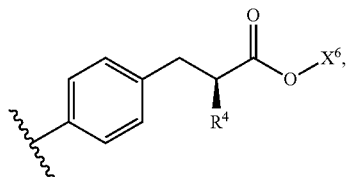

wherein R⁴ and X⁶ are as defined in any one of embodiments E96-E109.

E113. The method of any one of embodiments E96-E112, wherein the trans-cyclooctenyl group is an axial isomer of the group of the formula:

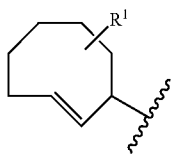

wherein R¹ is as defined in any one of embodiments E96-E112.

E114. The unnatural amino acid or salt of embodiment E96 that is a compound of the formula:

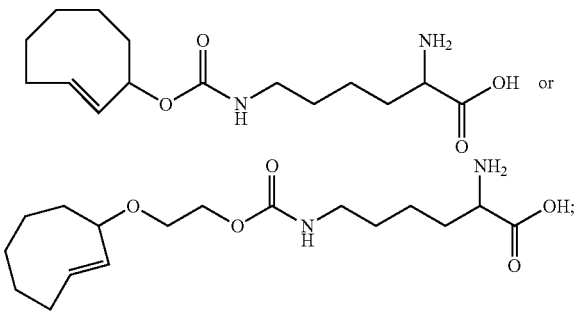

or an acid or base addition salt thereof.

E115. The unnatural amino acid or base addition salt thereof according to embodiment E114 that is an axial isomer with respect to its trans-cyclooctenyl group.

E116. A method for preparing a polypeptide comprising a trans-cyclooctenyl group, the method comprising:
a) providing a translation system comprising:
    (i) an aminoacyl tRNA synthetase, or a polynucleotide encoding it;
    (ii) an unnatural amino acid or salt of any one of embodiments E96-E115;
    (iii) a tRNA having an anticodon to a selector codon, or a polynucleotide encoding said tRNA; and
    (iv) a polynucleotide encoding the target polypeptide and comprising one or more than one selector codon(s),
    wherein the aminoacyl tRNA synthetase (i) is capable of acylating the tRNA (iii) with the compound or salt (ii);
b) allowing translation of the polynucleotide (iv) thereby incorporating the compound (ii) into the target polypeptide at the position(s) encoded by the selector codon(s).

E117. The method of embodiment E116, wherein said translation system is a cell expressing said aminoacyl tRNA synthetase.

E118. The method of embodiment E117, wherein said aminoacyl tRNA synthetase is a pyrrolysyl tRNA synthetase.

E119. The method of embodiment E118, wherein said pyrrolysyl tRNA synthetase comprises the amino acid sequence set forth in SEQ ID NO:1 or 2.

EXAMPLES

Preparation Examples

General Materials and Methods

Unless otherwise noted, materials for chemical synthesis were obtained from commercial suppliers (Acros, Alfa Aesar, Fox-Chemicals, GL Biochem, Sigma-Aldrich) in the highest purity available and used without further purification. Dry solvents were purchased from Sigma-Aldrich and Acros, stored over molecular sieves, and used as supplied. Solvents used for extraction and chromatography were purchased from Acros, Fisher Scientific, and BDH Prolabo (VWR). Tetrazines and azides of fluorophores were purchased from Life Technologies (Darmstadt, Germany), ATTO-TEC (Siegen, Deutschland), or Jena Bioscience (Jena, Germany). Deuterated solvents were obtained from Deutero GmbH (Kastellaun, Germany). Flash chromatography was carried out using Macherey-Nagel silica gel 60 (0.04-0.063 mm, 230-400 mesh) and solvent systems as described as follows. Thin layer chromatography (TLC) was performed on aluminium-backed, precoated silica gel plates (Merck TLC silica gel 60 $F_{254}$) with mixtures (in percent by volume) of $C_6H_{12}$/EtOAc, $CH_2Cl_2$/MeOH(/AcOH), or acetone/MeOH/$H_2O$ as eluents. Spots were detected by a UV hand lamp at $\lambda=254$ nm or $\lambda=366$ nm or staining with either a) anisaldehyde staining solution (85 ml EtOH, 10 ml AcOH, 5 ml concentrated $H_2SO_4$, 0.5 ml anisaldehyde), b) $KMnO_4$ staining solution (3.0 g $KMnO_4$, 20 g $K_2CO_3$ in 300 ml 5% aqueous NaOH), or c) ninhydrin staining solution (250 ml EtOH, 1.5 ml AcOH, 5.0 g ninhydrin) and subsequent heat treatment. Reversed phase (RP) C18 HPLC was performed on a Waters system (Waters 2487 Dual λ Absorbance Detector, Waters 1525 Binary HPLC pump) using a gradient of increasing concentration of solvent B (acetonitrile with 0.1% TFA) starting from 100% solvent A (water with 0.1% TFA). NMR spectra were recorded at 25° C. using a Bruker UltraShield™ Advance 400 (400 MHz, $^1$H; 100 MHz, $^{13}$C) spectrometer. Chemical shifts δ are referenced to residual protonated solvent signals as internal standard (e.g. $CDCl_3$: δ=7.26 ($^1$H), 77.16 ($^{13}$C) ppm)[11]. Assignments of $^1$H and $^{13}$C signals are based on APT and two-dimensional correlation spectroscopy (H,H-COSY) data. Signal multiplicities $^3J(H,H)$ are abbreviated as s (singlet), br (broad singlet), d (doublet), dd (doublet of doublet), dq (doublet of quadruplet), t (triplet), q (quadruplet), dt (doublet of triplet), or m (multiplet). High-resolution (HR) mass spectra were recorded at the University of Heidelberg using electrospray ionization (ESI) mass spectrometry (MS) on a Bruker ApexQe hybrid 9.4 T FT-ICR or using fast atom bombardment (FAB) and electron ionization (EI, electron impact), respectively, on a JEOL JMS-700 magnetic sector mass spectrometer. Products were characterized by NMR ($^1$H, $^{13}$C) and/or MS/HR MS.

Examples 1

N-ε-((1R,8S,9S)-bicyclo[6.1.0]non-4-yn-9-methyloxy)carbonyl)-L-lysine

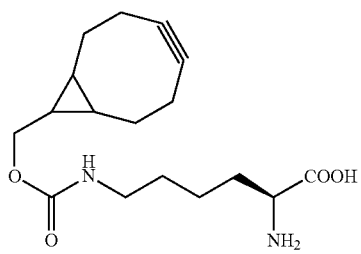

1

Unnatural lysine-based amino acid 1 was purchased from Sirius Fine Chemicals SiChem (Bremen, Germany). Compound 1 was used as a mixture of the endo-and exo-isomer. Compound 1 is also referred to as BCN.

Example 2

N-ε-((trans-Cyclooct-4-en-1-yloxy)carbonyl)-L-lysine

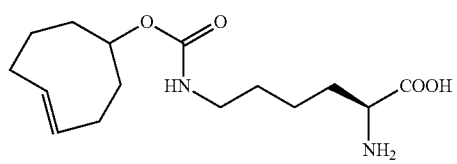

2

Compound 2 was synthesized as described in WO 2012/051885 and T. Plass, S. Milles, C. Koehler, J. Szymanski, R. Mueller, M. Wiessler, C. Schultz, E. A. Lemke, *Angew Chem Int Ed Engl* 2012, 51, 4166-4170. Compound 2 is also referred to as TCO.

Example 3

N-ε-((trans-Cyclooct-2-en-1-yloxy)carbonyl)-L-lysine

Scheme S1 shows the synthesis of trans-cyclooct-2'-ene-functionalized lysine derivative 3 (also termed as TCO*).

Scheme S1:

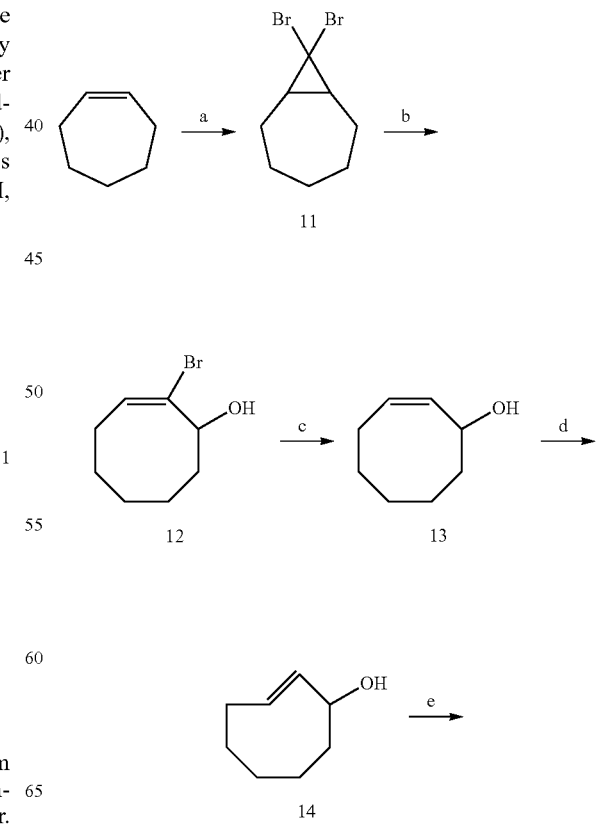

-continued

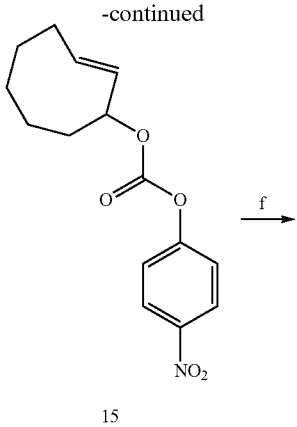

15

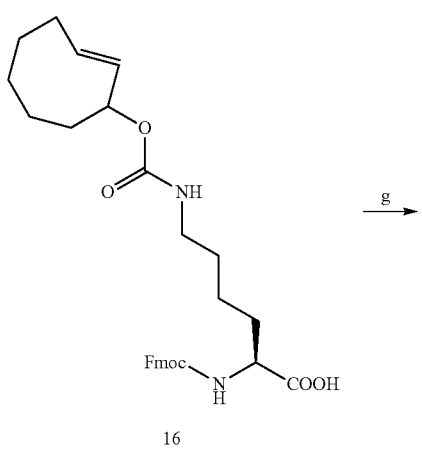

16

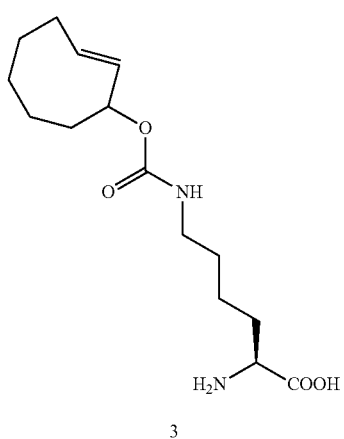 [SMILES: N[C@@H](CCCCNC(=O)OC1/C=C/CCCCC1)C(=O)O]

3

Reagents and conditions: a) KO'Bu, CHBr₃, pentane, 0° C. to rt, o/n; b) AgClO₄, acetone/H₂O, rt, 1 h; c) 'BuLi in pentane, Et₂O, −78° C. to −20° C., 4 h; d) h·v (λ=254 nm), methyl benzoate, C₆H₁₂/EtOAc, rt, 8 h; e) 4-nitrophenyl chloroformate, pyridine, CH₂Cl₂, rt 2 h; f) Fmoc-Lys-OH*HCl, DIEA; DMSO, rt, o/n; g) piperidine, CH₂Cl₂, rt, 30 min.

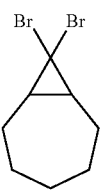

11

Literature-known 8,8-dibromobicyclo[5.1.0]octane 11 was synthesized starting from commercially available cis-cycloheptene as reported earlier (A. B. Neef, C. Schultz, *Angewandte Chemie* 2009, 48, 1498-1500) and used without chromatographic purification.

¹H-NMR (CDCl₃) δ=2.32-2.21 (m, 2H), 1.94-1.78 (m, 3H), 1.77-1.66 (m, 2H), 1.45-1.30 (m, 2H), 1.27-1.10 (m, 3H) ppm.

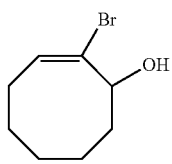

12

2-bromocycloct-2-en-1-ol 12 known from literature was synthesized according to previously described protocols (a) C. B. Reese, A. Shaw, *J Chem Soc Perk T* 1 1975, 2422-2434; b) H. J. J. Loozen, J. W. Dehaan, H. M. Buck, *Journal of Organic Chemistry* 1977, 42, 418-422). Briefly, to a stirred solution of 8,8-dibromobicyclo[5.1.0]octane 11 (1.0 eq.) in acetone (0.5 M) and water (15.0 eq.). AgClO₄ (2.0 eq.) was added in small portions at rt over 30 min and stirred for additional 60 min. 1 M HCl was added until the formation of white precipitate stopped. The mixture was filtered and the residue washed with EtOAc. The filtrate was separated and the aqueous layer extracted with EtOAc (3×). The combined organic fractions were washed with brine, dried over Na₂SO₄, filtered over silica gel, and concentrated. The crude product was purified by flash chromatography (20% EtOAc in C₆H₁₂) to yield 12 as a pale yellow liquid.

$R_f$ (20% EtOAc in C₆H₁₂)=0.4.

¹H-NMR (CDCl₃) δ=6.12 (dd, ³J(H,H)=11.7, 4.2 Hz, 1H), 4.19 (dd, ³J(H,H)=10.4, 5.3 Hz, 1H), 2.68 (dq, ³J(H,H)=11.9, 5.5 Hz, 1H), 2.36-2.29 (m, 1H), 2.23-2.10 (m, 2H), 2.08-2.00 (m, 2H), 1.94-1.67 (m, 4H), 1.56-1.44 (m, 1H), 1.31-1.22 (m, 1H) ppm.

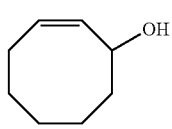

13

To a solution of the 2-bromocycloct-2-en-1-ol 12 (1.0 eq., 10.24 g, 49.7 mmol) in dry Et₂O (0.7 M, 71 ml) at −78° C. 'BuLi (3.2 eq., 159 mmol, 99.4 ml of a 1.6 M solution of 'BuLi in pentane) was added dropwise under Ar over 1 h. After complete addition the mixture was stirred at −78° C. for another 10 min and was then allowed to warm to −20° C. over 3 h. The solution was quenched by addition of sat. aq. NaHCO₃ solution and stirred for 1 h at rt. The layers were separated and the organic layer was extracted with EtOAc (3×). Next, the combined organic fractions were washed with brine, dried over Na$_2$SO$_4$, and concentrated. The crude product was purified by FC (20% EtOAc in C$_6$H$_{12}$) to yield compound 13 (4.37 g, 34.6 mmol, 70% yield) as a colorless liquid.

R$_f$ (20% EtOAc in C$_6$H$_{12}$)=0.4.

$^1$H-NMR (CDCl$_3$) δ=5.71-5.50 (m, 2H), 4.70-4.60 (m, 0.3H), 4.32-4.22 (m, 0.7H), 2.45-2.35 (m, 0.7H), 2.20-2.04 (m, 1.3H), 2.02-1.34 (m, 6H), 1.10-1.03 (m, 0.6H), 0.94-0.84 (m, 0.7H), 0.81-0.70 (m, 0.7H) ppm (two isomers).

$^{13}$C-NMR (CDCl$_3$) δ=135.6, 134.9, 132.0, 128.7, 76.9, 69.5, 44.3, 38.9, 35.4, 29.1, 29.1, 27.7, 26.3, 25.9, 23.7 ppm (two isomers).

HR MS (EI pos.) m/z: calcd for C$_8$H$_{14}$O [M+e$^-$]$^+$: 126.1045, meas.: 126.1040.

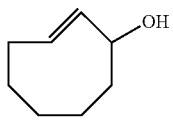

14

Compound 14 was prepared starting from its cis-precursor 13 according to a previously described procedure (a) N. K. Devaraj, R. Upadhyay, J. B. Haun, S. A. Hilderbrand, R. Weissleder, *Angewandte Chemie* 2009, 48, 7013-7016; b) M. Royzen, G. P. Yap, J. M. Fox, *Journal of the American Chemical Society* 2008, 130, 3760-3761). Photoisomerization with active removal of the trans-isomer was carried out in a Rayonet RPR-100 UV reactor (Southern New England Ultraviolet Company, Branford, Conn., USA) for 8 h at rt (temperature inside the reactor was about 30° C.). Briefly, the UV reactor was charged with 13 (1.0 eq., 1.89 g, 14.9 mmol), methyl benzoate (1.5 eq., 3.51 g, 2.80 ml, 22.4 mmol), and solvent (20% C$_6$H$_{12}$ in Et$_2$O, 1000 ml). After work-up, a yellow oil (0.94 g, 7.42 mmol, 50%) was obtained that was used in the next step without further purification. NMR analysis proofed the presence of two isomers in the ratio of 1.0:1.1.

R$_f$ (20% EtOAc in C$_6$H$_{12}$)=0.4.

$^1$H-NMR (CDCl$_3$) δ=6.00-5.91 (m, 0.5H), 5.71-5.62 (m, 0.5H), 5.61-5.51 (m, 1H), 4.62 (br, 0.5H), 4.27 (dt, $^3$J(H,H)=9.5, 5.5 Hz, 0.5H), 2.52-2.45 (m, 0.5H), 2.43-2.36 (m, 0.5H), 2.20-2.12 (m, 0.5H), 2.08-1.92 (m, 2H), 1.90-1.79 (m, 1H), 1.77-1.66 (m, 2H), 1.64-1.37 (m, 2.5H), 1.16-1.06 (m, 0.5H), 0.94-0.84 (m, 0.5), 0.82-0.71 (m, 1H) ppm.

$^{13}$C-NMR (CDCl$_3$) δ=135.5, 135.1, 132.0, 130.5, 76.8, 71.2, 44.3, 43.2, 36.1, 35.8, 35.8, 35.4, 29.2, 29.0, 27.6, 23.1 ppm.

HR MS (EI pos.) m/z: calcd for C$_8$H$_{14}$O [M+e$^-$]$^+$: 126.1045, meas.: 126.1044.

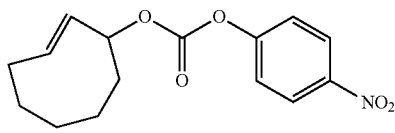

15

To a stirred solution of compound 14 (1.0 eq., 0.94 g, 7.42 mmol) in CH$_2$Cl$_2$ (20 ml) was added pyridine (2.5 eq., 1.50 ml, 18.6 mmol) under Ar. A solution of 4-nitrophenyl chloroformate (1.1 eq., 1.65 g, 8.17 mmol) in CH$_2$Cl$_2$ (20 ml) was added at rt and the resulting reaction mixture stirred for 2 h. A sat. aq. solution of NH$_4$Cl (50 ml) was used to stop the reaction. After phase separation, the aqueous layer was extracted with CH$_2$Cl$_2$ (2×). The combined organic layers were washed with a sat. aq. NaCl solution, dried over Na$_2$SO$_4$, and concentrated. The crude product was purified by FC (5% EtOAc in C$_6$H$_{12}$) to yield compound 15 (1.63 g, 5.59 mmol, 75%) as a pale yellow wax (T$_m$=74.6-76.8° C.).

R$_f$ (10% EtOAc in C$_6$H$_{12}$)=0.4.

$^1$H-NMR (CDCl$_3$) δ=8.31-8.25 (m, 2H), 7.43-7.37 (m, 2H), 6.03-5.94 (m, 0.5H), 5.90-5.80 (m, 0.5H), 5.66 (dd, $^3$J(H,H)=16.2, 9.5 Hz, 0.5H), 5.56 (dd, $^3$J(H,H)=16.5, 2.2 Hz, 0.5H), 5.44 (br, 0.5H), 5.17 (dt, $^3$J(H,H)=10.1, 5.6 Hz, 0.5H), 2.56-2.44 (m, 1H), 2.38-2.30 (m, 0.5H), 2.26-2.18 (m, 0.5H), 2.12-1.85 (m, 3H), 1.82-1.65 (m, 1.5H), 1.61-1.39 (m, 1.5H), 1.23-1.12 (m, 0.5H), 0.98-0.78 (m, 1.5H) ppm.

$^{13}$C-NMR (CDCl$_3$) δ=155.6, 151.9, 151.7, 145.3, 134.8, 133.2, 130.1, 129.3, 125.3, 125.3, 121.8, 83.3, 78.8, 40.5, 40.4, 36.0, 35.9, 35.6, 35.5, 28.9, 28.8, 27.3, 24.0 ppm.

HR MS (FAB pos.) m/z: calcd for C$_{15}$H$_{17}$NO$_5$ [M+e$^-$]$^+$: 291.1107, meas.: 291.1116.

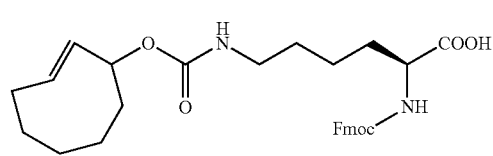

16

Fmoc-Lys-OH*HCl (2.0 eq., 4.45 g, 11.0 mmol) was dissolved in DIEA (3.0 eq., 2.87 ml, 16.5 mmol) and anhydrous DMSO (0.2 M, 27 ml) under Ar. Next, a clear solution of compound 15 (1.0 eq., 1.60 g, 5.49 mmol) in anhydrous DMSO (0.2 M, 27 ml) was added dropwise at rt and under Ar over a period of 2 h. The reaction mixture was stirred o/n at rt. H$_2$O (50 ml) and EtOAc (150 ml) were added and the pH of the aqueous layer was adjusted to 1-3 with conc. HCl. The phases were separated and the aqueous layer was extracted with EtOAc (3×). The combined organic layers were washed with brine (2×) and dried over Na$_2$SO$_4$. All volatile components were evaporated under reduced pressure and the crude product was purified by FC (10% MeOH in CH$_2$Cl$_2$) to yield compound 16 (1.45 g, 2.79 mmol, 51%) as a white foam.

R$_f$ (8% MeOH and 2% AcOH in CH$_2$Cl$_2$)=0.5.

$^1$H-NMR (MeOD) δ=7.79 (d, $^3$J(H,H)=7.5 Hz, 2H), 7.67 (t, $^3$J(H,H)=7.2 Hz, 2H), 7.39 (t, $^3$J(H,H)=7.5 Hz, 2H), 7.31 (t, $^3$J(H,H)=7.3 Hz, 2H), 5.88-5.64 (m, 1H), 5.58-5.43 (m, 1H), 5.22 (br, 0.5H), (4.98 (dt, $^3$J(H,H)=9.9, 5.2 Hz, 0.5H), 4.37-4.32 (m, 2H), 4.22 (t, $^3$J(H,H)=6.7 Hz, 1H), 4.13-4.04 (m, 1H), 3.09 (q, $^3$J(H,H)=5.4 Hz, 2H), 2.45-2.34 (m, 1H), 2.16-2.08 (m, 0.5H), 2.05-1.34 (m, 10.5H), 1.19-1.07(m, 0.5H), 0.92-0.75 (m, 1.5H) ppm.

$^{13}$C-NMR (MeOD) δ=157.2, 144.0, 143.8, 143.8, 141.2, 132.4, 131.8, 131.5, 131.2, 127.4, 126.8, 124.9, 119.5, 78.5, 73.7, 66.5, 54.7, 47.1, 40.8, 40.3, 40.1, 40.0, 35.6, 35.4, 35.2, 34.9, 31.3, 29.1, 28.7, 28.6, 27.0, 23.8, 27.8, 27.7 ppm.

HR MS (ESI neg.) m/z: calcd for C$_{30}$H$_{35}$N$_2$O$_6$ [M-H]$^-$: 519.25006, meas.: 519.25127.

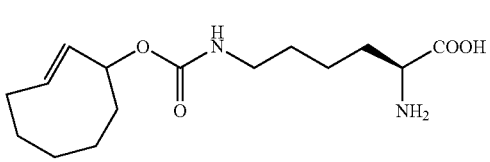

Compound 16 (1.0 eq., 1.43 g, 2.75 mmol) was dissolved in 20% piperidine in CH$_2$Cl$_2$ (40 ml v/v) and stirred for 30 min at rt. After addition of H$_2$O (50 ml), all volatile components were removed under reduced pressure and high vacuum. The crude product was purified via FC (acetone:MeOH:H$_2$O 85:10:5 v/v/v to wash off all impurities followed by 65:25:10 v/v/v to elute the product) on silica gel to yield compound 3 (0.81 g, 2.70 mmol, 98%) as a white powder. Purified 2 decomposed under heating (starting at 180° C.). Compound 3 is also referred to as TCO* in this publication. Compound 3 was a mix of axial isomers of TCO* (herein referred to as compound 3a or TCO*$^a$) and equatorial isomers of TCO* (herein referred to as compound 3b or TCO*$^e$).

R$_f$ (acetone:MeOH:H$_2$O 65:25:10 v/v/v)=0.6.

$^1$H-NMR (DMSO-d$_6$) δ=5.77-5.64 (m, 1H), 5.58-5.44 (m, 1H), 5.15 (br, 0.5H), 4.95 (dt, $^3$J(H,H)=9.5, 5.5 Hz, 0.5H), 3.51 (t, $^3$J(H,H)=5.7 Hz, 1H), 2.94 (q, $^3$J(H,H)=5.4 Hz, 2H), 2.41-2.29 (m, 1H), 2.13-2.04 (m, 0.5H), 1.97-1.84 (m, 2.5H), 1.79-1.24 (m, 8H), 1.05-0.94 (m, 0.5H), 0.88-0.71 (m, 1.5H) ppm.

$^{13}$C-NMR (DMSO-d$_6$) δ=171.6, 155.9, 132.9, 132.7, 131.1, 77.9, 73.0, 53.3, 43.9, 41.4, 40.5, 36.1, 35.7, 35.3, 30.6, 29.5, 28.9, 27.3, 24.2, 22.6, 22.4, 22.2 ppm.

HR MS (ESI neg.) m/z: calcd for C$_{15}$H$_{25}$N$_2$O$_4$ [M-H]$^-$: 297.18198, meas.: 297.18285.

Example 3a

Preparation of Axial and of Equatorial N-ε-((trans-Cyclooct-2-en-1-yloxy)carbonyl)-L-lysine After UV irradiation (cf. step d in scheme S1 above) the axial and the equatorial isomers of compound 14 (trans-cyclooct-2-en-1-ol) were separated by flash chromatography on silica (eluent: EtOAc/cyclohexane at a ratio of 1:4; Rf TCO*$^a$=0.38, Rf TCO*$^e$=0.27), and then separately coupled to lysine (as described for compound 14 in Example 3 above) so as to provide the axial isomer 3a and the equatorial isomer 3b of compound 3.

Example 4

N-ε-((trans-Cyclooct-3-en-1-yloxy)carbonyl)-L-lysine

Scheme S2 shows the synthesis of trans-cyclooct-2'-ene-functionalized lysine derivative 4 (also termed as TCO$^#$).

Scheme S2:

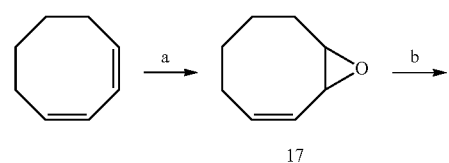

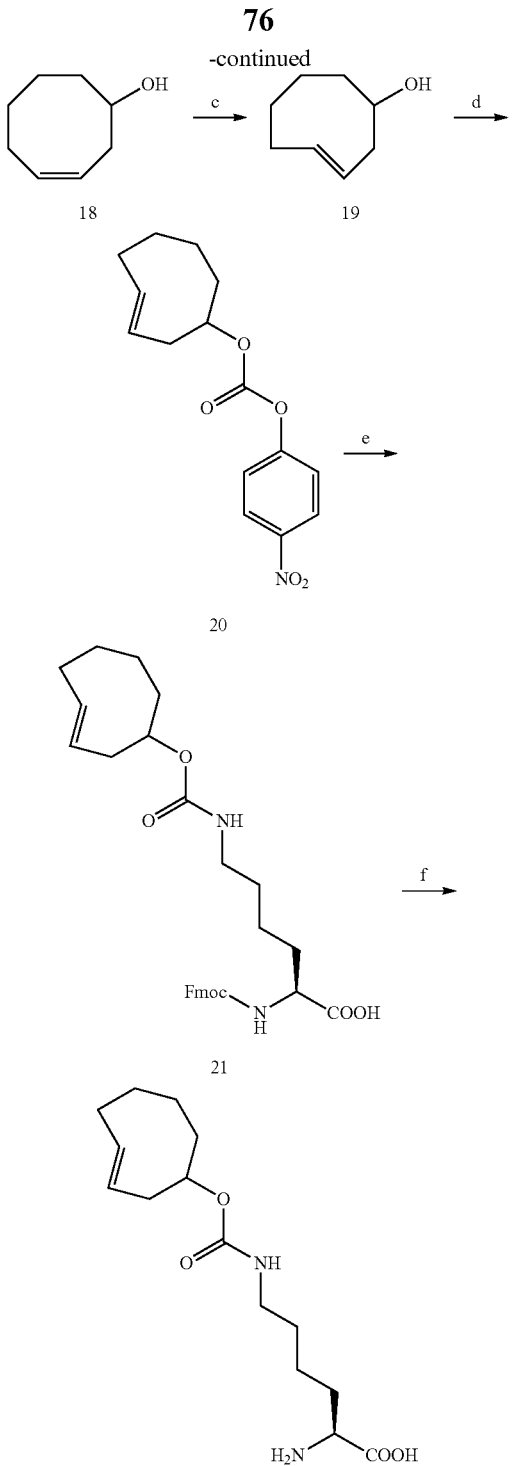

Reagents and conditions: a) 3-chloroperbenzoic acid, CHCl$_3$, rt, o/n; b) LiAlH$_4$, THF, 0° C. to rt, o/n; c) h·v (λ=254 nm), methyl benzoate, C$_6$H$_{12}$/EtOAc, rt, 10 h; d) 4-nitrophenyl chloroformate, pyridine, CH$_2$Cl$_2$, rt 2 h; e) Fmoc-Lys-OH*HCl, DIEA; DMSO, rt, o/n; f) piperidine, CH$_2$Cl$_2$, rt, 30 min.

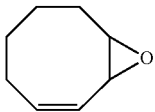

17

Literature-known compound 17 was synthesized starting from commercially available 1,3-cyclooctadiene according to a previously described protocol (K. Zhang, M. A. Lackey, J. Cui, G. N. Tew, *Journal of the American Chemical Society* 2011, 133, 4140-4148). Briefly, a solution of 3-chloroperbenzoic acid (70-77%, 0.8 eq., 86.75 g, 327 mmol) in CHCl$_3$ (1100 ml) was added dropwise over 2 h to 1,3-cyclooctadiene (1.0 eq., 50.63 g, 468 mmol) with stirring. The reaction mixture was stirred at rt for 15 h. After filtration to remove 3-chlorobenzoic acid, the filtrate was successively washed with solutions of sodium bisulfite (10% in H$_2$O), NaHCO$_3$ (10% in H$_2$O), and brine. Next, the organic layer was dried over Na$_2$SO$_4$ and concentrated. FC (5% EtOAc in C$_6$H$_{12}$) yielded 17 (48.28 g, 389 mmol, 83%) as a clear liquid.

R$_f$ (10% EtOAc in C$_6$H$_{12}$)=0.3. $^1$H-NMR (CDCl$_3$) δ=5.81-5.74 (m, 1H), 5.62-5.56 (m, 1H), 3.48-3.44 (m, 1H), 3.15-3.09 (m, 1H), 2.37-2.26 (m, 1H), 2.14-1.97 (m, 2H), 1.83-1.60 (m, 3H), 1.53-1.37 (m, 2H) ppm.

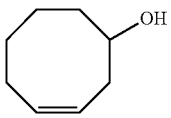

18

A solution of LiAlH$_4$ (0.5 eq., 81.5 ml of a 1.0 M solution in THF, 81.5 mmol) was added dropwise at 0° C. and under Ar to a stirred solution of 17 (1.0 eq., 20.23 g, 163 mmol) in THF (1.0 M, 163 ml). The reaction mixture was allowed to warm up to rt and stirred o/n. H$_2$O (about 20 ml) was carefully added to stop the reaction. The reaction mixture was filtered, dried over Na$_2$SO$_4$, and concentrated. FC (20% EtOAc in C$_6$H$_{12}$) yielded 18 (15.81 g, 125 mmol, 77%) as a clear liquid.

R$_f$ (20% EtOAc in C$_6$H$_{12}$)=0.4.
$^1$H-NMR (CDCl$_3$) δ=5.76-5.60 (m, 2H), 3.84-3.77 (m, 1H), 2.36 (dd, $^3$J(H,H)=7.5, 6.3 Hz, 2H), 2.28-2.18 (m, 1H), 2.14-2.05 (m, 1H), 1.87-1.78 (m, 1H), 1.73-1.63 (m, 1H), 1.61-1.43 (m, 4H), 1.40-1.30 (m, 1 H) ppm.
$^{13}$C-NMR (CDCl$_3$) δ=132.4, 125.0, 72.2, 35.1, 34.0, 28.3, 25.7, 21.2 ppm.

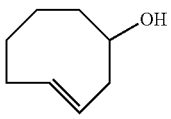

19

Compound 19 was prepared starting from its cis-precursor 18 according to a previously described procedure (a) N. K. Devaraj, R. Upadhyay, J. B. Haun, S. A. Hilderbrand, R. Weissleder, *Angewandte Chemie* 2009, 48, 7013-7016; b) M. Royzen, G. P. Yap, J. M. Fox, *Journal of the American Chemical Society* 2008, 130, 3760-3761). Photoisomerization with active removal of the trans-isomer was carried out in a Rayonet RPR-100 UV reactor (Southern New England Ultraviolet Company, Branford, Conn., USA) for 10 h at rt (temperature inside the reactor was around 30° C.). Briefly, the UV reactor was charged with 19 (1.0 eq., 6.17 g, 48.9 mmol), methyl benzoate (1.5 eq., 9.20 ml, 73.3 mmol), and solvent (30% C$_6$H$_{12}$ in Et$_2$O, 1000 ml). After work-up and FC (20% EtOAc in C$_6$H$_{12}$) a clear oil (4.25 g, 33.7 mmol, 69%) was obtained. NMR analysis showed the presence of two isomers in the ratio of 1.0:1.2.

R$_f$ (20% EtOAc in C$_6$H$_{12}$)=0.4.
$^1$H-NMR (CDCl$_3$) δ=5.85-5.76 (m, 0.45H), 5.61-5.44 (m, 1H), 5.32-5.23 (m, 0.55H), 4.44-4.38 (m, 0.45H), 3.74-3.65 (m, 0.55H), 2.87-2.79 (m, 0.55H), 2.48-2.34 (m, 1.45H), 2.21-2.12 (m, 0.45H), 2.10-1.78 (m, 3.56H), 1.56-1.29 (m, 2.9H), 1.24-1.06 (m, 1.55H), 0.81-0.71 (m, 0.55H) ppm.

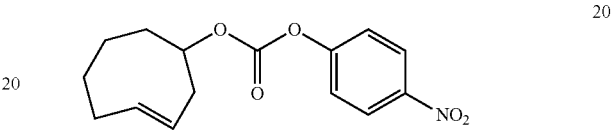

20

To a stirred solution of compound 19 (1.0 eq., 4.25 g, 33.7 mmol) in CH$_2$Cl$_2$ (44 ml) pyridine (2.5 eq., 6.81 ml, 84.2 mmol) was added under Ar. A solution of 4-nitrophenyl chloroformate (1.1 eq., 7.47 g, 37.1 mmol) in CH$_2$Cl$_2$ (30 ml) was added at rt and the resulting reaction mixture stirred for 2 h. A sat. aq. solution of NH$_4$Cl was used to stop the reaction. After phase separation, the aqueous layer was extracted with CH$_2$Cl$_2$ (2×). The combined organic layers were washed with brine, dried over Na$_2$SO$_4$, and concentrated. The crude product was purified by FC (5% EtOAc in C$_6$H$_{12}$) to yield compound 20 (8.51 g, 29.2 mol, 87%) as a pale yellow wax (T$_m$=75.3-78.7° C.).

R$_f$ (5% EtOAc in C$_6$H$_{12}$)=0.2.
$^1$H-NMR (CDCl$_3$) δ=8.31-8.25 (m, 2H), 7.42-7.35 (m, 2H), 5.80-5.55 (m, 1.5H), 5.35-5.30 (m, 0.5H), 5.28-5.19 (m, 0.5H), 4.72-4.63 (m, 0.5H), 3.04-2.96 (m, 0.5H), 2.74-2.65 (m, 0.5H), 2.53-2.19 (m, 2.5H), 2.11-1.83 (m, 3H), 1.61-1.47 (m, 1H), 1.42-1.12 (m, 2H), 0.89-0.77 (m, 0.5H) ppm.
$^{13}$C-NMR (CDCl$_3$) δ=155.7, 155.6, 152.0, 151.8, 145.3, 138.5, 137.0, 128.1, 125.3, 125.1, 121.8, 121.8, 85.9, 83.5, 40.5, 39.8, 36.0, 35.6, 35.6, 35.5, 32.7, 30.6, 23.5, 20.4 ppm.
HR MS (FAB pos.) m/z: calcd for C$_{15}$H$_{18}$NO$_5$ [M+H]$^+$: 291.1185, meas.: 292.1189.

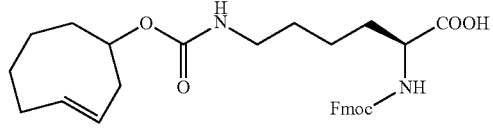

21

Fmoc-Lys-OH*HCl (1.5 eq., 5.43 g, 20.0 mmol) was dissolved in DIEA (3.0 eq., 6.97 ml, 40.0 mmol) and anhydrous DMSO (0.2 M, 67 ml) under Ar. Next, a clear solution of compound 20 (1.0 eq., 3.88 g, 13.3 mmol) in anhydrous DMSO (0.5 M, 27 ml) was added dropwise at rt and under Ar over a period of 2 h. The reaction mixture was stirred o/n at rt. H$_2$O (80 ml) and EtOAc (170 ml) were added. The pH of the aqueous layer was adjusted to 1-3 with conc. HCl. The phases were separated and the aqueous layer was extracted with EtOAc (3×). The combined organic layers were washed with brine (2×) and dried over Na$_2$SO$_4$.

All volatile components were evaporated under reduced pressure and the crude product was purified by FC (10% MeOH in CH$_2$Cl$_2$) to yield compound 21 (4.79 g, 9.20 mmol, 71%) as a white foam.

R$_f$ (8% MeOH and 2% AcOH in CH$_2$Cl$_2$)=0.5.

$^1$H-NMR (CDCl$_3$) δ=7.76 (d, $^3$J(H,H)=7.4 Hz, 2H), 7.64-7.55 (m, 2H), 7.40 (t, $^3$J(H,H)=7.3 Hz, 2H), 7.31 (t, $^3$J(H,H)=7.3 Hz, 2H), 5.73-5.44 (m, 2.5H), 5.27-5.18 (m, 0.5H), 4.52-4.33 (m, 3H), 4.27-4.18 (m, 1H), 3.24-3.12 (m, 2H), 2.60-0.73 (m, 14H) ppm.

HR MS (ESI neg.) m/z: calcd for C$_{30}$H$_{35}$N$_2$O$_6$ [M−H]$^-$: 519.25006, meas.: 519.25114; calcd for C$_{30}$H$_{35}$N$_2$O$_7$ [M−OH]$^-$: 535.24498, meas.: 535.24600.

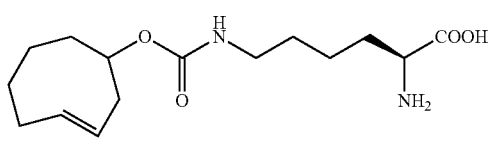

4

Compound 21 (1.0 eq., 4.16 g, 7.98 mmol) was dissolved in 20% piperidine in CH$_2$Cl$_2$ (25 ml) and stirred for 30 min at rt. After addition of H$_2$O (30 ml), all volatile components were removed under reduced pressure and high vacuum. The crude product was purified via FC (ace-tone:MeOH:H$_2$O 85:10:5 v/v/v to wash off all impurities followed by 65:25:10 v/v/v to elute the product) on silica gel to yield compound 4 (2.02 g, 6.78 mmol, 85%) as a white powder. Purified 3 decomposed under heating (starting at 180° C.). Compound 4 is also referred to as TCO$^{\#}$ in this publication.

R$_f$ (acetone:MeOH:H$_2$O 65:25:10 v/v/v)=0.6.

$^1$H-NMR (MeOD) δ=5.76-5.47 (m, 1.5H), 5.31-5.21 (m, 0.5H), 5.13 (br, 0.5H), 4.57-4.49 (m, 0.5H), 3.54-3.47 (m, 1H), 3.15-3.06 (m, 4H), 2.82-2.73 (m, 0.5H), 2.48-2.34 (m, 1.5H), 2.23-2.12 (m, 1H), 2.06-1.75 (m, 4.5H), 1.74-1.67 (m, 0.5H), 1.57-1.37 (m, 4H), 1.27-1.06 (m, 1.5H), 0.89-0.78 (m, 0.5H) ppm.

$^{13}$C-NMR (MeOD) δ=150.7, 149.2, 137.4, 135.7, 132.3, 54.7, 45.5, 44.4, 40.8, 39.8, 39.7, 37.6, 35.0, 32.7, 30.5, 29.2, 24.0, 23.3, 22.5, 22.1 ppm.

HR MS (ESI neg.) m/z: calcd for C$_{15}$H$_{25}$N$_2$O$_4$ [M−H]$^-$: 297.18198, meas.: 297.18287.

Examples 5

N-ε-((Cyclooct-2-yn-1-yloxy)carbonyl)-L-lysine

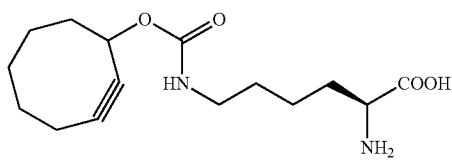

5

Unnatural lysine-based amino acid 5 was purchased from Sirius Fine Chemicals SiChem (Bremen, Germany). Compound 5 can also be synthesized as described in WO 2012/051885. Compound 5 is also referred to as SCO.

Examples 6

Propargyl-lysine

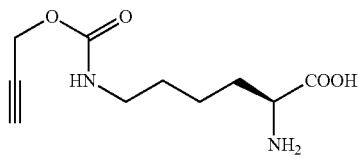

6

Unnatural lysine-based amino acid 6 was purchased from Sirius Fine Chemicals SiChem (Bremen, Germany). Compound 6 is also referred to as PrK.

MS (ESI) m/z: calculated for C$_{15}$H$_{27}$N$_2$O$_4$ [M+H]$^+$: 299.19653, measured: 299.19656.

Biological examples

Example A

Recombinant Protein Expression in *E. coli*

The previously reported plasmids pEvolv tRNA$^{Pyl}$/PylRS$^{AF}$ and pBAD GFP$^{Y39TAG}$ were used to express GFP$^{TAG\to UAA}$, genetically encoding the respective unnatural amino acid (UAA) (a) T. Plass, S. Milles, C. Koehler, C. Schultz, E. A. Lemke, *Angew Chem Int Ed Engl* 2011, 50, 3878-3881; b) T. Plass, S. Milles, C. Koehler, J. Szymanski, R. Mueller, M. Wiessler, C. Schultz, E. A. Lemke, *Angew Chem Int Ed Engl* 2012, 51, 4166-4170). Briefly, plasmids were co-transformed into *E. coli* Top10 (Invitrogen) and grown at 37° C. in the presence of ampicillin and chloramphenicol. For small scale expression, 0.5 ml of an overnight culture was used to inoculate 50 ml Terrific Broth (TB) medium in a shake flask. Cultures grew within 2 h to an OD of 0.2-0.3 at which point a compound selected from compounds 1-5 (FIG. 1a) and compounds 3a and 3b (stock solutions 80 mM in 0.1 M NaOH), or an equal amount of 0.1 M NaOH (for control experiments) were added to a final concentration of 1 mM. The cultures were allowed to grow until OD 0.4-0.6, when expression was induced with 0.02% arabinose. Cultures were harvested by centrifugation after 6-8 h of shaking at 37° C. Pellets were resuspended in a 4× phosphate buffered saline (4×PBS, pH 8.0) solution and cells were lysed by sonication. The supernatant was incubated with ~50 μl of Ni-NTA (Qiagen, Düsseldorf, Germany). Ni-beads were washed with 20 mM imidazole in 4× PBS, pH 8 and then eluted with buffer containing 1 M imidazole.

Compound 3 as well as its pure axial and equatorial isomers 3a and 3b showed very similar incorporation rates, were more readily incorporated than compound 2 by about a factor of two (FIG. 12) and gave improved protein yields (0.4 mg/L).

Example B

In Vitro Cross-Reactivity and Orthogonality of SPAAC and SPIEDAC Reactions

GFP$^{TAG\to UAA}$ was expressed in *E. coli* as described above in presence of 1, 3, and 5. Subsequently, purified protein (Ni-NTA, see above) was labeled with either Cy3-azide (45 μM, 6 h, 37° C.), Me-Tet-Cy3 or H-Tet-Atto532 (both 15

μM, 20 min, 37° C.). All three dyes were obtained from Jena Bioscience. After labeling, samples were directly loaded on a SDS-PAGE gel and analyzed for fluorescence on a commercially available gel documentation system (Alpha Innotech, CA) with UV excitation and ethidium-bromide detection filter settings. Afterwards, the gel was stained with Coomassie (FIG. 1d). No other proteins than GFP$^{TAG \rightarrow UAA}$ were labeled demonstrating the bioorthogonality of the labeling reactions.

Example C

Constructs for Expression of Insulin Receptor (IR) in Mammalian Cells

The IR$^{TAG}$ amber mutant was generated through PCR-based site-directed mutagenesis of a pEGFPN1_IR plasmid, creating a TAG mutation at K676 in the IR gene. This position was picked based on the available IR structure (PDB: 2DTG) (N. M. McKern, M. C. Lawrence, V. A. Streltsov, M. Z. Lou, T. E. Adams, G. O. Lovrecz, T. C. Elleman, K. M. Richards, J. D. Bentley, P. A. Pilling, P. A. Hoyne, K. A. Cartledge, T. M. Pham, J. L. Lewis, S. E. Sankovich, V. Stoichevska, E. Da Silva, C. P. Robinson, M. J. Frenkel, L. G. Sparrow, R. T. Fernley, V. C. Epa, C. W. Ward, *Nature* 2006, 443, 218-221) The resulting pEGFPN1_IR$^{TAG}$ was used in FIG. 2 and FIGS. 9 and 10. Fluorescent signal from C-terminally fused GFP was only present after successful amber suppression and was thus used as readout of successful IR$^{TAG}$ expression. To avoid any contamination from the GFP in SRM experiments (FIG. 3) a bicistronic pCl-IR$^{TAG}$-IRES-CFP construct was generated by inserting the IR$^{K676TAG}$-IRES-CFP cassette into an empty pCl mammalian expression vector (Promega, Madison, USA). At the C-terminus of IR$^{TAG}$ we introduced a Flag-tag which was followed by a TGA stop codon before the IRES sequence. For the expression of PylRS$^{AF}$/tRNA$^{Pyl}$ in mammalian cells we used previously described pCMV tRNA$^{Pyl}$/PylRS$^{AF}$ plasmid (a) T. Plass, S. Milles, C. Koehler, C. Schultz, E. A. Lemke, *Angew Chem Int Ed Engl* 2011, 50, 3878-3881; b) T. Plass, S. Milles, C. Koehler, J. Szymanski, R. Mueller, M. Wiessler, C. Schultz, E. A. Lemke, *Angew Chem Int Ed Engl* 2012, 51, 4166-4170).

Example D

Cell Culture and Transfections with IR Constructs

For insulin receptor experiments, HEK293T cells were maintained in Dulbecco's Modified Eagle's Medium—DMEM (high glucose—4.5 g/l) supplemented with 10% FBS (Sigma), 1% L-glutamine (Invitrogen, Palo Alto, USA) and 1% Pen-Strep (Invitrogen) in a 5% CO$_2$ atmosphere at 37° C. Cells were passaged every 2-3 days up to 15-20 passages. For microscopy, cells were seeded on 4-well chambered Lab-Tek #1.0 borosilicate coverglass (Thermo-Fisher, Ma USA) 15-24 h prior to transfections. Transfections were performed with JetPrime reagent (PegLab, Erlangen, Germany) according to the manufacturer's recommendations. In short, for double-transfections with IR and tRNA$^{Pyl}$/PylRS$^{AF}$ vectors we used plasmids in 1:1 ratio keeping total amount of DNA at 1 μg. UAAs were added after the transfections in two pulses (see FIG. 2a). UAAs were dissolved in DMSO (250 mM stock of PrK; 100 mM stock of TCO*) or 20% formic-acid DMSO (500 mM stock of BCN; 250 mM stock of SCO). Each UAA was used at a final concentration of 250 μM. After the 2$^{nd}$ UAA pulse, cells were rinsed with fresh medium and kept overnight in DMEM.

Example E

Pulse-Chase Labeling of IR

In the morning following transfections, medium was exchanged to serum-free high glucose DMEM supplemented with 10% FBS and Pen-Strep, in which all the subsequent washing and labeling steps were also performed. The transfected cells were then labeled according to the following protocols. In case of SPIEDAC-SPAAC combination, cells were incubated with 10 μM solution of sulfo-Cy5-azide (Lumiprobe, Hannover, Germany) dissolved in serum-free DMEM for 10 min at 37° C., washed with fresh medium, incubated with 5 μM solution of sulfonated-Cy3-Me-Tet (6-Methyl-Tetrazine-Sulfo-Cy3, Jena Bioscience, Jena, Germany) for 10 min at 37° C. and then washed with fresh medium and kept at 37° C. before fixation. For further details regarding SPAAC labeling, please see Example M.

In case of SPIEDAC with seSPIEDAC combination, cells were first incubated with the 5 μM solution of sulfonated Me-Tet-Cy5 (6-Methyl-Tetrazine-Sulfo-Cy5, Jena Bioscience) dissolved in serum-free DMEM for 10 min at 37° C. After the Me-Tet-Cy5 labeling, cells were rinsed with fresh medium. To quench any unreacted TCO* (see FIG. 10 for more details on choice of quencher) cells were subsequently incubated with the non-fluorescent Me-Tet-NH$_2$ (50 μM, dissolved in serum-free DMEM). Me-Tet-N H$_2$ ((4-(6-Methyl-1,2,4,5-tetrazin-3-yl)phenyl)-methanamine) hydrochloride was synthesized according to a published procedure (M. R. Karver, R. Weissleder, S. A. Hilderbrand, *Angew Chem Int Ed Engl* 2011). After this step, cells were rinsed twice with serum-free DMEM and then labeled with H-Tet-Atto532 (Jena Bioscience) by incubating cells in 5 μM solution for around 10 min. Stock solutions of Me-Tet-Cy5 and H-Tet-Atto532 were prepared in DMSO at a concentration of 500 μM. After the labeling, cells were rinsed again, medium was exchanged and cells were kept in the incubator for 1-5 h prior to the fixation step. Fixation was performed with 2% para-formaldehyde (PFA) in PBS at room temperature for 10 min, prior to which, cells were rinsed with PBS.

Example F

Microscopy of IR

After fixation, cells were taken to the microscope, either on the same day or maximum 1-2 days later. This was especially important for the SRM imaging. All confocal imaging was performed on a commercial LEICA TCS SP8 microscope equipped with HCX PL APO 100x/1.40 OIL objective (Mannheim, Germany). For images comparing different levels of labeling, same acquisition settings were used for all the experiments. Cells were imaged in PBS and single plane images were acquired with a pixel size of 114 nm. All SRM was performed on a commercial Leica GSD microscope, equipped with Leica HCX PL APO 100x/NA 1.47 Oil CORR TIRF PIFOC objective and Cy3 and Cy5 filter sets. For SRM, we used an imaging buffer containing oxygen scavenging system (glucose oxidase with catalase—GLOX) in presence of thiols (10 mM 2-aminoethanethiol, MEA) made according to a published protocol (G. T. Dempsey, J. C. Vaughan, K. H. Chen, M. Bates, X. Zhuang, *Nature methods* 2011, 8, 1027-1036). The buffer was prepared fresh and exchanged after 1-3 h of imaging or earlier in case of insufficient blinking events. All the images were acquired in epifluorescent mode, first in the Cy5 and then in Atto532 channel. For the Cy5 channel, a 642 nm Laser and for the Atto532 channel a 532 nm Laser respectively were used for pumping and imaging the blinking with exposure times of 10 ms. To facilitate the return of fluorophores to the ground state, a 405 nm laser was used at very low intensities.

Example G

Constructs for VLP Expression in Mammalian Cells

M1 (A/Hong Kong/68) and HA (A/Aichi/2/68) in the eukaryotic expression vector pCAGGS was obtained from Mikhail Matrosovich (Marburg). The HA sequence was cloned into the pCl expression vector and based on the available structure of HA (PDB: 1 E08) (X. Morelli, M. Czjzek, C. E. Hatchikian, O. Bornet, J. C. Fontecilla-Camps, N. P. Palma, J. J. Moura, F. Guerlesquin, *The Journal of biological chemistry* 2000, 275, 23204-23210) and information about sequence conservation between different flu variants, different amino acid positions were selected and substituted by the amber TAG codon with standard site-directed mutagenesis. In this study the amino acid substitution HA342 was used as it showed good UAA incorporation and labeling efficiency.

Example H

Cell Culture and Sample Preparation for VLPs

HEK293T were maintained in DMEM (low glucose, pyruvate, no glutamine, no phenol red, 11880-028 GIBCO/ Invitrogen) supplemented with 10% fetal calf serum (FCS) and L-glutamine at 37° C. under 5% $CO_2$.

For fluorescence and SRM, cells were seeded on thoroughly cleaned high precision cover slips (Ø=18 mm, thickness=0.17±0.005 mm, CarlRoth) in 6-well tissue culture dishes. Cells were grown to 70-80% confluence before being transfected with the appropriate plasmids at 1:1 ratios with jetPrime (PEQLAB) or 239Expresso (Excellgen) transfection reagent according to the manufacturer's instructions. At 1 h post-transfection 250 µM SCO, PrK or TCO* was added to the growth medium. If production of filamentous virus particles was induced by co-transfection of HA and M1, exogenous bacterial neuraminidase was added—during both UAA pulses—in addition to the UAA at a concentration of 100 mU/ml (*Clostridium perfrigens*; Sigma-Aldrich, Frankfurt, Germany) in order to avoid immediate attachment of generated filaments to the producer cells via binding of HA to sialic acid. After 10 h the UAA containing medium was exchanged to growth medium with the second UAA and incubated for 18 h. After this chase the cells were incubated for 1 h in normal growth medium before labeling the incorporated UAA with tetrazine modified dyes at 37° C. for 20-30 min. First, TCO* was labeled with Me-Tet-Cy5 (Jena Bioscience, 5 µM final concentration), the non-reacted TCO* was then quenched with 50 µM Me-Tet-NH$_2$ for 5 min and SCO was labeled with H-Tet-Atto532 (Jena Bioscience, 5 µM final concentration). Before mounting the cover slides on depression slides (1.2-1.5 mm, Menzel-Glaeser/Thermo-Scientific) the cells were once washed with normal growth medium for 30 min and subsequently fixed with 2% PFA in PBS for 10 min. For SRM, same acquisition settings as described above for IR were used. For confocal microscopy, the sample was mounted with Pro-Long Gold (Invitrogen) on a standard objective slide and cured for 24 h at room temperature before it was imaged with a Leica TCS SP8 microscope.

Example I

Image Analysis

Figure 2:
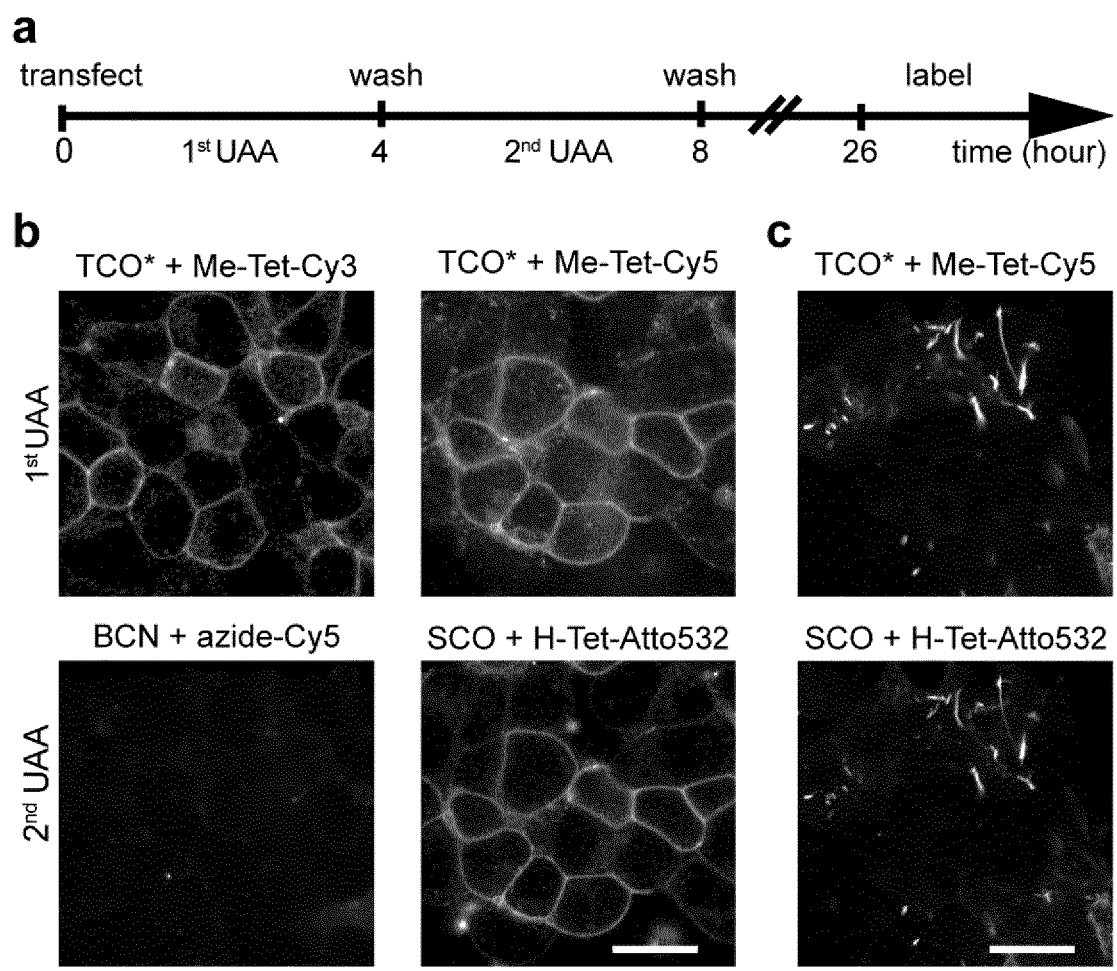
FIG. 2 shows: a) Outline of the expression and labeling scheme employed for dual-color labeling of the Insulin receptor containing an amber mutation (IR$^{TAG}$); b) Confocal images of dual-color labeling of IR with different combinations of UAAs and dyes. The left panels show a combination of SPIEDAC (TCO*+Me-Tet-Cy3 and SPAAC labeling (BCN+azide-Cy5). The right panels show a combination of SPIEDAC (TCO*+Me-Tet-Cy5) and seSPIEDAC between SCO and H-Tet-Atto532; c) Virus like particle (VLP) dual-color labeling showing SPIEDAC between TCO* and Me-Tet-Cy5 (top) and seSPIEDAC between SCO and H-Tet-Atto532 (bottom). Scale bars are 20 µm.
Figure 3:
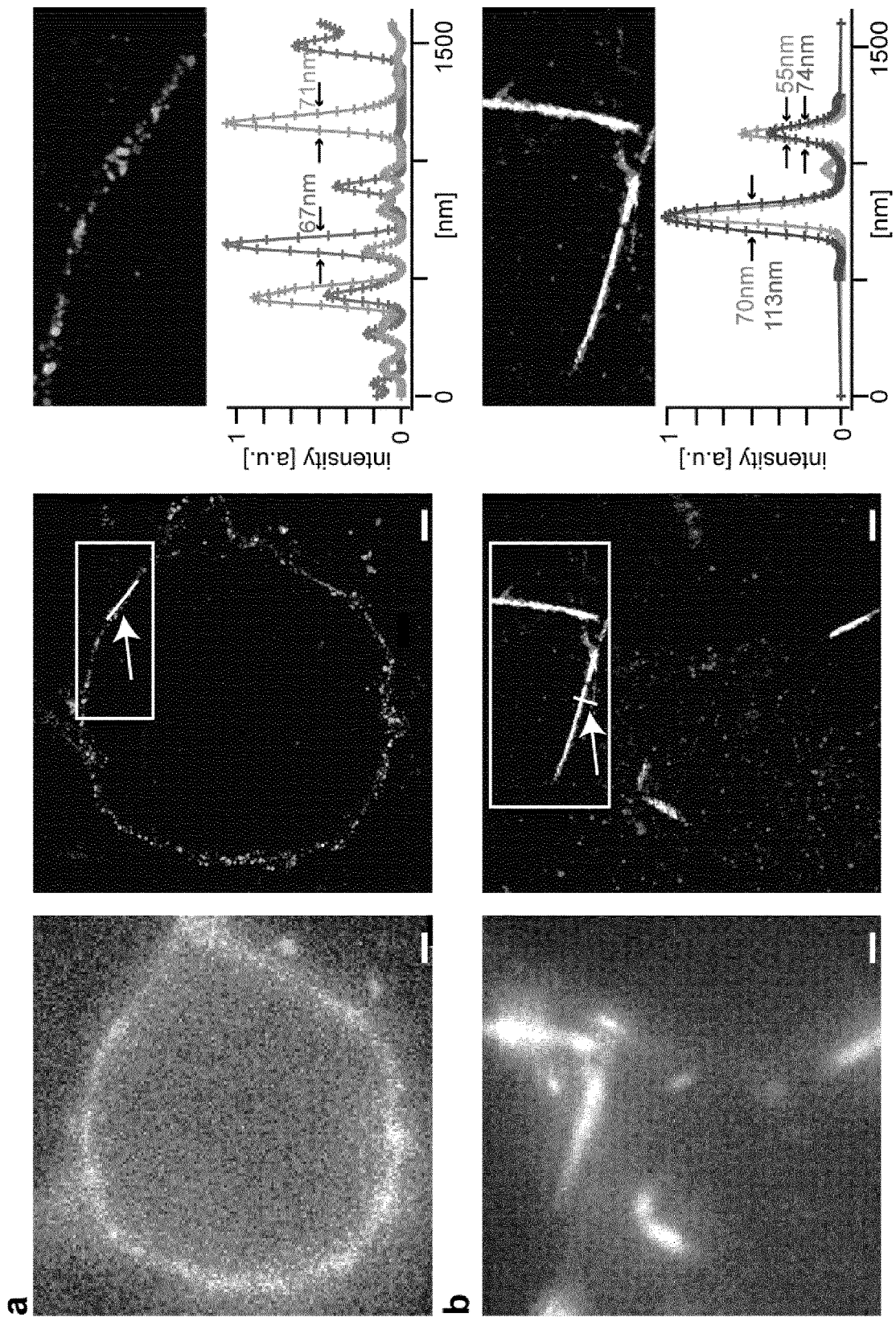
FIG. 3 shows SRM images of IRs and influence virus like particles (VLPs) after SPIEDAC and seSPIEDAC labeling. a) Widefield (left) and SRM (middle) images of IR$^{TAG}$ labeled according to FIG. 2a and FIG. 2b (Atto532 in magenta, Cy5 in cyan). On the right, inset from the middle panel and a line plot (across the line shown in middle panel, which is highlighted by an arrow). Width of marked peaks is given as full width half maximum (FWHM); b) Labeled VLPs analog to (a) with widefield (left), SRM (middle) and line plot. SRM images are displayed at a resolution of 45 nm as determined by Fourier Ring correlation (FRC). Scale bars are 1 µm.

Confocal images were processed using Fiji ImageJ (J. Schindelin, I. Arganda-Carreras, E. Frise, V. Kaynig, M. Longair, T. Pietzsch, S. Preibisch, C. Rueden, S. Saalfeld, B. Schmid, J. Y. Tinevez, D. J. White, V. Hartenstein, K. Eliceiri, P. Tomancak, A. Cardona, *Nature methods* 2012, 9, 676-682). For IR images, a median filter with a radius of two pixels was applied. ImageJ was also used to adjust contrast and brightness (only linear changes were applied) for display of both IR and VLP images (FIGS. 2, 9, 10). Individual color tiff files were then merged into single dual-color image by manually aligning the two channels.

Figure 4:
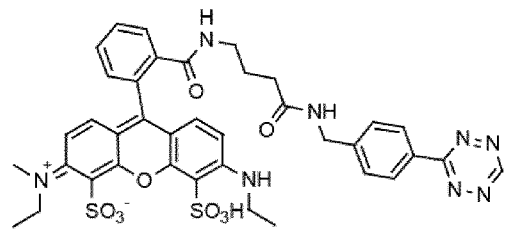
FIG. 4 shows compounds which are useful in the method of the present invention (and were used in the working examples): the non-fluorescent Me-Tet-NH$_2$ that is useful for quenching unreacted cyclooctenyl groups; and the fluorescent dyes azide-Cy3, H-Tet-Cy5, Me-Tet-Cy5, H-Tet-Atto532, Me-Tet-Cy3 and azide-Cy3.
Figure 4:
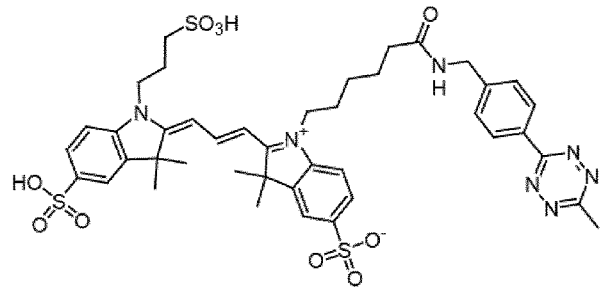
Figure 4:
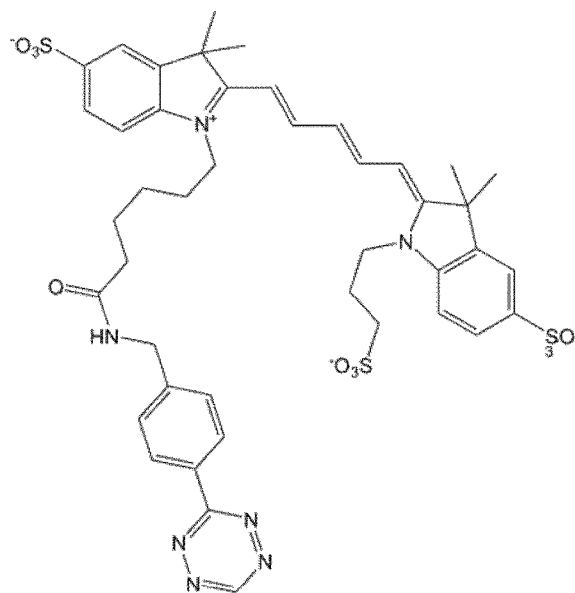
Figure 4:
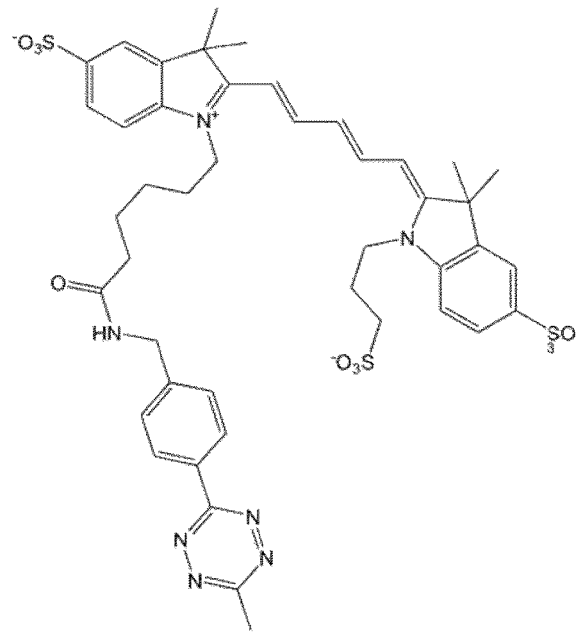
Figure 4:
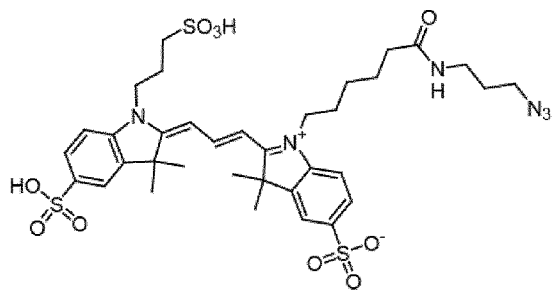
Figure 4:
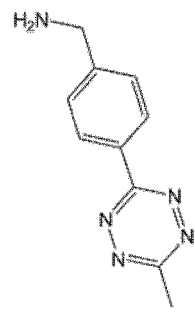
Figure 5:
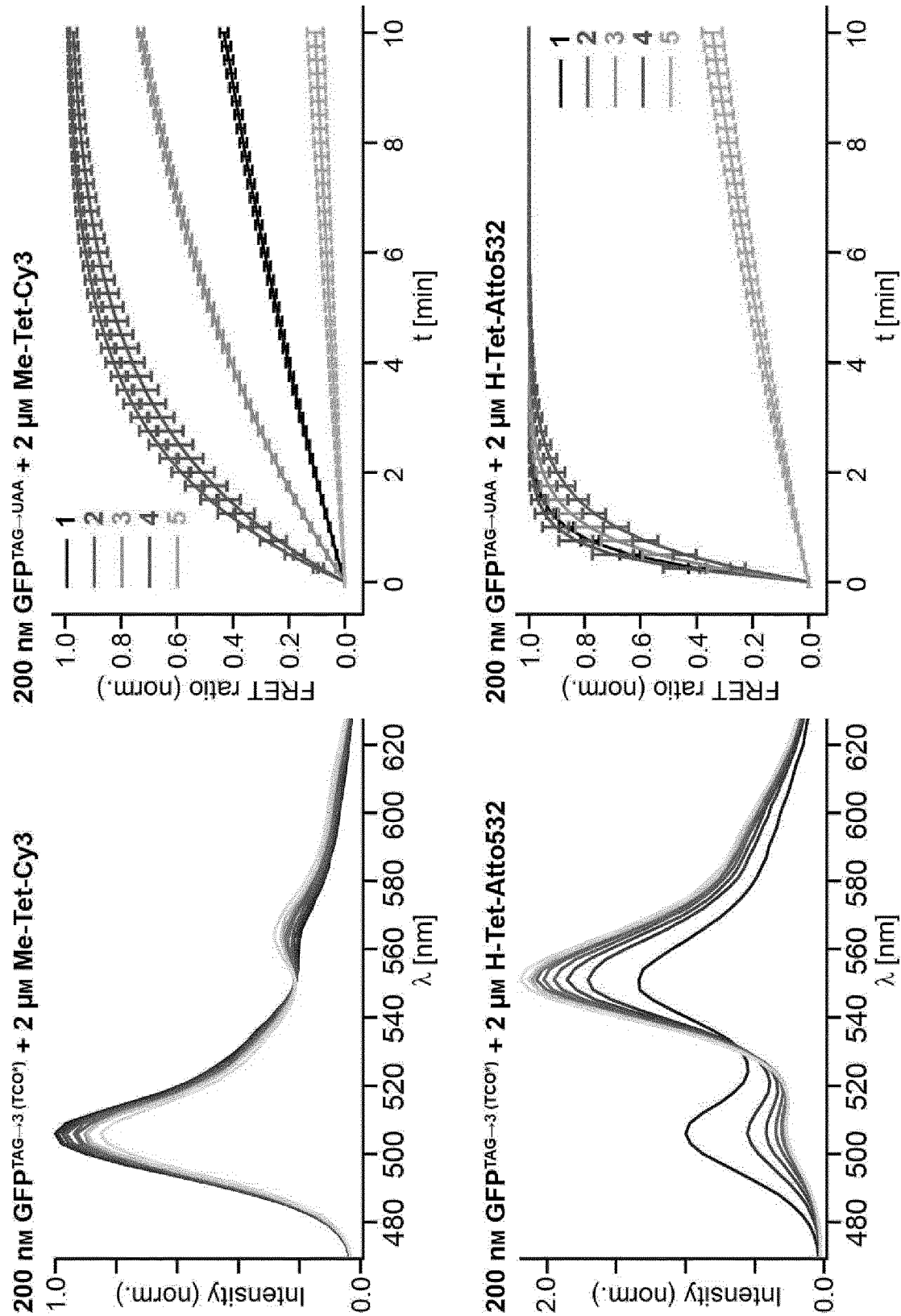
FIG. 5 shows the determination of reaction kinetics by FRET. The left panel shows exemplarily time dependent wavelength scans of GFP$^{TAG \to 3(TCO^*)}$ reacting with either Me-Tet-Cy3 (upper row) with H-Tet-Atto532 (lower row), respectively (black: first scan after addition of the probe; to grey: end of the reaction; norm.=normalized to GFP fluorescence at "0 min"). The D and A peak were used to calculate FRET (FRET=A/(A+D)) and plotted over time for all reactions in the right panel (upper row: Me-Tet-Cy3; lower row: H-Tet-Atto532). In order to normalize (norm.=normalized) the FRET data, experiments were separately fitted with the monoexponential model described herein. Subsequently, the first time point reaching maximal amplitude was calculated and the corresponding FRET ratio was used to normalize the FRET data (for every UAA and replicate independently). Finally, the three normalized separate experiments per UAA were averaged. Error bars indicate the standard deviation.

SRM processing was performed in IgorPro (WaveMetrics, Portland Oreg., USA). ImageJ was used for linear contrast-brightness adjustments for display. Molecules from SRM movies were localized in each frame using the "Localizer package" (Dr. Peter Dedecker, Katholieke University, Louvain, Belgium) for IgorPro. Individual molecules were fitted with a Gaussian to determine the (x,y) position of each blinking event of a single molecule. Localized positions were then analyzed by Fourier ring correlation to estimate the resolution of the data set, which was then used to determine the spot deviation in reconstructed SRM images (a) N. Banterle, K. H. Bui, E. A. Lemke, M. Beck, *J Struct Biol* 2013; b) R. P. Nieuwenhuizen, K. A. Lidke, M. Bates, D. L. Puig, D. Grunwald, S. Stallinga, B. Rieger, *Nature methods* 2013, 10, 557-562). Final images were displayed with an 8×8 nm$^2$ pixel size Example J Determination of Labeling Kinetics via a FRET Assay For observation of labeling kinetics, GFP$^{TAG \to UAA}$ was expressed with 1-5 (for structures of UAAs see FIG. 1a). *E. coli* lysate was adjusted to a final GFP concentration of 200 nM based on absorbance spectra. H-Tet-Atto532 7 or Me-Tet-Cy3 8 (see FIG. 4), respectively, were added to a final concentration of 2 µM and fluorescence spectra (excitation at λ=450 nm, emission λ=470-650 nm) were recorded at different time points. The experiments were carried out in a total volume of 2 ml and continuous stirring. 1 mM stocks of the dyes in DMSO were used. Successful labeling of GFP$^{TAG \to UAA}$ was monitored by Foerster resonance energy transfer (FRET) from the GFP-chromophore (serving as a Donor, D) to the synthetic fluorophore (Acceptor, A) when covalently attached. In the individual spectra this is visible by a decrease of GFP-fluorescence (around λ=503-506 nm) and a simultaneous increase of Atto532- (λ=551 nm) or Cy3-fluorescence (λ=563 nm), respectively, over time (shown exemplarily for GFP$^{TAG \to 3 \ (TCO^*)}$ in the left panel of FIG. 5). The right panel of FIG. 5 shows FRET plotted over time (in minutes) for the five different UAAs and the two different tetrazine probes. Note that time point "0 min" is defined as the time point about 15 s after pipetting the dye to the protein solution.

Resulting reaction kinetics were fit with a simple mono-exponential model according to $$GFP^{UAA\rightarrow}(t)=A_0(1-\exp(-kBt)),$$

where $A_0$ corresponds to the amplitude of the fit and is proportional to the initial GFP concentration, and B corresponds to the concentration of dye within the reaction. The rate constant k of the reaction is obtained from the fit under the assumption of constant B during the reaction (which is valid due to the large dye excess). Approximate rate constants under these experimental conditions measured at 20° C. are reported in Table 1 below and were obtained by fitting the FRET traces from three independent experiments for each UAA (different protein expressions, different days) and subsequent averaging.

TABLE 1

Reaction kinetics under tested experimental conditions

|  | Me-Tet-Cy3 [$M^{-1} \cdot s^{-1}$] | H-Tet-Atto532 [$M^{-1} \cdot s^{-1}$] |
|---|---|---|
| $GFP^{TAG\rightarrow 1}$ | 480 ± 190 | 16000 ± 2000 |
| $GFP^{TAG\rightarrow 2}$ | 2240 ± 340 | 21000 ± 4000 |
| $GFP^{TAG\rightarrow 3}$ | 1240 ± 250 | 13000 ± 2000 |
| $GFP^{TAG\rightarrow 4}$ | 3880 ± 470 | 10000 ± 1200 |
| $GFP^{TAG\rightarrow 5}$ | not determined | 670 ± 180 |

It is noted that Me-Tet-Cy3 derivatives are compared with H-Tet-Atto532 derivatives (due to commercial availability). However, it can be expected that the dye differences do not contribute markedly to the different observed reactivities.

All UAAs show reduced reactivity with Me-Tet than with H-Tet. However, the drop in reactivity is more dramatic for alkynes than for alkenes, leading to basically no detectable reactivity of SCO under the tested experimental conditions.

It is also noted that that the substituents of the tetrazines used in this work suggest that a strong inverse electron demand is not a major driving force for the speed of the described SPIEDAC reactions.

As shown in FIG. 5, for $GFP^{TAG\rightarrow 5}$ due to the absence of any reactivity, no stable FRET signal above background could be observed under our measurement conditions, and thus no approximation of reaction kinetics could be attempted.

Example J1

Reactivity of $GFP^{TAG\rightarrow 3}$, $GFP^{TAG\rightarrow 3a}$ and $GFP^{TAG\rightarrow 3b}$ with Cy5-Labeled Tetrazine Derivatives $GFP^{TAG\rightarrow UAA}$ was expressed in E. coli as described above in presence of 1, 3, 3a, 3b and 5. Subsequently, purified protein (Ni-NTA, see above) was labeled with H-Tet-Cy5 ("Tetrazine-C5" from Jena Bioscience) or Me-Tet-Cy5 ("6-Methyl-Tetrazine-Sulfo-Cy5" from Jena Bioscience) as described below. Kinetic experiments were performed using stopped-flow spectroscopy (SFM-3000, Bio-Logic). The kinetic of the labeling reaction was monitored by detecting the increase in fluorescence of Cy5 when covalently linked to the UAA of the respective GFP due to Fosters Resonance Energy Transfer (FRET) of the GFP-chromophore (serving as a Donor, D) to the fluorophore Cy5 (Acceptor, A). In the spectra, this is visible by an increase of Cy5-fluorescence over time (FIG. 13a).

FRET efficiency curves were not analyzed due to photophysical effects occurring in the GFP signal in the presence of an excess of Cy5. The measurements were done under pseudo-first order conditions in PBS pH 7.4 using 100 nM purified $GFP^{TAG\rightarrow x}$ protein and an excess (10-40 μM) of Cy5 dye (H-Tet-Cy5 or Me-Tet-Cy5). Data analysis was performed by fitting Cy5 fluorescence data to the inverse mono-exponential function $F(t)=A \cdot (1-e^{-K_{obs}t})+c$. The Akaike Information criterion was used to determine the time-point of the curve until which a mono-exponential function fitted better than a bi-exponential function. The different observed reaction rate constants $k_{obs}$ determined based on the fits were plotted against the concentration of Cy5 dye and the reaction constants K were obtained by doing a linear fit forcing it to 0 (FIG. 13b, Table 2). Experiments were performed in triplicates.

TABLE 2

Reaction constants K for labeling of $GFP^{TAG\rightarrow UAA}$ with tetrazine-Cy5 dyes

|  | Reaction with H-Tet-Cy5 K [$M^{-1} \cdot s^{-1}$] | Reaction with Me-Tet-Cy5 K [$M^{-1} \cdot s^{-1}$] |
|---|---|---|
| $GFP^{TAG\rightarrow 1}$ | 80400 ± 1100 | 390 ± 2 |
| $GFP^{TAG\rightarrow 3}$ | 30500 ± 600 | 700 ± 10 |
| $GFP^{TAG\rightarrow 3a}$ | 36500 ± 400 | 680 ± 10 |
| $GFP^{TAG\rightarrow 3b}$ | 12100 ± 200 | not determined* |
| $GFP^{TAG\rightarrow 5}$ | 1180 ± 80 | not determined* |

*not determined because reaction rate was too low to obtain reliable values

Example K

Figure 6:
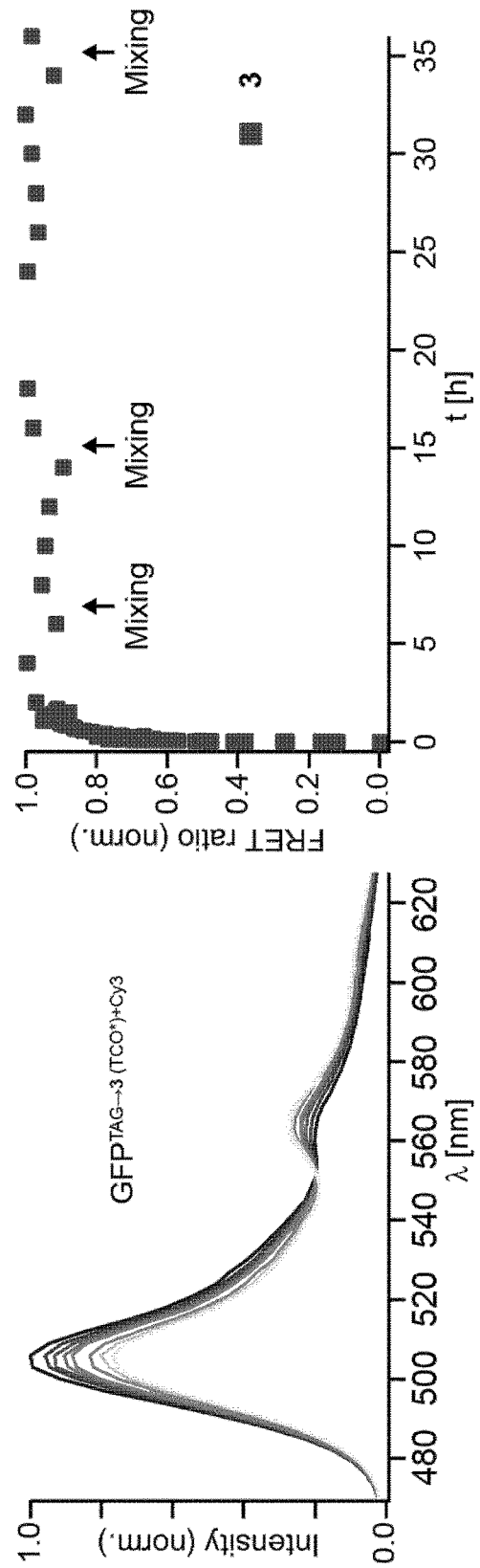
FIG. 6 shows a FRET assay carried out for 36 h for GFP$^{TAG \to 3}$. The left panel shows the time dependent wavelength scans of GFP$^{TAG \to 3+Cy3}$ (norm.=normalized to the GFP fluorescence at "0 min"). The D and A peak were used to calculate FRET (FRET=A/(A+D)) and plotted over time in the right panel (norm.=normalized to the maximal amplitude). The sample was not stirred (but occasionally mixed at the indicated time points). FRET values were constant over time.

Determination of the Long Time Stability of the Covalent Bond in Labeled Proteins To proof the stability of the formed covalent bonds between TCO* and the dye-Tet in a SPIEDAC reaction, long time FRET experiments were carried out. Basically, the same FRET assay as described above was used to test whether the fluorophores stays covalently attached to the protein or not over a period of 36 h. 200 nM $GFP^{TAG\rightarrow 3}$ were separately reacted with 2 μM Me-Tet-Cy3 at room temperature (rt) and the ratio between D and A fluorophore was followed over time. No data support a potential loss of the small molecule fluorophore over time (FIG. 6).

Figure 7:
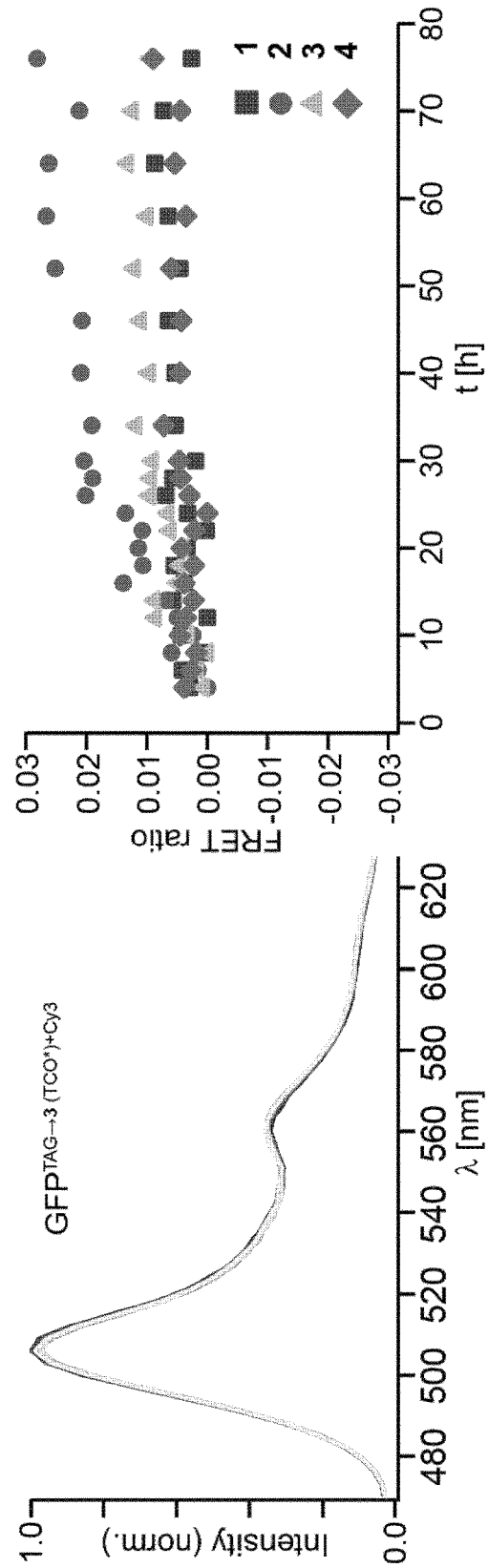
FIG. 7 illustrates the analysis of labeled GFP$^{TAG \to UAA+}$ $_{Cy3}$ (with 1-4) via FRET over more than three days. The left panel shows exemplarily time dependent wavelength scans of GFP$^{TAG \to 3+Cy3}$ (norm.=normalized to the GFP fluorescence at "0 min"). The D and A peak were used to calculate FRET (FRET=A/(A+D)) and plotted over time for 1-4 in the right panel. Note that the samples were occasionally mixed. In particular, 1 and 3 gave consistent FRET values over time.

In another experiment, Ni-NTA-purified $GFP^{TAG\rightarrow UAA}$ (1-4) was labeled with Me-Tet-Cy3 (2 h, 37° C.). Excess Me-Tet-Cy3 was filtered off (~2 h). 200 nM labeled $GFP^{TAG>UAA+Cy3}$ (with 1-4) were followed over time by FRET as described above. Note that the first data point was taken approximately 4 h after adding the tetrazine to the proteins. No significant changes between the FRET ratio measured after 4 h and after 76 h were observed (FIG. 7).

Example L

Determination of the Stability of the Different Trans-cyclooctenyl Isomers via $^1$H-NMR Previous studies showed the degradation of compounds with high ring strain, such as 1 and 4, in the presence of thiols (a) B. R. Varga, M. Kallay, K. Hegyi, S. Beni, P. Kele, Chemistry 2012, 18, 822-828; b) R. van Geel, G. J. Pruijn, F. L. van Delft, W. C. Boelens, Bioconjugate chemistry 2012, 23, 392-398). For example for trans-cyclooctenes, isomerization of the trans-form to its corresponding but by orders of magnitude less reactive cis-form has been observed when treated with L-cysteine and heat (J. Yang, J. Seckute, C. M. Cole, N. K. Devaraj, Angew Chem Int Ed Engl 2012, 51, 7476-7479).

¹H-NMR analysis showed that UAAs 1-5 dissolved in either 0.1 M NaOD in D$_2$O or DMSO-d6 were stable at room temperature (rt), 37° C., as well as at 60° C. over a period of 72 h (data not shown). Therefore, 0.1 M NaOH (for *E. coli* cells) and DMSO (for mammalian cells) are well suited solvents for the preparation of stock solutions for biological experiments. However, stock solutions were stored at −20° C. and thaw 30 min before usage.

¹H-NMR analysis showed that UAAs 2-4 dissolved in 1× deuterated PBS (dPBS) in D$_2$O (pH 7.4) mixed with 1,4-dioxane-d8 (v/v 1:1) were stable at room temperature (rt), 37° C., as well as at 60° C. over a period of 72 h (FIG. 8a). Taking the properties of the purified compounds into account, these conditions resemble the nearest physiological conditions possible, as they prevail in biological experiments (living cells, aqueous buffered solutions of proteins) ((a) B. R. Varga, M. Kallay, K. Hegyi, S. Beni, P. Kele, *Chemistry* 2012, 18, 822-828; b) R. van Geel, G. J. Pruijn, F. L. van Delft, W. C. Boelens, *Bioconjugate chemistry* 2012, 23, 392-398).

In order to test for stability against thiols, UAAs 2-4 were separately combined with two equivalents of cysteamine hydrochloride in dPBS/dioxane-d8 (v/v 1:1), NMR tubes were tightly sealed, and incubated at rt, 37° C., or 60° C. ¹H-NMR spectra were measured after 24 h of incubation and later time points (in case of 3). The ¹H-NMR data showed that all UAAs degrade over time in the presence of cysteamine in a temperature-dependent manner (FIG. 8b)—but with different speed. For all three trans-cyclooctene-containing UAAs, conversion of the trans-cyclooctenyl-form to its corresponding cis-cyclooctenyl-form was observed (FIG. 8b). While 2 and 4 isomerized equally fast (<5% of trans-isomer left after 24 h at 60° C.), 3 was found to be significantly more stable (~80% of trans-isomer left after 24 h at 60° C.). These numbers were obtained by comparing the integrals for the double bond protons and the —CHO— protons (if possible/applicable) before and after the heat treatment as it was done before by others for similar compounds ((a) B. R. Varga, M. Kallay, K. Hegyi, S. Beni, P. Kele, *Chemistry* 2012, 18, 822-828; b) R. van Geel, G. J. Pruijn, F. L. van Delft, W. C. Boelens, *Bioconjugate chemistry* 2012, 23, 392-398; J. Yang, J. Seckute, C. M. Cole, N. K. Devaraj, *Angew Chem Int Ed Engl* 2012, 51, 7476-7479). Observations at different temperatures were consistent with the expectation that the higher the temperature, the faster/easier the isomerization. Isomerization to the cis-form continued in samples kept at rt or 37° C. after 24 h (data not shown).

To show that also 3 (TCO*) can be completely converted to its cis-form in the presence of thiols at 60° C., incubation at 60° C. was continued and ¹H-NMR spectra were measured beyond the time points indicated in FIG. 8c. Even after ten days (240 h), more 3 (TCO*) was left in its trans-form than for 2 (TCO) and 4 (TCO#) after 24 h incubation at 60° C. with two equivalents of cys-teamine.

Further, the axial TCO* isomer 3a was found to be more stable, i.e. less prone to decay (mostly by conversion into cis-form) than the equatorial TCO* isomer 3b. The half-life of 3a was determined to be close to two days at 60° C. and 34 d at 37° C., while 3b decayed under these conditions within a few hours (FIGS. 14a and 14b).

Example M

SPAAC Labeling of Insulin Receptor with/without Endocytosis Blocker

HEK293T cells were transfected with pEGFPN1_IR$^{K676TAG}$ and pCMV tRNA$^{Pyl}$/PylRS$^{AF}$ plasmids as described above. After the transfections, cells were incubated overnight with BCN. On the following morning, cells were rinsed with serum-free DMEM. 2 h later labeling was performed. As shown in FIG. 2b, azide labeling with 10 min incubation and 10 μM of the dye did not give any obvious labeling results. In order to optimize the azide labeling reaction, we increased the concentration of the Cy5-azide to 50 μM and incubated it for 2 h at 37° C. After the labeling, cells were kept at 37° C. before they were fixed and taken to the confocal microscope (see above for details). FIG. 9a shows specific membrane labeling in the Cy5-channel (right panel) which is co-localized with the GFP-channel (left panel) from the IR$^{TAG}$. In addition, in the Cy5-channel we observed very high background and unspecific dye sticking inside the cells, probably due to the prolonged dye incubation step. Only when the endocytosis blocker (Dynasore hydrate, Sigma-Aldrich, Frankfurt, Germany) was applied (80 μM solution in serum-free DMEM, 20-30 min prior to the labeling and during the Cy5-azide incubation) we observed less non-specific dye accumulations (FIG. 9b).

In a further experiment, the transfected cells were incubated with 250 μM of 3, 3a or 3b for 8 h. On the following day, the cells were labelled with 5 μM H-Tet-Cy5 or Me-Tet-Cy5 for 10 min at 37° C. in DMEM. After changing the medium for fresh DMEM, the cells were incubated at 37° C. for another 1-2h. Afterwards, the cells were fixed and analyzed via confocal microscopy (see above for details). As shown in FIG. 15, incubation with 5 μM H-Tet-Cy5 produced reliable labeling of all three fusion proteins, GFP-IR$^{TAG->3}$, GFP-IR$^{TAG->3a}$ and GFP-IR$^{TAG->3b}$. When cells were incubated with the slower reacting Me-Tet-Cy5, no staining was detected for GFP-IR$^{TAG->3b}$, while GFP-IR$^{TAG->3}$ and GFP-IR$^{TAG->3a}$ exhibited a detectable staining that was somewhat weaker than with H-Tet-Cy5 labeling.

Example N

IR Dual-Color Labeling Controls

HEK293T cells were transfected with pEGFPN1_IR$^{TAG}$ and pCMV tRNA$^{Pyl}$/PylRS$^{AF}$ plasmid as described above. After transfections, cells were first pulsed with UAA1 and then chased with UAA2 (see FIG. 2).

Since TCO* can react with both Me-Tet (applied during the 1$^{st}$ labeling step) and H-Tet (applied during the 2$^{nd}$ labeling step), it was needed to exclude the possibility that if not all TCO* reacts off in the first step, it could get labeled by H-Tet in the second step. Full consumption of TCO* in the first labeling step is a requirement for an orthogonal dual labeling design, as otherwise it would yield an ambiguous result. Such a phenomenon could e.g. occur, if cells express high concentration of TCO*, so that it does not get fully consumed in the first labeling reaction with Me-Tet. To test for this, the following control experiments were performed:

After transfections, cells were first pulsed with UAA1 (TCO*) and then chased with UAA2(PrK), see FIG. 2. Propargyllysine (PrK) is an aliphatic alkyne and does not participate in SPAAC or SPIEDAC reactions and functions here as an inert UAA that is incorporated by the same tRNA/RS$^{AF}$ in similar yields as TCO*, BCN and SCO (T. Plass, S. Milles, C. Koehler, C. Schultz, E. A. Lemke, *Angew Chem Int Ed Engl* 2011, 50, 3878-3881; T. Plass, S. Milles, C. Koehler, J. Szymanski, R. Mueller, M. Wiessler, C. Schultz, E. A. Lemke, *Angew Chem Int Ed Engl* 2012, 51, 4166-4170; D. P. Nguyen, H. Lusic, H. Neumann, P. B. Kapadnis, A. Deiters, J. W. Chin, *Journal of the American Chemical Society* 2009, 131, 8720-8721; A. Borrmann, S. Milles, T. Plass, J. Dommerholt, J. M. Verkade, M. Wiessler, C. Schultz, J. C. van Hest, F. L. van Delft, E. A. Lemke, Chembiochem 2012, 13, 2094-2099). Then Me-Tet-Cy5 (5 µM in serum-free DMEM, 10 min at 37° C.) was applied first. In a second labeling step, H-Tet-Atto532 was applied analyzed using the Mascot algorithm and the results verifying successful incorporation of 3 and 4 are summarized in Table 3. GFP$^{TAG \to 5}$ was analyzed as a positive control.

TABLE 3

Mass spectrometric validation of formation of GFP$^{TAG \to UAA}$

| Protein | Monoisotopic mass (calc) [Da] | Match mass, found [Da] | Peptide sequence (X = amber TAG site) |
|---|---|---|---|
| GFP$^{TAG \to 3}$ | 2075.07864 | 2075.07944 | FSVSGEGEGDATXGKLTLK |
| GFP$^{TAG \to 4}$ | 2075.07864 | 2075.07724 | FSVSGEGEGDATXGKLTLK |
| GFP$^{TAG \to 5}$ | 2073.06300 | 2073.06368 | FSVSGEGEGDATXGKLTLK |

(compare FIG. 2). As expected, very high Me-Tet-Cy5 signal could be seen (FIG. 10a). However, in the Atto532 channel we can also observe some fluorescence. Since only TCO* was present as a reactive UAA, it indicates that most (>80%), but not all TCO* was consumed in the first labeling step. This phenomenon depends on the cell expression level, concentration of dye, labeling time and temperature. To establish a robust protocol that works across a broad range of parameters, it was found practical to introduce a quenching step. To this purpose, a high concentration of the small Me-Tet (NH$_2$-Me-Tet) was used, which is compared to a dye relatively cheap to obtain, can be rapidly perfused and washed off from cells. It was determined that a 2 min pulse (at RT) of 50 µM, dissolved in serum-free DMEM reacted with unconsumed TCO* in all tested experiments (FIG. 10a). It was thus continued using the quencher in all subsequent SPIEDAC-seSPIEDAC labeling experiments.

Dual-color labeling after pulsing the cells with UAA1 (TCO*) and chasing them with UAA2 (BCN) was also performed. Me-Tet-Cy5 (5 µM in serum-free DMEM, 10 min at 37° C.) targeting TCO* labeling was followed by quenching as described above. In the second labeling step, H-Tet-Atto532 targeting BCN was applied. As shown in FIG. 10b, TCO* was successfully labeled, but due to the reactivity between BCN and high concentrations of Me-Tet from the quencher, no signal in the Atto532 channel was observed. This shows that under the tested conditions, the remaining reactivity of BCN vs Me-Tet (in line with the kinetics from FIGS. 5, 6 and 7 and the gel assay in FIG. 2) does not allow for a dual-color labeling approach orthogonal to the reaction of TCO* with Me-Tet.

Also shown in FIG. 10c, are the repetitions of the same control experiment (as described above for IR) with TCO* and PRK for virus like particles (VLPs,) using the same labeling and quenching conditions (compare FIG. 2c).

To test for the possibility of non-specific labeling in FIG. 10d, the larger field of view (compare FIG. 2b) is shown here. It is clear from this image that only pEGFPN1_IR$^{K676TAG}$ positive cells are labeled with H-Tet-Atto532/Me-Tet-Cy5.

Example O

Mass Spectrometry Validation

Figure 1:
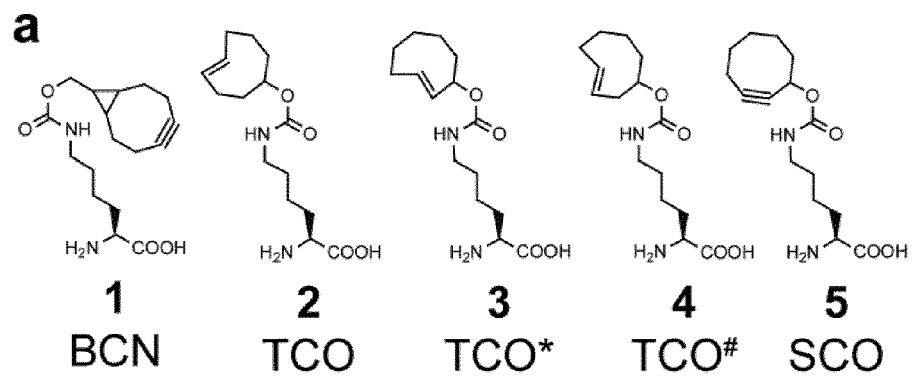
FIG. 1 shows: a) Structures of UAAs; b) Coomassie-stained SDS-PAGE gel of purified GFp$^{TAG \to UAA}$ expressed in absence (−) or presence (+) of UAAs. GFP band (arrow points to 35 kDa molecular weight marker) is only present when Y39TAG mutation is successfully suppressed. TCO isomers (TCO*, TCO$^{\#}$) show higher expression yield than the TCO; c) TCO isomers were mixed with cysteamine hydrochloride and $^1$H-NMR spectra (only signals relevant for observing the cis-trans configuration are shown, x-axis is ppm) were measured at multiple time points and temperatures (for details see FIG. 8). The plot shows chemical shift data measured at 0 h, room temperature (red) and 24 h, 60° C. (blue). Black dots indicate the signals of the double bond and the —CHO— protons of the trans-forms of TCO* and TCO$^{\#}$. Black arrows indicate the signals belonging to the corresponding cis-isomers that form upon thiol and heat treatment. While all three TCOs degrade over time in the presence of thiols, TCO* shows the highest chemical stability (~80% of trans-isomer left after 24 h); d) Purified GFP$^{TAG \to UAA}$ (200 nM) was reacted with two tetrazines (15 µM, 20 min, 37° C.). and azide (45 µM, 10 h, 37° C.). Shown is the result from the UV scanned as well as Coomassie-stained SDS-PAGE gel.
Figure 1:
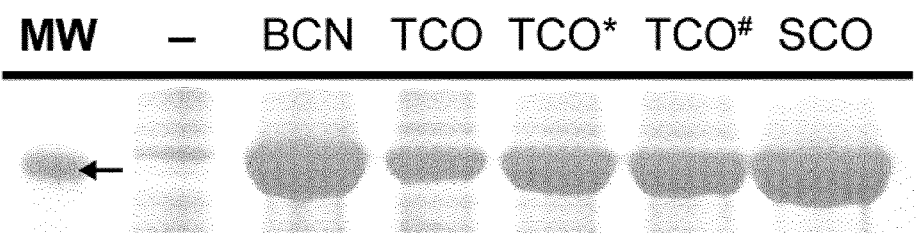
Figure 1:
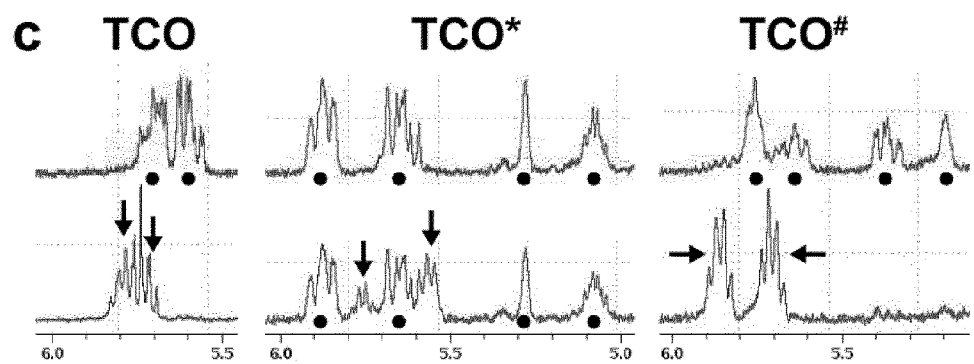
Figure 1:
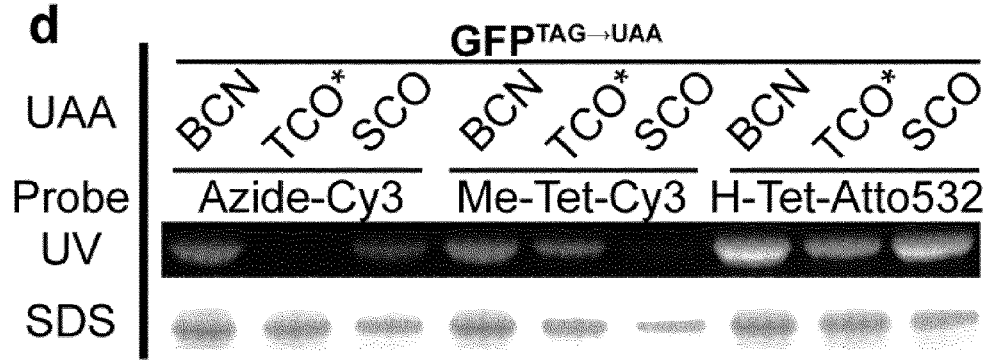
Figure 8:
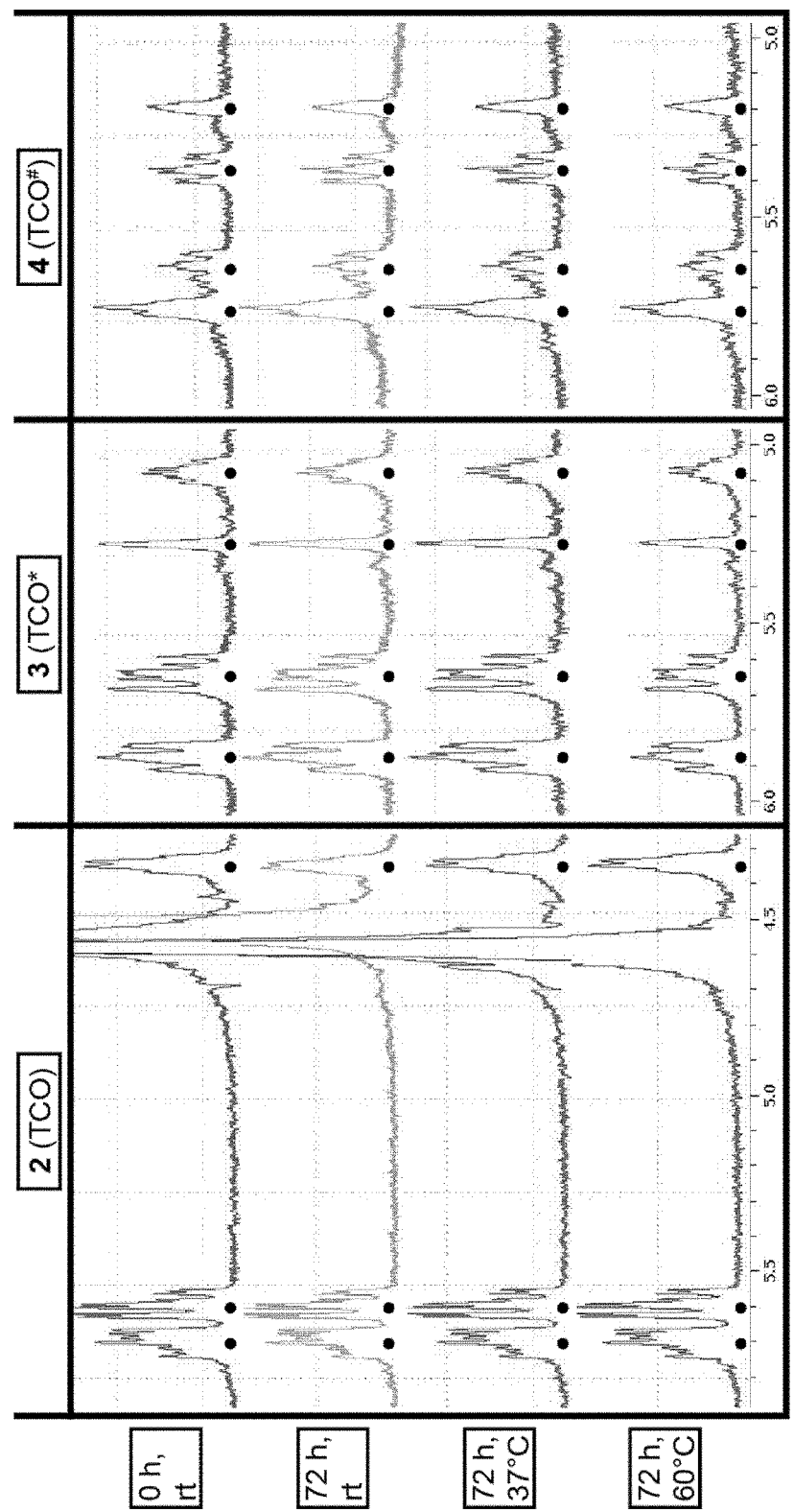
FIG. 8 shows a) $^1$H-NMR spectra of UAAs 2 (TCO), 3 (TCO*), and 4 (TCO$^{\#}$) recorded in dPBS/dioxane-d8 (v/v 1:1) after incubation at either room temperature (rt; green lines), 37° C. (red lines), or 60° C. (blue lines) for 72 h. According to these data, all compounds remained un-changed compared to the $^1$H-NMR spectra recorded directly after dissolving the UAAs in dPBS/dioxane-d8 (purple lines). Black dots indicate the signals of the double bond and the —CHO— protons of the trans-form; b)
Figure 8:
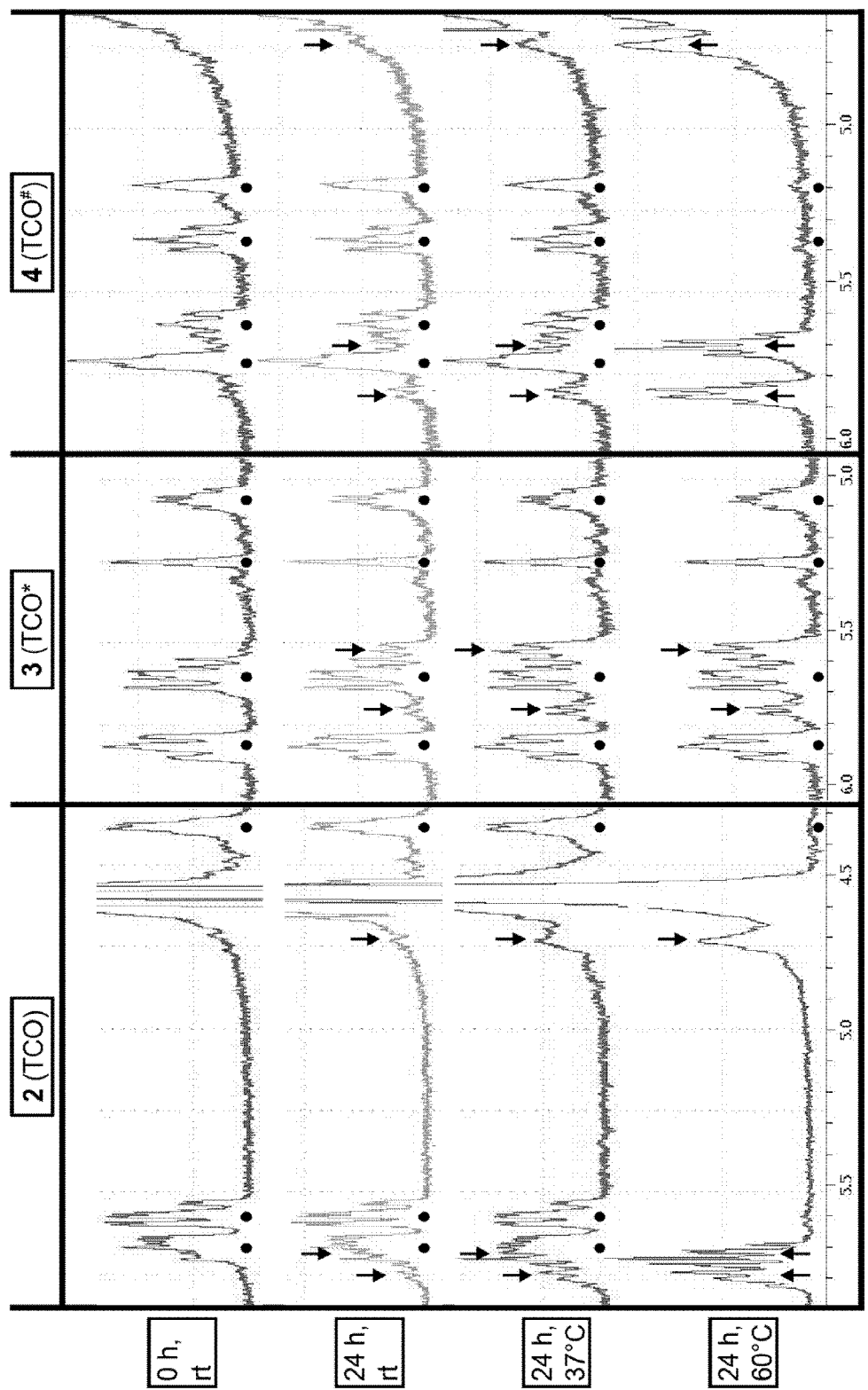
Figure 8:
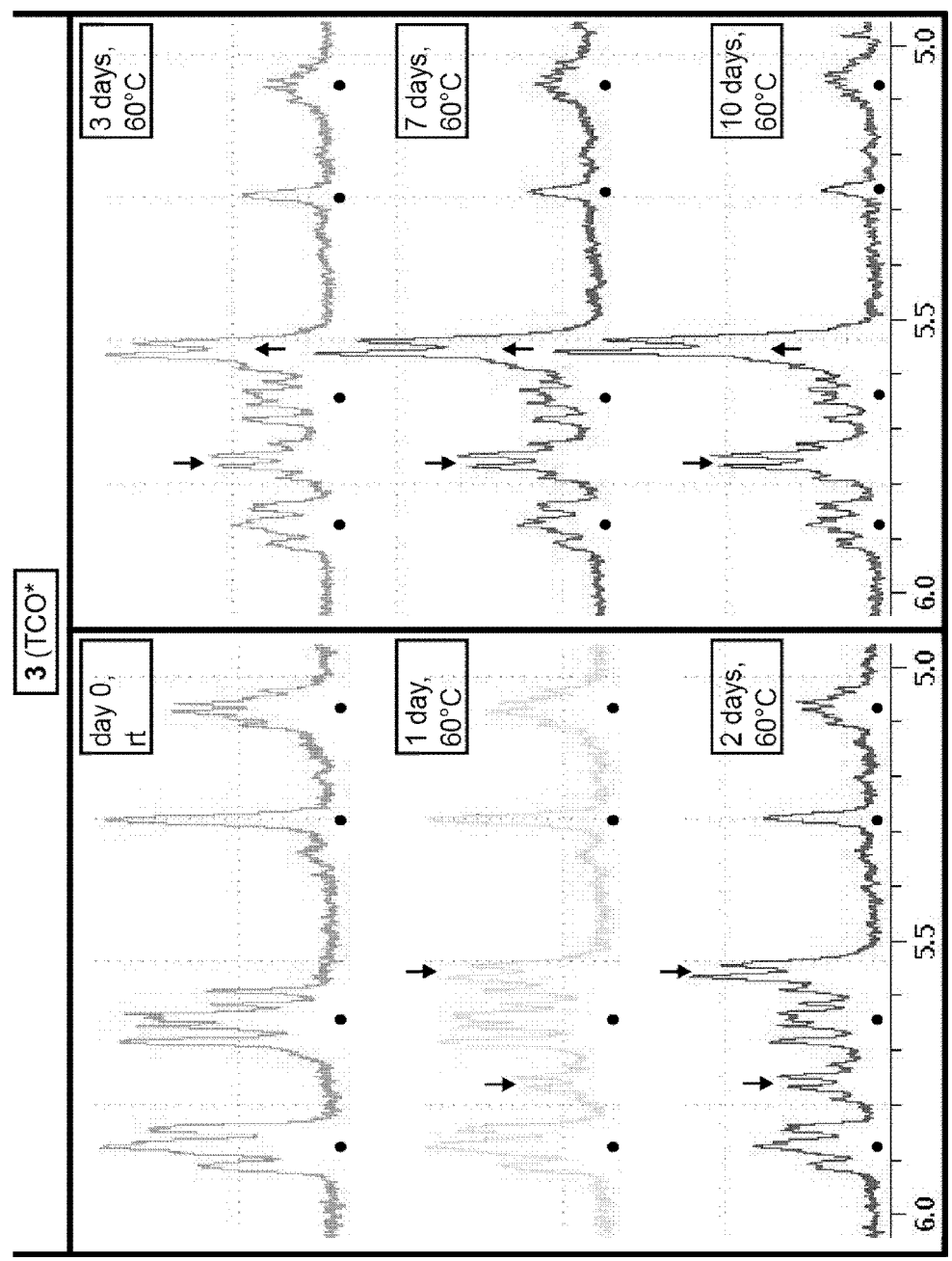

For mass spectrometric validation corresponding to protein shown (compare FIG. 1), GFP$^{TAG \to 3}$ and GFP$^{TAG \to 4}$ expressed in E. coli harboring the tRNA$^{Pyl}$/PylRS$^{AF}$ plasmid were excised and subsequently digested with trypsin (tryp) following standard protocols for high resolution peptide mass analysis. Peptides were analyzed using an Orbitrap mass spectrometer (Thermofisher, USA). The data was Test expressions with a GFP$^{TAG}$ reporter construct, which only gives full length expression and hence fluorescence if the amber mutation at position Y39 is suppressed, show that TCO* and TCO$^{\#}$ are accepted by the tRNA$^{Pyl}$/PylRS$^{AF}$ pair approximately three times better than the original cyclooct-4-ene TCO (FIG. 1b, Table 3 for mass spectrometry data), yielding about 10 mg from a 1 I E. coli expression culture. FIGS. 5, 6 and 7 show that all three TCOs maintain similar reactivity in SPIEDAC reactions. However, trans-cyclooctene is known to have chemical stability issues and tends to isomerize to the nonreactive cis-form especially in the presence of thiols (J. Yang, J. Seckute, C. M. Cole, N. K. Devaraj, Angew Chem Int Ed Engl 2012, 51, 7476-7479). Since thiols are abundant in the cytosol of mammalian cells, this can lead to interference with UAA biostability during long-term expressions. NMR measurements shown in FIG. 1c and FIG. 8 showed that TCO* has an at least 10-fold higher stability in the presence of thiols, which indicated efficient shielding of the trans-double bond towards thiols by the proximity of the carbamate bond.

The tRNA$^{Pyl}$/PylRS$^{AF}$ mutant pair permits encoding TCO* and BCN which can undergo SPIEDAC and SPAAC reactions, respectively (FIG. 1d). To explore the potential of this UAA pair for dual-color labeling of live cells, it was used for pulse-chase labeling of the insulin receptor (IR). Function and receptor recycling of IR are topics of high contemporary relevance due to its central role in diabetes, as well as newly emerging gene regulatory roles (K. Siddle, Journal of molecular endocrinology 2011, 47, R1-10; R. Sarfstein, H. Werner, Endocrinology 2013, 154, 1672-1679). A position located on the extracellular side of the protein (K676) was picked for an amber mutation and expressed the IR$^{TAG}$ in the presence of a plasmid coding for the tRNA$^{Pyl}$/PylRS$^{AF}$ in HEK293T cells.

Then the pulse-chase experiment as outlined in FIG. 2a was performed, where the growth medium was first pulsed for 4 h with 1$^{st}$ UAA (TCO*), followed by a 4h-chase with 2$^{nd}$ UAA (BCN). IR$^{TAG}$ was labeled first with azide-Cy5 and later with Me-Tet-Cy3, each incubated for 10 min on living cells. As can be seen in FIG. 2b (1$^{st}$ panel), confocal imaging allowed visualizing the membrane staining of IR$^{TAG \to TCO^*}$ with Me-Tet-Cy3 from the SPIEDAC reaction. The short labeling of IR$^{TAG \to BCN}$ with azide-Cy5 gave no results. As detailed in FIG. 9, this could be attributed to the speed of the SPAAC reaction which is three to four orders of magnitudes slower than the SPIEDAC reaction.

The cyclooctynyl-lysine derivative (SCO) (FIG. 1a) is accepted by the same tRNA$^{Pyl}$/PylRS$^{AF}$ pair in similar yields as TCO*. While TCO* reacts with H-Tet and Me-Tet with reactions rates of >1000 1/Ms in in vitro kinetic assays and labeling experiments, SCO shows no substantial reactivity with Me-Tet under the tested conditions (see FIGS. 5, 6 and 7 for reaction kinetics, FIG. 1d). However, SCO still reacts at about two orders of magnitude faster in a SPIEDAC reaction with H-Tet than BCN in a SPAAC reaction with azide. The pulse-chase experiment was repeated with TCO* and SCO (FIG. 2a), followed with labeling with Me-Tet-Cy5, and then H-Tet-Atto532 for 10 min. As shown in FIG. 2b, this combination resulted in bright labeling of the IR in the plasma membrane for both channels. SCO selectively reacts with H-Tet but not Me-Tet on the time scale of our experiments which thus results in a reaction that is orthogonal to the SPIEDAC between TCO* and Me-Tet. This subreaction type is referred to herein as "selectivity enhanced SPIEDAC" (seSPIEDAC). It is noted that as TCO* is highly reactive with both, Me-Tet and H-Tet, experimental conditions must be chosen to ensure that all TCO* is consumed before proceeding to the second labeling step (see FIG. 10 for details).

Furthermore, it is shown in FIG. 1d and FIG. 10 that further increasing the speed of seSPIEDAC by using the highly ring strained BCN instead of SCO is not possible due to reactivity of BCN towards Me-Tet (FIGS. 5, 6 and 7).

Since Cy5 and Atto532 are commonly used for localization-based SRM, dual-color SRM measurements were performed (M. Heilemann, S. van de Linde, M. Schuttpelz, R. Kasper, B. Seefeldt, A. Mukherjee, P. Tinnefeld, M. Sauer, *Angew Chem Int Ed Engl* 2008, 47, 6172-6176; M. Bates, B. Huang, G. T. Dempsey, X. Zhuang, *Science* 2007, 317, 1749-1753; J. Folling, M. Bossi, H. Bock, R. Medda, C. A. Wurm, B. Hein, S. Jakobs, C. Eggeling, S. W. Hell, *Nature methods* 2008, 5, 943-945). The confocal (FIG. 2) and widefield images showed overlapping plasma membrane staining of IR in both colors after dual-color labeling of TCO* and SCO. However, SRM revealed a heterogeneous distribution of IR clusters at the membrane (FIG. 3a). Notably, clustering has also been observed for other growth factor receptors using SRM studies (S. Wilmes, M. Staufenbiel, D. Lisse, C. P. Richter, O. Beutel, K. B. Busch, S. T. Hess, J. Piehler, *Angew Chem Int Ed Engl* 2012, 51, 4868-4871)

To demonstrate the generality of the approach of the invention, labeled virus-like particles (VLPs) were assembled by the co-expression of influenza virus proteins hemagglutinin (HA) and matrix protein 1 (M1) (for review see J. S. Rossman, R. A. Lamb, *Virology* 2011, 411, 229-236). Viral genomes are compact and often contain overlapping genes, which makes inserting genetically-encoded tags into viral proteins a particular challenge. We generated a TAG mutant of HA and expressed it together with M1 and the tRNA$^{Pyl}$/PylRS$^{AF}$ in HEK293T cells. We repeated the pulse-chase protocol using TCO*, SCO and labeled with Me-Tet-Cy5 and H-Tet-Atto532. As shown in FIG. 2c, Atto532 and Cy5 stained filamentous protrusions, corresponding to assembled VLPs, became visible. The enhanced resolution of SRM makes it possible to visualize individual filaments (FIG. 3b). Notably, there is significant spatial overlap between the two colors, suggesting that proteins translated at different times are incorporated into the same assembling VLPs.

In summary, the genetically encoded SPIEDAC reaction was tuned into two mutually orthogonal SPIEDAC reactions which can be used to perform rapid labeling of proteins in living cells. This expands the existing repertoire of biocompatible "click" labeling methods using an expanded genetic code from SPIEDAC & SPAAC to SPIEDAC & seSPIEDAC & SPAAC. The two rapid SPIEDAC reactions allowed SRM compatible dual-color labeling experiments in mammalian cells, while the slow reactivity of SPAAC seemed insufficient for rapid high contrast labeling of live cells.

TCO* is an improved TCO with higher biostability and incorporation efficiency. TCO* reacts rapidly with both tested tetrazines (Me-Tet, H-Tet), while BCN has comparatively much more reduced reactivity towards Me-Tet. Under the performed experimental conditions, SCO only reacted with H-Tet and not Me-Tet. Dual-color labeling was achieved using a promiscuous tRNA/RS pair and a pulse-chase approach. The labeling step is done in living cells, creating new possibilities for studying protein fate with very high resolution. Combining the dual-color labeling of the invention with genetic switches, such as temperature sensitive mutants and promoter control, could enable distinct proteins to be labeled. However, the labeling chemistries of the present invention are general and can also be directly applied to specific encoding via two distinct codons.

The small size of the UAA tag, in comparison with other genetically-encoded fluorescent tags, is a major advantage especially for studies of complex protein assemblies such as IR and HA, where multiple functional interactions with other proteins and lipids might be influenced by larger tags in unpredictable ways. In particular, viral genomes are frequently extremely compact and do not tolerate large modifications. The need for changing only a single codon, thus dramatically increases the chance of finding permissive sites that do not alter protein function.

Since the techniques of the present invention rely on the generic ligation mechanism of two tuned SPIEDAC reactions, it will thus be compatible with any dye developments suitable for live intracellular labeling and also applicable to a broad range of other disciplines for installing tags, such as MRI and PET studies.

Example P $^1$H-NMR Assay to Prove the Orthogonality of seSPIEDAC and SPIEDAC Reactions Stock solutions of the dienophiles in DMSO-d6 with a final concentration of 10 mm were prepared. A 20 mm stock of the formic acid salt of (4-(6-methyl-1,2,4,5-tetrazine-3-yl)phenyl)methanamine (termed as methyl tetrazine or Me-Tet-NH$_2$) in DMSO-d6 was prepared, too. As control experiment, either the dienophile or the diene (Me-Tet-NH$_2$) were mixed with DMSO-d6 1:1 (v/v; 760 µl total volume) to yield a final concentration of 5 mm or 10 mm, respectively, in the NMR tube. To confirm whether a dienophile reacts with the diene (Me-Tet-NH$_2$) or not, the corresponding stocks were mixed 1:1 (v/v; 760 µl total volume) to yield a final concentration of 5 mm of the dienophile and 10 mm of the diene in the NMR tube. The samples were incubated for 10 min at room temperature before analyzed by $^1$H-NMR.

Comparison of the $^1$H-NMR spectra of the dienophile and the diene with the reaction mixture showed that the trans-cyclooct-2'-ene had completely reacted with the tetrazine 10 min after mixing the trans-cyclooct-2'-ene with the tetrazine (FIG. 11a). No signals corresponding to the trans-double bond (black dots in the middle spectrum) were detected after incubation. As expected, remaining tetrazine was detected (black dots in the bottom spectrum) because it was used in excess. New signals in the aromatic region (upper spectrum) were detected corresponding to the newly formed reaction products. The reaction of a different isomer of trans-cyclooct-2'-ene was found to be slower than the reaction of the trans-cyclooct-2'-ene (FIG. 11b). The black arrows indicate the decrease in the integral of the trans-double bond protons and the appearance new signals in the aromatic region upon reaction (upper spectrum). The reaction can be driven to completion by either extending the reaction time, increasing the temperature, or by using higher excess of the tetrazine.

Conversely, neither the 5-norbornene-2-ol (endo- and exo-isomer) nor the cyclooctyne moieties reacted at all with the tetrazine (indicated by the black dots in FIG. 11c, FIG. 11d and FIG. 11e). No new signals were detected within 10 minutes after mixing the dienophile with the tetrazine. The reaction with bicyclononyne moiety (two isomers), however, took place, although it had not yet completely reacted with the tetrazine 10 min after mixing (upper spectrum of FIG. 11f). The reaction of this reaction pair was thus found to be slower than the reaction of the reaction pair in FIG. 11a. The black arrows indicate newly appearing signals upon reaction (upper spectrum). The reaction can be driven to completion by either extending the reaction time, increasing the temperature, or by using higher excess of the tetrazine.

Similar experiments carried out in 1× deuterated PBS (dPBS) in $D_2O$ (pH 7.4) mixed with 1,4-dioxane-d8 (v/v 1:1) gave the same results.

Abbreviations

AcF=p-acetylphenylalanine
AcOH=acetic acid
aq.=aqueous
Ar=argon/inert gas atmosphere
BCN=N-ε-((1R,8S,9S)-bicyclo[6.1.0]non-4-yn-9-methyloxy)carbonyl)-L-lysine (FIG. 1a: compound 1)
Boc- L-Lys-OH=N-α-tert-butyloxycarbonyl-L-lysine
brine=sat. aq. NaCl solution
calcd=calculated
cHex=cyclohexane
conc.=concentrated
DBU=1,8-diazabicyclo[5.4.0]undec-7-ene
DCM=dichloromethane
DIEA=N,N-diisopropylethylamine
DMF=dimethylformamide
DMSO=dimethylsulfoxide
eq.=equivalent(s)
EtOH=ethanol
EtOAc=ethyl acetate
FC=flash chromatography
Fmoc-Lys-OH=N-α-(9-fluorenylmethyloxycarbonyl)-L-lysine
FRET=fluorescence resonance energy transfer, also called Förster resonance energy transfer
MeOH=methanol
GFP=green fluorescent protein
$GFP^{WT}$=wildtype GFP
$GFP^{TAG}$=GFP encoded by a sequence comprising amber stop codon TAG at permissive site 39
$GFP^{TAG->x}$=$GFP^{TAG}$ wherein compound x has been incorporated at amber-encoded site, e.g., $GFP^{TAG->1}$=$GFP^{TAG}$ wherein compound 1 has been incorporated at amber-encoded site
h=hour(s)
$I_{GFP}$=average intensity of GFP
IR=insulin receptor
GFP-$IR^{TAG}$=GFP-IR fusion construct encoded by a sequence comprising amber stop codon TAG at permissive site 676 of the IR
GFP-$IR^{TAG->x}$=GFP-$IR^{TAG}$ fusion wherein compound x has been incorporated at the amber-encoded site, e.g., GFP-$IR^{TAG->1}$=GFP-$IR^{TAG}$ fusion wherein compound 1 has been incorporated at site 676 of the IR
MBP=maltose binding protein
$MBP^{TAG}$=MBP encoded by a sequence comprising amber stop codon TAG at permissive site 38 and a C-terminal His tag
$MBP^{TAG->1}$=$MBP^{TAG}$ wherein compound 1 has been incorporated at amber-encoded site
$mCherry^{WT}$=wildtype mCherry
$mCherry^{TAG->1}$=mCherry wherein compound 1 has been incorporated at amber-encoded site
meas.=measured
min=minutes
NLS=nuclear localisation sequence
$OD_{600}$=optical density at 600 nm
o/n=over night
PBS=phosphate buffered saline
PMSF=phenylmethylsulfonylfluorid
RS=aminoacyl tRNA synthetase
rt=room/ambient temperature (20-25° C.)
sat.=saturated
SCO=N-ε-((Cyclooct-2-yn-1-yloxy)carbonyl)-L-lysine (FIG. 1a: compound 5)
SD=standard deviation
SDS-PAGE=sodium sodecyl sulfate polyacrylamide gel electrophoresis
smFRET=single molecule observation of FRET
TAMRA=tetramethylrhodamine
TB=Terrific Broth
TCO=N-ε-((trans-Cyclooct-4-en-1-yloxy)carbonyl)-L-lysine (FIG. 1a: compound 2)
TCO*=N-ε-((trans-Cyclooct-2-en-1-yloxy)carbonyl)-L-lysine (FIG. 1a: compound 3)
TCO#=N-ε-((trans-Cyclooct-3-en-1-yloxy)carbonyl)-L-lysine (FIG. 1a: compound 4)
TEA=triethylamine
TFA=trifluoroacetic acid
THF=tetrahydrofurane
TLC=thin layer chromatography
UAA=unnatural amino acid

The invention claimed is:

1. A compound of the formula:

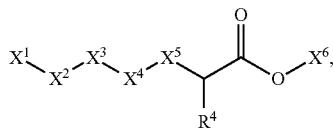

or an acid addition salt or base addition salt thereof, wherein:

$X^1$ is a group of the formula:

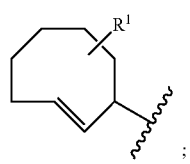

$X^2$ is —$CH_2$— or —O—;
$X^3$ is a single bond or —$(CH_2CH_2O)_m$—;
$X^4$ is —C(O)NH— or —NHC(O)—;
$X^5$ is —$(CH_2)_n$—;
$X^6$ is hydrogen, $C_1$-$C_6$ alkyl, $C_1$-$C_6$-alkoxy-$C_1$-$C_2$-alkyl, $C_2$-$C_7$-alkanoyloxy-$C_1$-$C_2$-alkyl or $C_2$-$C_7$-alkanoylsulfanyl-$C_1$-$C_2$-alkyl;

$R^1$ is hydrogen, halogen, $C_1$-$C_4$-alkyl, $(R^aO)_2P(O)OC_1$-$C_4$-alkyl, $(R^bO)_2P(O)C_1$-$C_4$-alkyl, $CF_3$, CN, OH, $C_1$-$C_4$-alkoxy, $OCF_3$, $C_2$-$C_5$-alkenoxy, $C_2$-$C_5$-alkanoyloxy, $C_1$-$C_4$-alkylaminocarbonyloxy or $C_1$-$C_4$-alkylthio, $C_1$-$C_4$-alkylamino, di-($C_1$-$C_4$-alkyl)amino, $C_2$-$C_5$-alkenylamino, $C_2$-$C_5$-alkenyl-$C_1$-$C_4$-alkylamino or di-($C_2$-$C_5$-alkenyl)amino;

$R^4$ is —OH or —$NH_2$;

$R^a$ is hydrogen or $C_2$-$C_5$-alkanoyloxymethyl;

$R^b$ is hydrogen or $C_2$-$C_5$-alkanoyloxymethyl;

m is 1; and n is 1, 2, 3 or 4.

2. The compound of claim 1, wherein the compound is selected from the group consisting of:

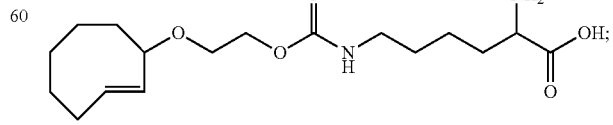

and

-continued
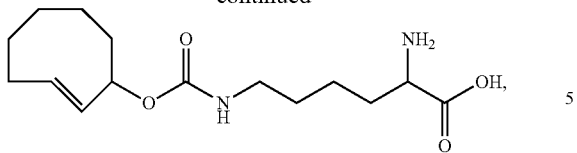
or an acid addition salt or base addition salt thereof.
3. The compound of claim 2, wherein the compound is:
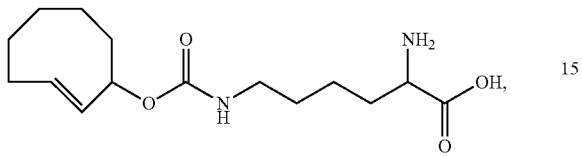
or an acid addition salt or base addition salt thereof.
* * * * *

UNITED STATES PATENT AND TRADEMARK OFFICE
CERTIFICATE OF CORRECTION

PATENT NO. : 10,519,101 B2
APPLICATION NO. : 15/111138
DATED : December 31, 2019
INVENTOR(S) : Edward Lemke et al.

It is certified that error appears in the above-identified patent and that said Letters Patent is hereby corrected as shown below:

In the Claims

Column 100, Line 42, Claim 1, please delete "$C_1$-$C_4$-alkylaminocarbonyloxy or $C_1$-$C_4$-alkylthio," and insert -- $C_1$-$C_4$-alkylaminocarbonyloxy, $C_1$-$C_4$-alkylthio, -- therefor.

Signed and Sealed this
Fifth Day of May, 2020

Andrei Iancu
*Director of the United States Patent and Trademark Office*